US009997272B2

(12) United States Patent
Stupp et al.

(10) Patent No.: US 9,997,272 B2
(45) Date of Patent: *Jun. 12, 2018

(54) MODULAR SUPRAMOLECULAR APPROACH FOR CO-CRYSTALLIZATION OF DONORS AND ACCEPTORS INTO ORDERED NETWORKS

(71) Applicant: Northwestern University, Evanston, IL (US)

(72) Inventors: Samuel I. Stupp, Chicago, IL (US); J. Fraser Stoddart, Evanston, IL (US); Alexander K. Shveyd, Rochester, NY (US); Alok S. Tayi, Niskayuna, NY (US); Chi-Hau Sue, Berkeley, CA (US); Ashwin Narayanan, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/252,852

(22) Filed: Aug. 31, 2016

(65) Prior Publication Data
US 2017/0053721 A1    Feb. 23, 2017

Related U.S. Application Data

(63) Continuation of application No. 13/476,974, filed on May 21, 2012, now Pat. No. 9,449,731.
(Continued)

(51) Int. Cl.
H01B 1/00    (2006.01)
H01B 1/12    (2006.01)
(Continued)

(52) U.S. Cl.
CPC ........... *H01B 1/121* (2013.01); *C07D 487/14* (2013.01)

(58) Field of Classification Search
CPC . H01B 1/121; H01B 1/00; H01B 1/12; C07D 487/14
(Continued)

(56) References Cited

U.S. PATENT DOCUMENTS 9,443,636 B2 * 9/2016 Stupp ................. G02B 1/02
9,449,731 B2 * 9/2016 Stupp ................. H01B 1/121
(Continued)

FOREIGN PATENT DOCUMENTS

WO    2009109781 A2    9/2009

OTHER PUBLICATIONS

Horiuchi S., et al. "Above Room Temperature Ferroelectricity in a Single Component Molecular Crystal", Nature, 2010, vol. 463, pp. 789-793.
(Continued)

Primary Examiner — Bijan Ahvazi
(74) Attorney, Agent, or Firm — Reinhart Boerner Van Deuren s.c.

(57) ABSTRACT

Organic charge-transfer (CT) co-crystals in a mixed stack system are disclosed, wherein a donor molecule (D) and an acceptor molecule (A) occupy alternating positions (DA-DADA) along the CT axis. A platform is provided which amplifies the molecular recognition of donors and acceptors and produces co-crystals at ambient conditions, wherein the platform comprises (i) a molecular design of the first constituent (α-complement), (ii) a molecular design of the second compound (β-complement), and (iii) a solvent system that promotes co-crystallization.

15 Claims, 52 Drawing Sheets

Related U.S. Application Data

(60) Provisional application No. 61/498,277, filed on Jun. 17, 2011, provisional application No. 61/488,605, filed on May 20, 2011.

(51) Int. Cl.

| | | |
|---|---|---|
| *C07D 487/14* | (2006.01) | |
| *F21V 9/00* | (2018.01) | |
| *G02B 5/02* | (2006.01) | |
| *G02C 7/10* | (2006.01) | |
| *G02F 1/361* | (2006.01) | |
| *G03B 11/00* | (2006.01) | |

(58) Field of Classification Search
USPC .................................. 252/500, 582; 548/433
See application file for complete search history.

(56) References Cited

U.S. PATENT DOCUMENTS

| | | |
|---|---|---|
| 2012/0319058 A1 | 12/2012 | Stupp et al. |
| 2016/0372229 A1* | 12/2016 | Stupp ..................... G02B 1/02 |

OTHER PUBLICATIONS

Horiuchi S., et al. "Organic Ferroelectrics", Nature Material, 2008, vol. 7, pp. 357-366.

Fujitsuka M. et al., "Electron Transfer in the Supramolecular Donor-Acceptor Dyad of Zinc Porphycene", J. Phys. Chem. A. 2009, vol. 113, pp. 3330-3335.

Pascu S. et al., "Cation-reinforced donor-acceptor pseudorotaxanes", New J. Chem., 29, 80-89, 2005.

Cubberley M. et al., "1 H NMR Investigation of Solvent Effects in Aromatic Stacking Interactions", J. Am. Chem. Soc. 2001, 123, 7560-7563.

PCT Search Report from PCT/US2012/038896 dated Feb. 1, 2013.

* cited by examiner

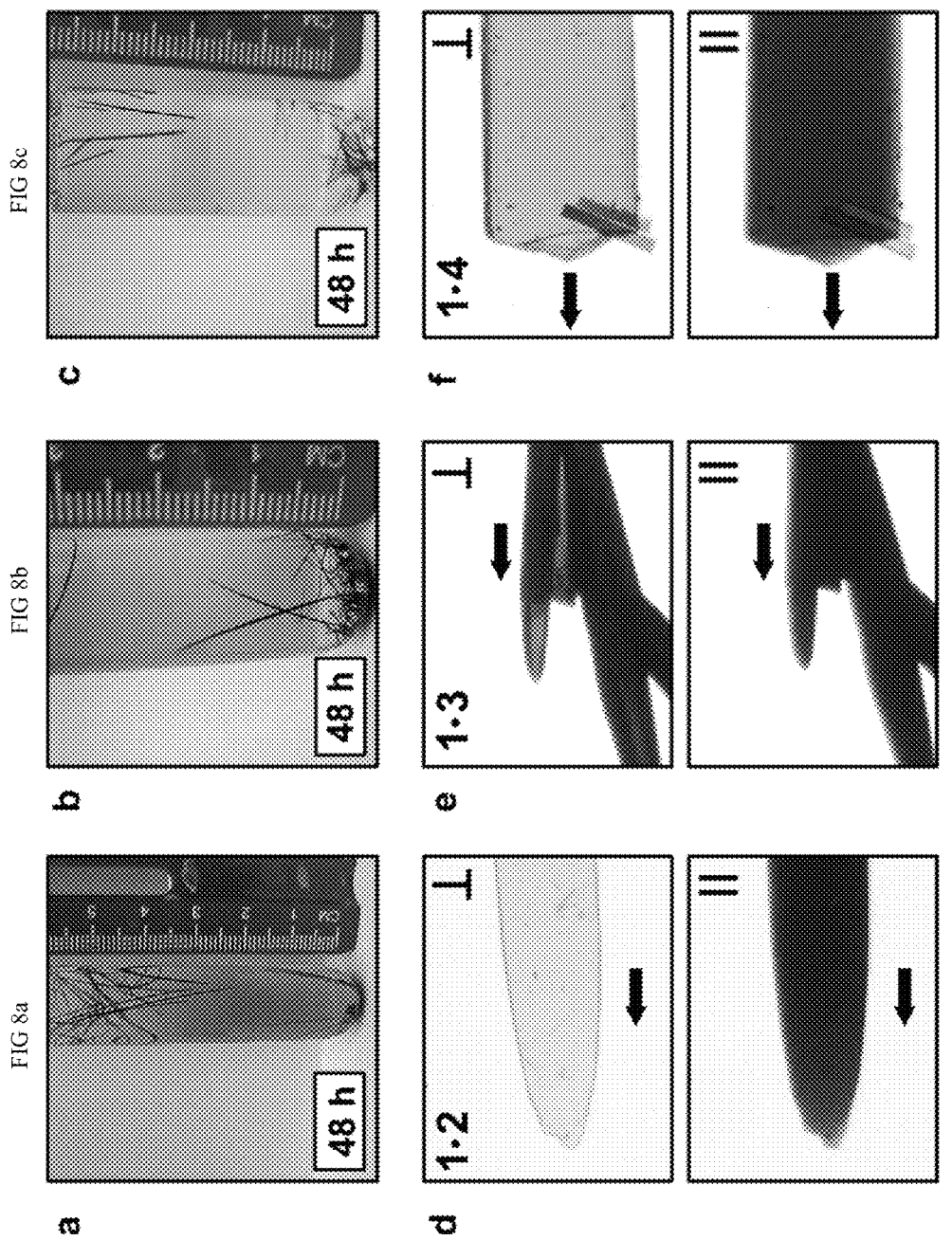

FIG 10a
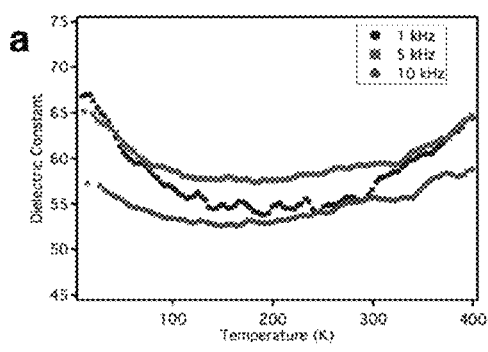
FIG 10b
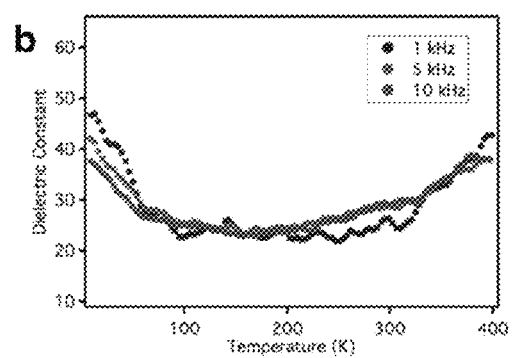
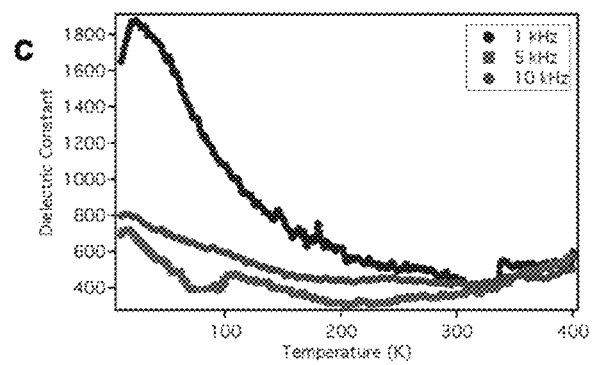
FIG 10c

FIG 11a
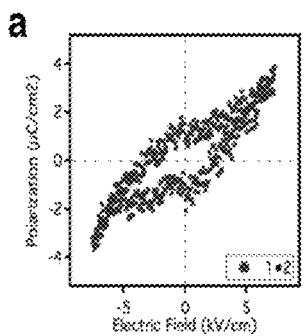
FIG 11b
FIG 11c
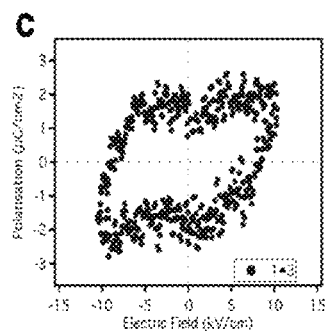
FIG 11d
FIG 11e
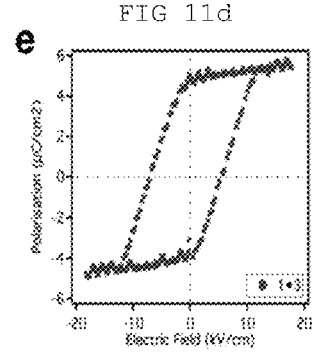
FIG 11f
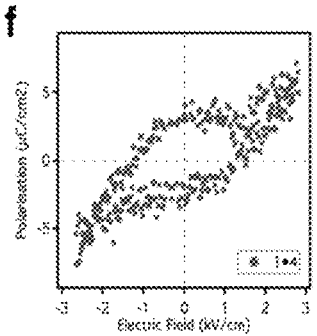
FIG 11g
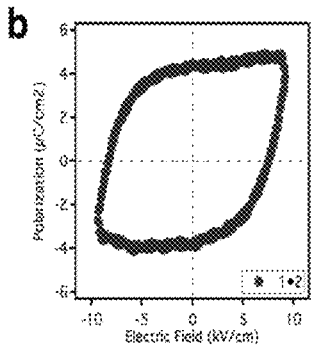
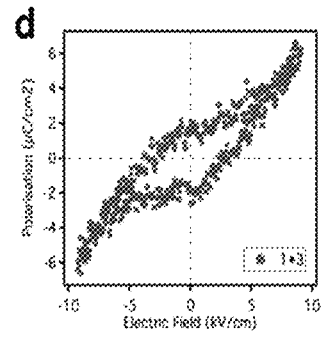
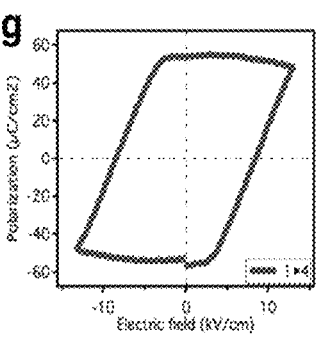

FIG 25a
FIG 25b
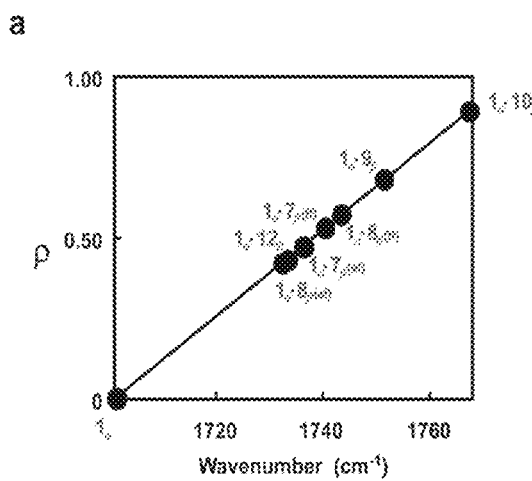
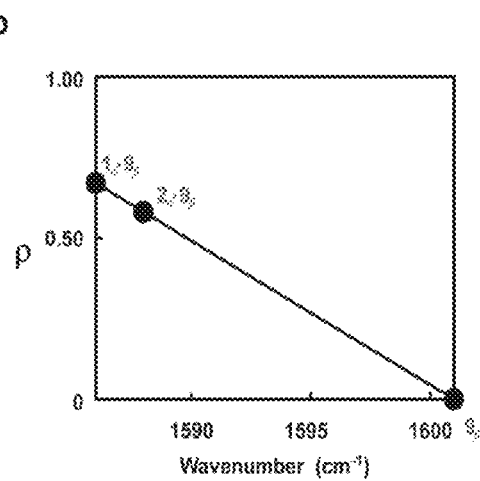
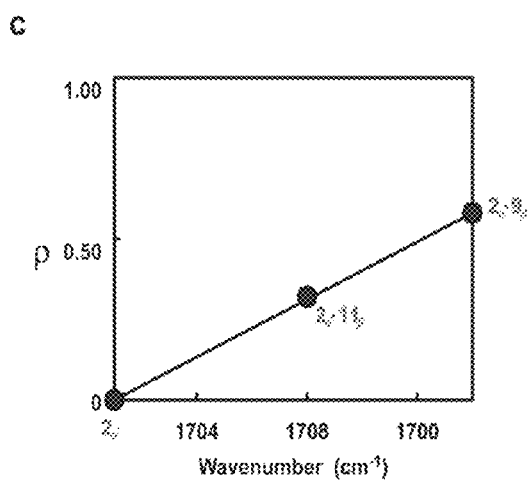
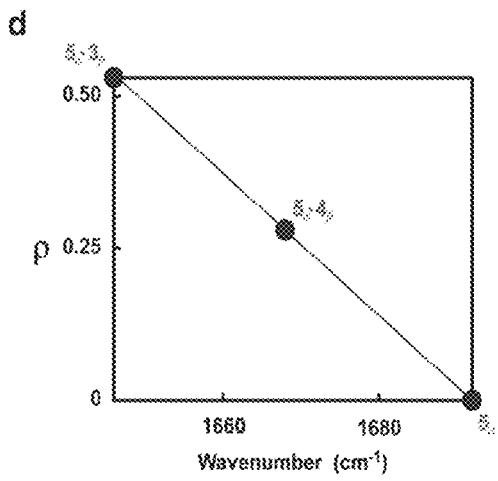
FIG 25c
FIG 25d

FIG 39a
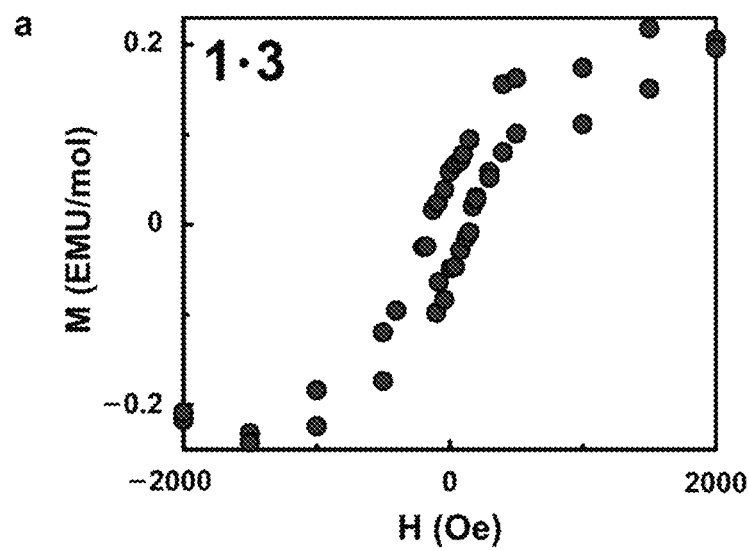
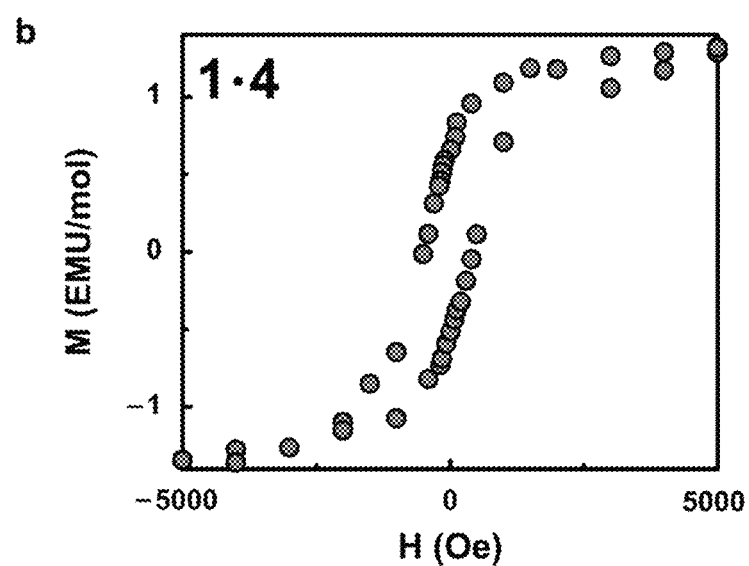
FIG 39b

FIG 40a
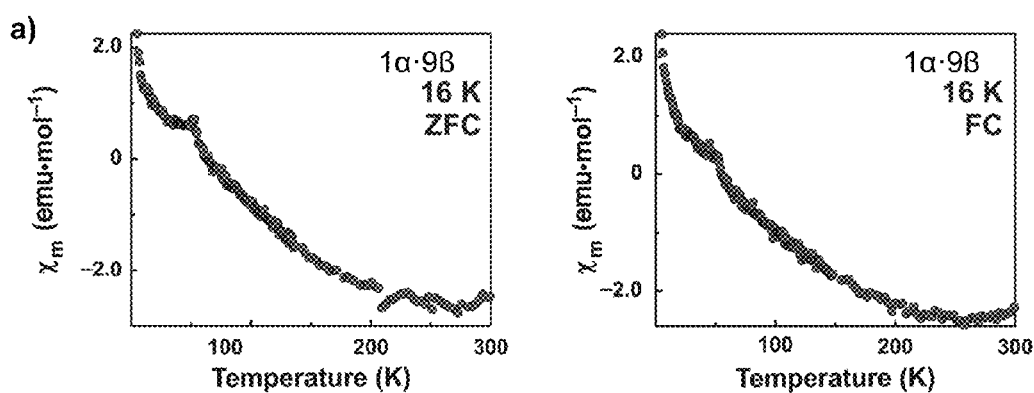
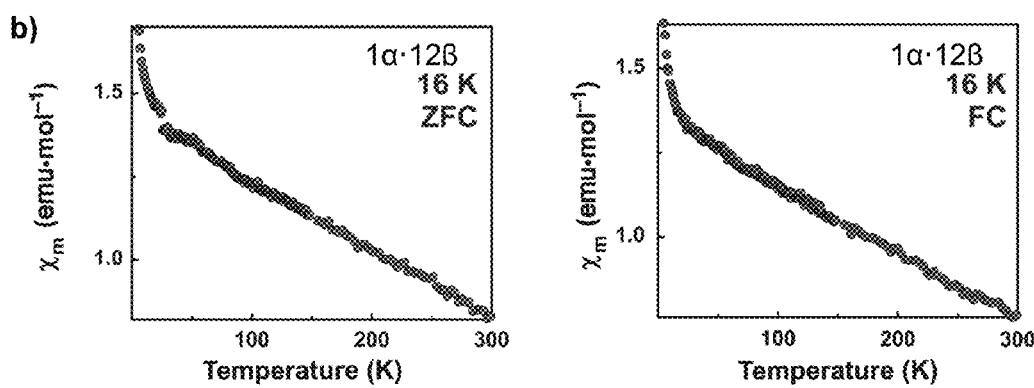
FIG 40b

FIG 41

1-Chlorobutane:

| Analysis | Method | Result | Basis | Amount |
|---|---|---|---|---|
| Fe : Iron | | | | |
| | GLI Procedure ME-70 | < 4 ppm | As Received | 788.72 mg |

1,2 Dichloroethane:

| Analysis | Method | Result | Basis | Amount |
|---|---|---|---|---|
| Fe : Iron | | | | |
| | GLI Procedure ME-70 | < 3 ppm | As Received | 951.99 mg |

Diethyl ether:

| Analysis | Method | Result | Basis | Amount |
|---|---|---|---|---|
| Fe : Iron | | | | |
| | GLI Procedure ME-70 | < 5 ppm | As Received | 506.37 mg |

| Analysis | Method | Result | Basis | Amount |
|---|---|---|---|---|
| Fe : Iron | GLI Procedure ME-70 | < 90 ppm | As Received | 22.90 mg |

9β:

| Analysis | Method | Result | Basis | Amount |
|---|---|---|---|---|
| Fe : Iron | GLI Procedure ME-70 | < 88 ppm | As Received | 18.51 mg |

FIG 43a
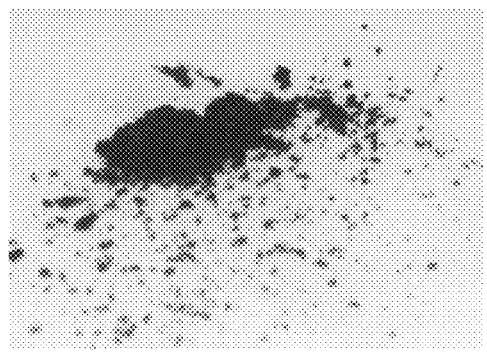
FIG 43b
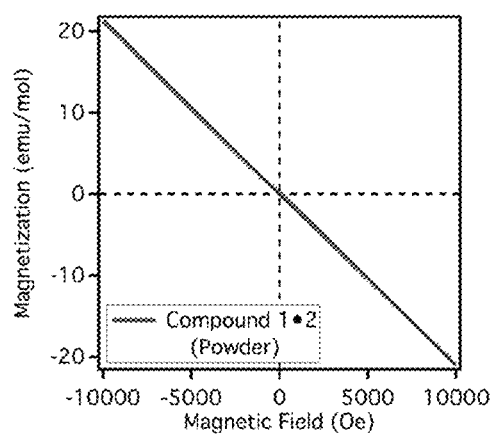
FIG 43c
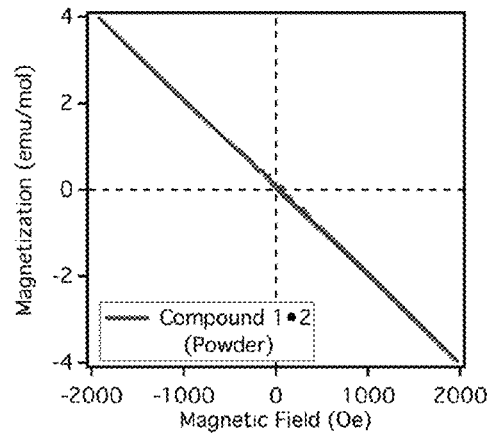
FIG 43d
Mixed Powder; 1α, 9β:
| Analysis | Method | Result | Basis | Amount |
|---|---|---|---|---|
| Fe : Iron | | | | |
| | SLI Procedure MS-70 | < 37 ppm | As Received | 33.86 mg |

FIG 44

Compound 1α·9β:

| Analysis | Method | Result | Basis | Amount |
|---|---|---|---|---|
| Fe : Iron | GJ Procedure ME-70 | < 29.3 ppm | As Received | 42.74 mg |

Compound 1α·12β:

| Analysis | Method | Result | Basis | Amount |
|---|---|---|---|---|
| Fe : Iron | GJ Procedure ME-70 | < 30.0 ppm | As Received | 26.05 mg |

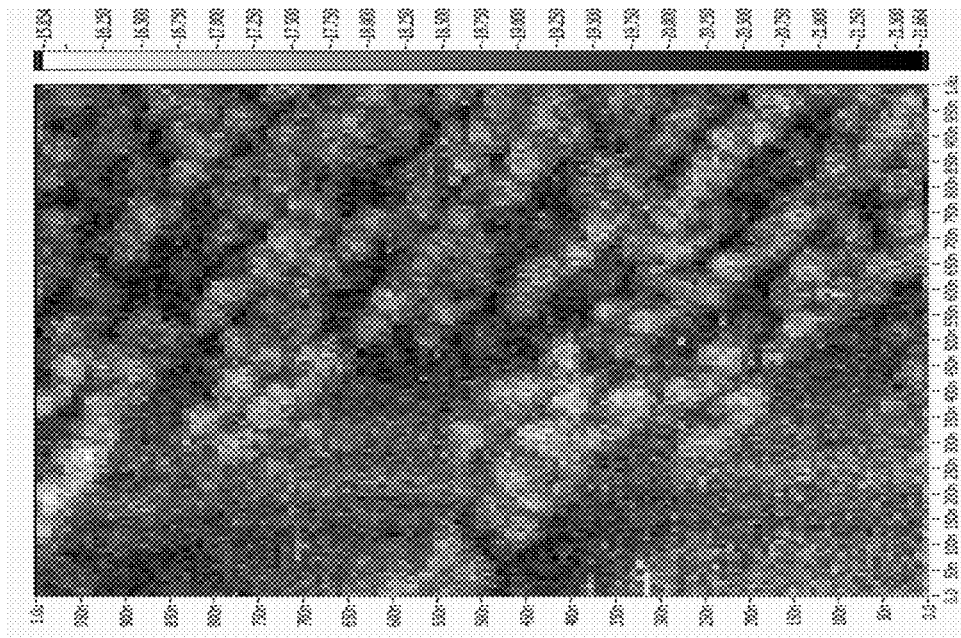
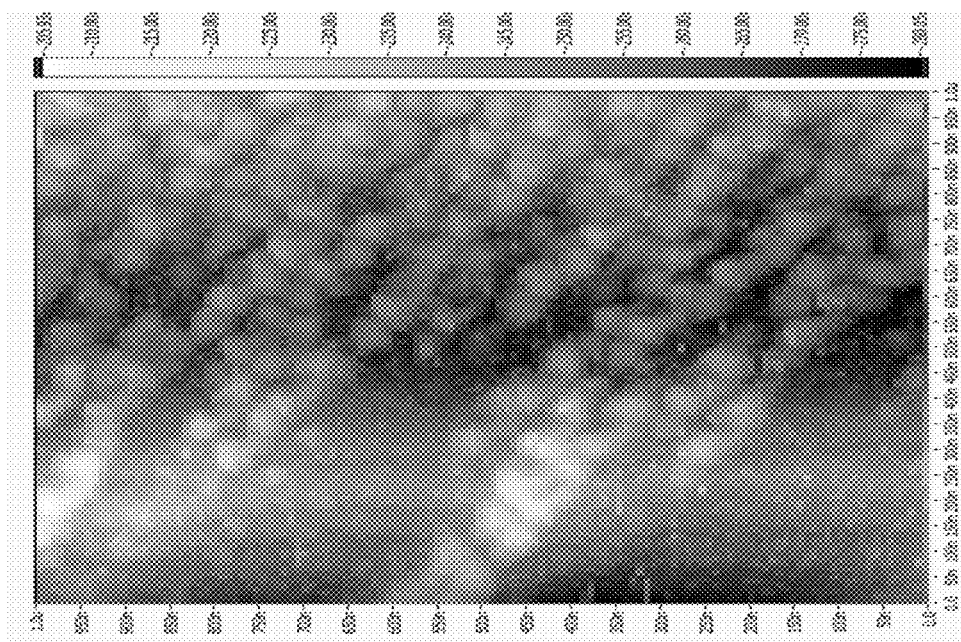
FIG 45b
FIG 45a

FIG 46a
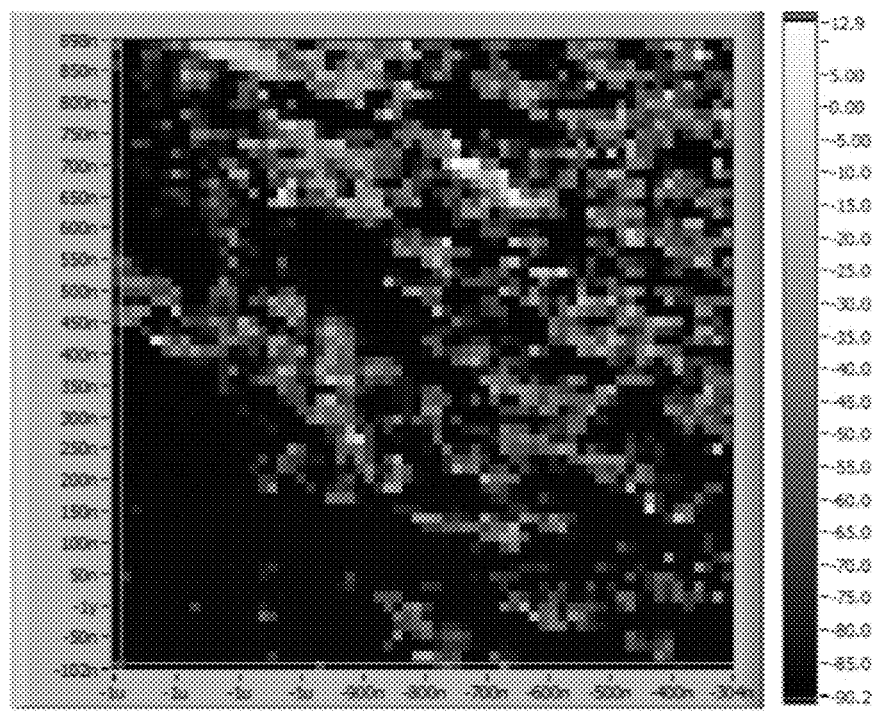
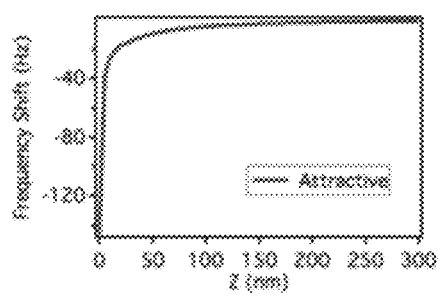
FIG 46b
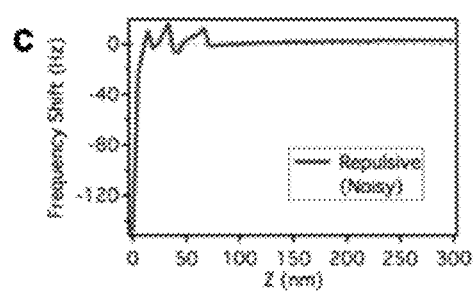
FIG 46c

FIG 47a
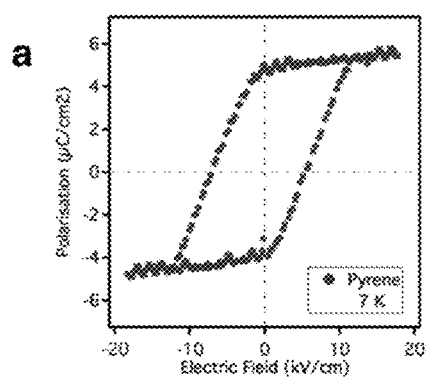
FIG 47b
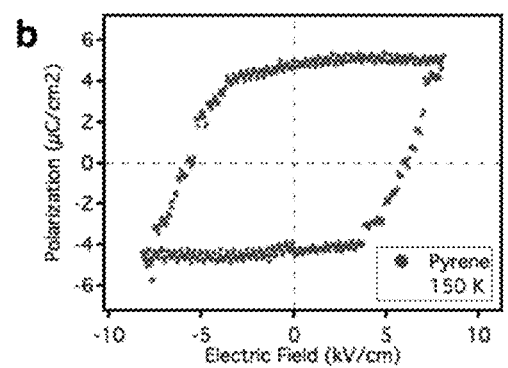
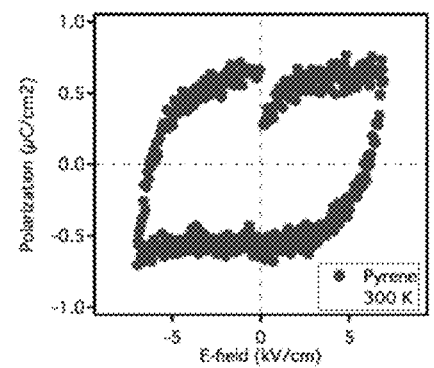
FIG 47c

FIG 49a
FIG 49b
a 
b 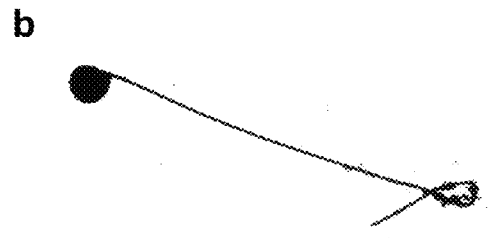

MODULAR SUPRAMOLECULAR APPROACH FOR CO-CRYSTALLIZATION OF DONORS AND ACCEPTORS INTO ORDERED NETWORKS

This application is a continuation of and claims priority to and the benefit of application Ser. No. 13/476,974 filed May 21, 2012, which claimed priority to and the benefit of application Ser. No. 61/488,605 filed May 20, 2011 and application Ser. No. 61/498,277 filed on Jun. 17, 2011— each of which is incorporated herein by reference in its entirety.

This invention was made with government support under DE-SC0000989 awarded by the Department of Energy and DMR0520513 awarded by the National Science Foundation. The government has certain rights in the invention.

FIELD OF THE INVENTION

The present invention relates generally to supramolecular charge transfer networks that exhibit ferroelectric polarization switching with a ferroelectric Curie temperature above room temperature. The polar and switchable systems disclosed herein utilize a synergy between hydrogen bonded networks and charge transfer complexation of donors and acceptor molecules in the mixed stack. This supramolecular motif is a starting point for the development of other functional organic systems that can switch under the influence of electric fields at practical temperatures.

BACKGROUND OF THE INVENTION

Since the middle of the 20th Century, organic co-crystals have been of interest to a number of researchers. Saunder, D. H. *Proc. R. Soc. London*, Ser. A 1946, 188, 31-51; Vanniekerk, J. N., et al. *Acta Crystallogr.* 1948, 1, 44-44; Andrews, L. J. *Chon. Rev.* 1954, 54, 713-776; McConnell, H. *J. Chem. Phys.* 1954, 22, 760-761; McConnell, H. M., et al. *Proc. Natl. Acad. Sci. U.S.A.* 1965, 53, 46-50; and Desantis, F., et al. *Nature* 1961, 191, 900-901. Charge-transfer (CT) co-crystals, in particular, have been studied for their structural modularity and novel properties. Herbstein, F. H. *Crystalline Molecular Complexes and Compounds: Structures and Principles*, Oxford University Press: Oxford, N.Y., 2005; Klosterman, J. K., et al. *Chem. Soc. Rev.* 2009, 38, 1714-1725; Jerome, D., et al. *Adv. Phys.* 2002, 51, 293-479; Horiuchi, S., et al. *J. Phys. Soc. Jpn.* 2006, 75, 051016; Saito, G., et al. *Bull. Chem. Soc. Jpn.* 2007, 80, 1-137. They are modular, inexpensive, and solution-processable materials that can be designed to exhibit properties such as ferroelectricity, conductance, magnetism, and optical nonlinearity. Although the properties of these crystals are well understood, there has been very little research aimed at incorporating them into organic electronic devices.

The lattice is composed of an electron deficient molecule, the acceptor (A), and an electron-rich constituent, the donor (D). When the donor and acceptor are complexed, an electron wave oscillates between them, i.e., the CT. In the most basic model, the CT interaction can be viewed as a charge donation from the donor HOMO to the acceptor LUMO. Torrance, J. B., et al. *Phys. Rev. Lett.* 1981, 46, 253-257. More comprehensive research on the ground state of DA co-crystals reveals, however, that the CT interaction actually varies significantly in terms of its structure and complexity. Murata, T., et al. *J. Am. Chem. Soc.* 2007, 129, 10837-10846; Saito, G., et al. *Philos. Trans. R. Soc. London, Ser. A* 2008, 366, 139-150. For convenience, CT is typically categorized by the parameter ionicity (p) that represents the degree of electron donation ($0 \leq p \leq 1$) between the donor and the acceptor

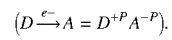

$$(D \xrightarrow{e^-} A = D^{+P} A^{-P}).$$

Electron donor-acceptor ordered networks are good candidates for organic ferroelectrics because of the possible long range orientation of charge transfer dipoles. The canonical electron donor-acceptor (DA) systems, the mixed stack tetrathiafulvalene (TTF) with halogenated quinones, like TTF•chloranil (TTF•QCl$_4$) and TTF•bromanil (TTF•QBr$_4$), have been investigated by X-ray crystallography, vibrational spectroscopy, and electrical measurements. Horiuchi, S., et al. *Science* 2003, 299, 229-232 (2003); Horiuchi, S., et al. *Nature Mater.* 7, 357-366 (2008); Collet, E. et al. *Science* 300, 612-615 (2003); Kagawa, F., et al. *Nat Phys* 6, 169-172 (2010); Torrance, J. B. et al. *Phys. Rev. Lett.* 47, 1747-1750 (1981); Girlando, A., et al. *J. Chem. Phys.* 79, 1075-1085 (1983); Okamoto, H. et al. *Phys. Rev. B* 43, 8224-8232 (1991); Soos, Z. G. *Chem. Phys. Lett.* 440, 87-91 (2007); and Kagawa, F. et al. *Phys. Rev. Lett.* 104, 227602-227606 (2010). The TTF•QCl$_4$ complex undergoes a ferroelectric phase transition, associated with a discontinuous jump in ionicity (ρ) at the Curie temperature ($T_c$=81 K), and dimerization into DA pairs (D$^0$ A$^0$ D$^0$ A$^0$ □ D$^{\delta+}$A$^{\delta-}$ D$^{\delta+}$A$^{\delta-}$) breaking centro-symmetry. Categorizing this critical point as a ferroelectric transition was first postulated in 1991 when an anomalous dielectric spike was also observed at $T_c$, for TTF•QCl$_4$. The TTF•QBr$_4$ crystal, already ionic (ρ>0.5) at room temperature, also dimerises into DA pairs at 53° K as result of a spin-Peierls instability. Girlando, A., et al. *Solid State Commun.* 54, 753-759 (1985). Even with a ferroelectric ground state, however, measuring reversible polarization under an electric field has only been shown in TTF•QBr$_4$.

Conventional organic CT crystals can be co-crystallized into two different packing arrangements, segregated stacks and mixed stacks. Anderson, P. W., et al. *Solid State Commun.* 1973, 13, 595-598; Iwasa, Y., et al. *Phys. Rev. B: Condens. Matter* 1990, 42, 2374-2377; Kuwatagonokami, M., et al. *Nature* 1994, 367, 47-48; and Hamilton, D. G., et al. *Aust. J. Chem.* 1997, 50, 439-445. In segregated stacks, the donor and acceptor pack edge-to-edge in separate columns (DDD, AAA), while in crystals with a mixed stack motif, the donor and acceptor occupy alternating positions (DADADA) along the CT axis. These two packing arrangements have considerably different physical properties. Co-crystals with segregated stacks typically exhibit metallic conductivity since the overlapping n orbitals between stacks of open shell donors and acceptors merge into conduction bands. Jerome, D. *Chem. Rev.* 2004, 104, 5565-5591. A mixed stack system is primarily known for polar phase transitions with changes in temperature, variations in pressure and optical excitation. Bruinsma, R., et al. *Phys. Rev. B: Condens. Matter* 1983, 27, 456-466; Masino, M., et al. *Phys. Chern. Chern. Phys.* 2001, 3, 1904-1910; Iwasa, Y., et al. *Synth. Met.* 1991, 42, 1827-1830; Tokura, Y., et al. *Solid State Cornmun.* 1986, 57, 607-610; Girlando, A., et al. *Solid State Commun.* 1986, 57, 891-896; and Koshihara, S., et al. *Phys. Rev. B: Condens. Matter,* 1990, 42, 6853-6856. Other exotic physical phenomena, like nonlinear electronic transport, magnetic ordering, and optical nonlinearity, have been identified in mixed stack crystals as well. Ferraris, L., et al. *J Am. Chern. Soc.* 1973, 95, 948-949; Samoc, M., et al. *J. Chem. Phys.* 1983, 78, 1924-1930; Massa, D., et al. *Mol.*

*Cryst. Liq. Cryst. Sci.* 1989, 175, 93-117; Kondo, R., et al. *Chem. Lett.* 1999, 333-334; Kondo, R., et al. *Synth. Met.* 2001, 120, 995-996; Mitani, T, et al. *Phys. Rev. Lett.* 1984, 53, 842-845; Tokura, Y, et al. *Phys. Rev. B: Condens. Matter* 1988, 38, 2215-2218; Iwasa, Y, et al. *Phys. Rev. B: Condens. Matter* 1989, 39, 10441-10444; Hughes, R C., et al. *J Chem. Phys.* 1968, 48, 1066-1076; Huizinga, S., et al. *Phys. Rev. B: Condens. Matter* 1979, 19, 4723-4732; Hasegawa, T, et al. *Solid State Commun.* 1997, 103, 489-493; Kagawa, F., et al. *Nature Phys.* 2010, 6, 169-172; Rao, S. M., et al. *J Appl. Phys.* 1991, 70, 6674-6678; Ezaki, H., et al. *Solid State Commun.* 1993, 88, 211-216; Mazumdar, S., et al. *Chern. Phys.* 1996, 104, 9283-9291; Wong, M. S., et al. *Adv. Mater.* 1997, 9, 554-557; Zyss, J., et al. *Chern. Mater.* 2003, 15, 3063-3073.

Research that relies on organic co-crystals presents numerous challenges. Most notably, it can be difficult to grow high quality crystals that are large enough for experiments in integrated systems and devices. Being able to produce these materials quickly and reproducibly would facilitate their use in basic research and also in applications. It is therefore desirable to provide a self-assembly platform which amplifies the molecular recognition of donors and acceptors and produces co-crystals at ambient conditions.

SUMMARY OF THE INVENTION

In light of the foregoing, it is an object of the present invention to provide organic charge-transfer (CT) co-crystals into a mixed stack system, wherein a donor molecule (D) and an acceptor molecule (A) occupy alternating positions (DADADA) along the CT axis. A platform is provided which amplifies the molecular recognition of donors and acceptors and produces co-crystals at ambient conditions, wherein the platform comprises (i) a molecular design of the first constituent (α-complement), (ii) a molecular design of the second compound (β-complement), and (iii) a solvent system that promotes co-crystallization. The terms α-complement and β-complement are structural designations that refer to the complementary recognition of the components. These designations are not associated with the electronic character of the molecules, and either complement can be an electron donor or an electron acceptor. The co-crystals disclosed herein are not only CT pairs but are also capable of assembling into ordered three-dimensional supramolecular networks.

Accordingly, it will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

Other objects, features, benefits and advantages of the present invention will be apparent from this summary and the following descriptions of certain embodiments, and will be readily apparent to those skilled in the art. Such objects, features, benefits and advantages will be apparent from the above as taken into conjunction with the accompanying examples, data, and all reasonable inferences to be drawn therefrom. The disclosures in this application of all articles and references, including patents, are incorporated herein by reference.

BRIEF DESCRIPTION OF THE DRAWINGS

FIGS. 8a-f provide images showing the growth of LASO networks after 48 hours for (a) co-crystal 1α•9β; (b) co-crystal 1α•10β; and (c) co-crystal 1α•12β; and optical microscopy of very thin (>10 μm) co-crystals with linearly polarized white light for (d) co-crystal 1α•9β; (e) co-crystal 1α•10β; and (f) co-crystal 1α•12β.

FIGS. 10a-c show the temperature variation of the dielectric constant of LASO (a) co-crystal 1α•9β; (b) co-crystal 1α•10β; and (c) co-crystal 1α•12β.

FIGS. 11a-g provide polarisation hysteresis curves for complex 1α•9β measured at (a) 300° K and (b) 74° K; polarisation hysteresis curves for complex 1α•10β measured at (c) and (d) 300° K and at (e) 7° K; polarisation hysteresis curves measured for complex 1α•12β at (f) 300° K and (g) 7° K.

FIGS. 25a-d provide linear graphs used to determine the ionicity, based on the shifting of the ungerade modes in the IR spectra; (a) follows the shift of ν (C=O) for $1_\alpha$; (b) follows the shift of ν (C=C) for $9_\beta$; (c) follows the shift of ν (C=O) for $2_\alpha$; and (d) follows the shift of ν (C=O) for $3_\beta$.

FIGS. 39a-b provide graphs for magnetic hysteresis of LASO (a) co-crystal 1α•9β; and (b) co-crystal 1α•12β.

FIGS. 40a-b provide graphs for zero-field cool and field cool magnetisation versus temperature plots for LASO(a) co-crystal 1α•9β; and (b) co-crystal 1α•12β.

FIG. 41 shows the iron analysis of solvents used in LASO co-crystallisation.

FIG. 42 shows the iron analysis of untreated compounds 1α and 9β.

FIGS. 43a-d (a) is an image of mixed powder of compounds 1α and 9β; M(H) curves at 7 K for mixed powder of compounds (b) 1α and (c) 9β; (d) iron analysis report for mixed compound 1α and 9β.

FIG. 44 shows the iron analysis for co-crystal 1α•9β and co-crystal 1α•12β.

FIGS. 45a-b are a magnetic force microscopy imaging in Lift-off Mode for co-crystal 1α•12β; (a) plots of the height (nm); and (b) frequency shift at 80 nm.

FIGS. 46a-c (a) are a magnetic force microscopy, Z-spectroscopy plot of repulsive and attractive potentials across the surface of crystal 1α•12β; (b) is a plot of frequency shift versus height (nm) illustrating an attractive potential; (c) is a plot of frequency shift versus height (nm) characteristic of a repulsive potential.

FIGS. 47a-c are polarization hysteresis of compound 1α•10β at (a) 7 K; (b) 150 K; and (c) 300 K.

FIGS. 49a-b provide optical images of (a) ferroelectric device with gold paste and wire; and (b) ferroelectric device with gold paste and wire at voltage >900V and higher temperatures, wherein crystals melted.

DETAILED DESCRIPTION OF THE INVENTION

Accordingly, a non-limiting embodiment of the invention is an organic charge-transfer (CT) co-crystal in a mixed stack system, wherein the co-crystal consists essentially of an electron acceptor molecule (A) and an electron donor molecule (D), wherein one of A and D is an α-complement and the other one of A and D is a β-complement, such that the β-complement is incorporated into the α-complement through molecular linkages in a solvent system to form a co-crystalline supramolecular network, wherein one or more of the molecular linkages between the α-complement and the β-complement use adaptive intermolecular recognition to form the one or more molecular linkages, the co-crystal characterized by having a crystal superstructure comprising a mixed stack lattice (DADADA) and a topologically intricate hydrogen-bonded network.

Figure 5A:
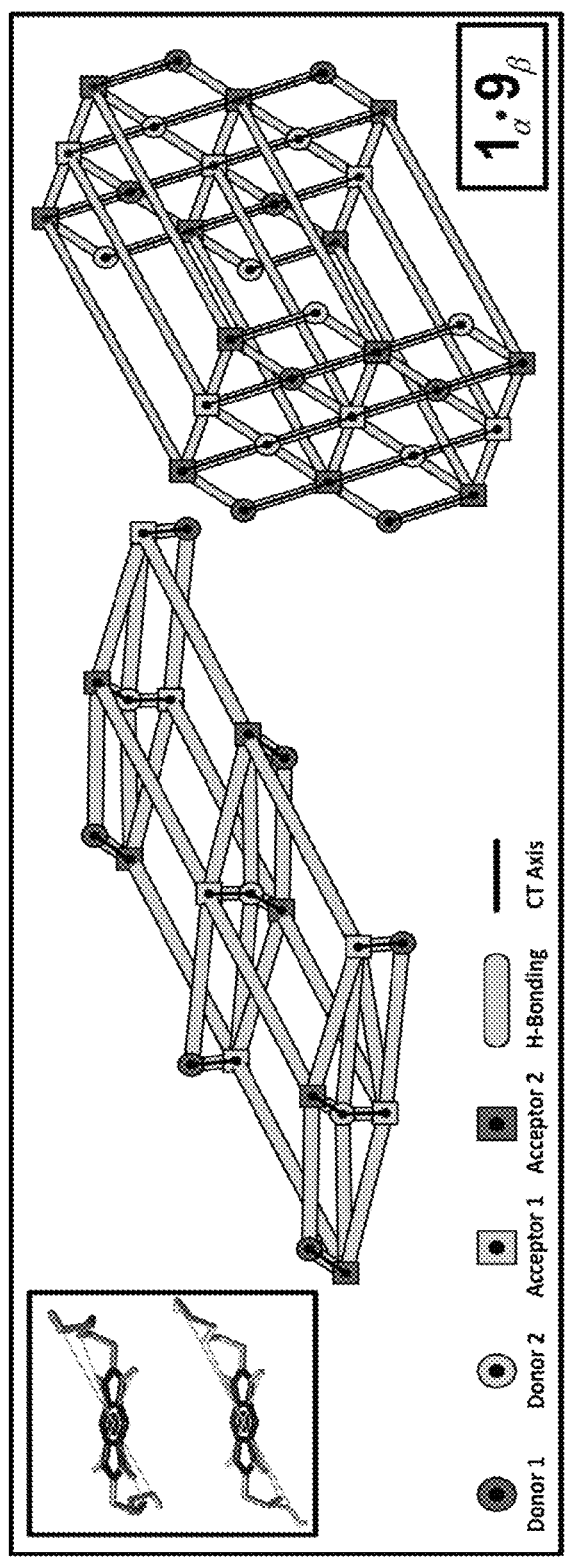
FIGS. 5a-c provide noncovalent connectivity diagrams depicting the global topology of the hydrogen bonded network for systems 1α•9β, 1α•10β, and 1α•12β; (a) diagram showing the network topology of the system 1α•9β; (b) diagram showing the network topology of the system 1α•10β; (c) diagram showing the network topology of the system 1α•12β.
Figure 5B:
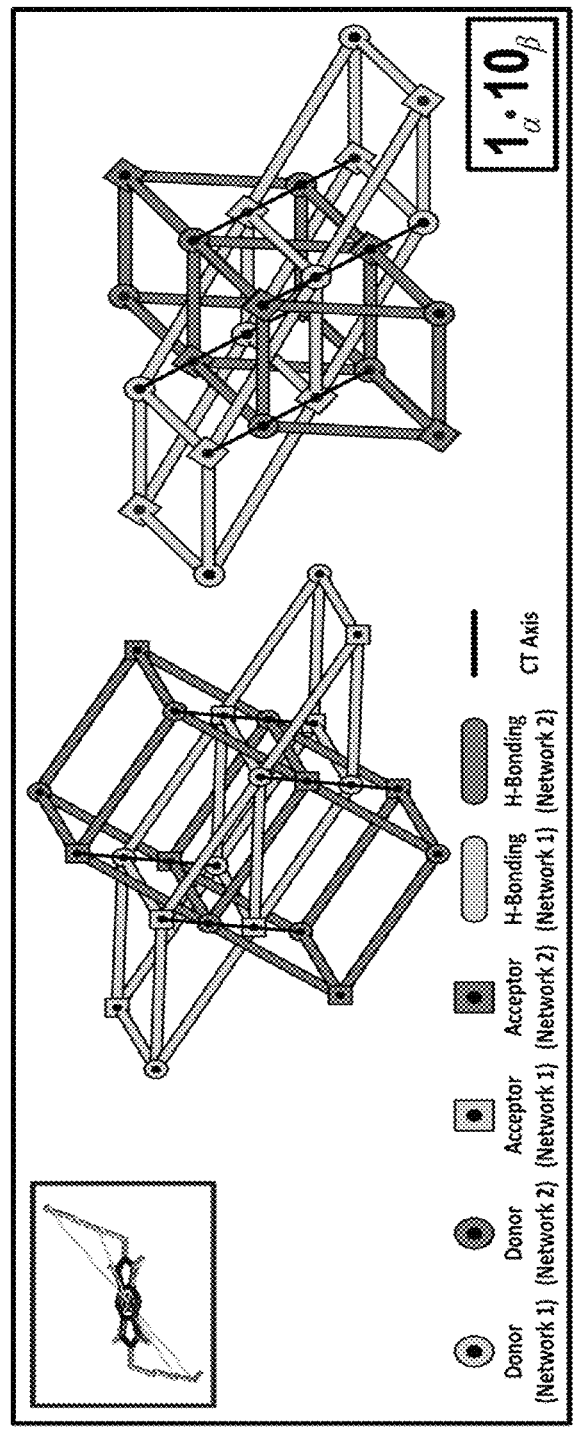
Figure 5C:
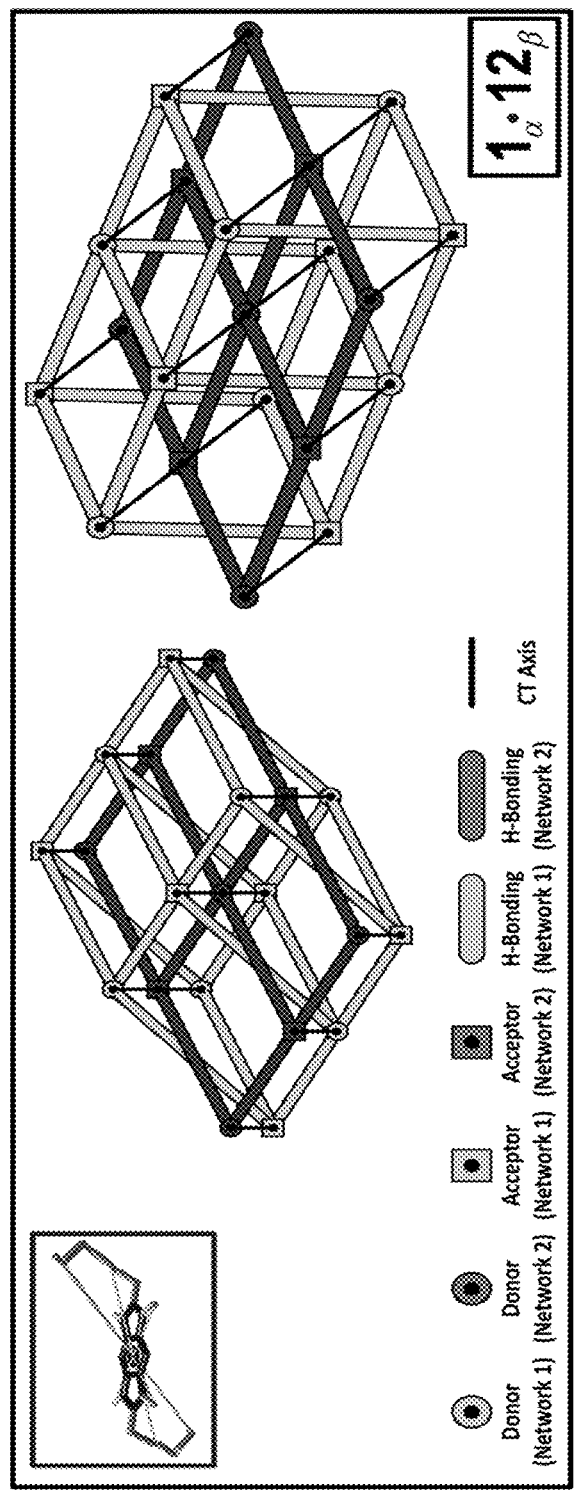

In an embodiment of the invention, the α-complement makes use of a binding motif referred to as adaptive intermolecular recognition. Adaptive intermolecular recognition is defined as the use of conformational isomerism (flexibility) by a molecule to alter the spatial distribution of its recognition sites to achieve energetically stable intermolecular binding in a solid supramolecular network (Aakeroy, C. B., et al. *Crystengcomm* 2010, 12, 22-43 and Moulton, B., et al. *Chem. Rev.* 2001, 101, 1629-1658, both incorporated herein by reference). The structure of a molecule that exhibits adaptive intermolecular recognition has two distinguishing criteria, (i) conformational flexibility (this term excludes hydrogen atoms as well as small distortions of molecular geomtery associated with lattice packing, as for example, bond lengthing or the deviation of an aromatic ring from planarity); and (ii) recognition sites that have a unique distribution of distances relative to the molecular centroid for every conformational isomer (FIG. 5). The use of conformational flexibility to achieve intermolecular binding (adaptive intermolecular recognition) in the lattice distinguishes the co-crystals described herein from network solids utilizing rigid molecules whose recognition sites have a fixed distance with respect to the molecular centroid, e.g. coordination polymers and metal organic frameworks.

Figure 1:
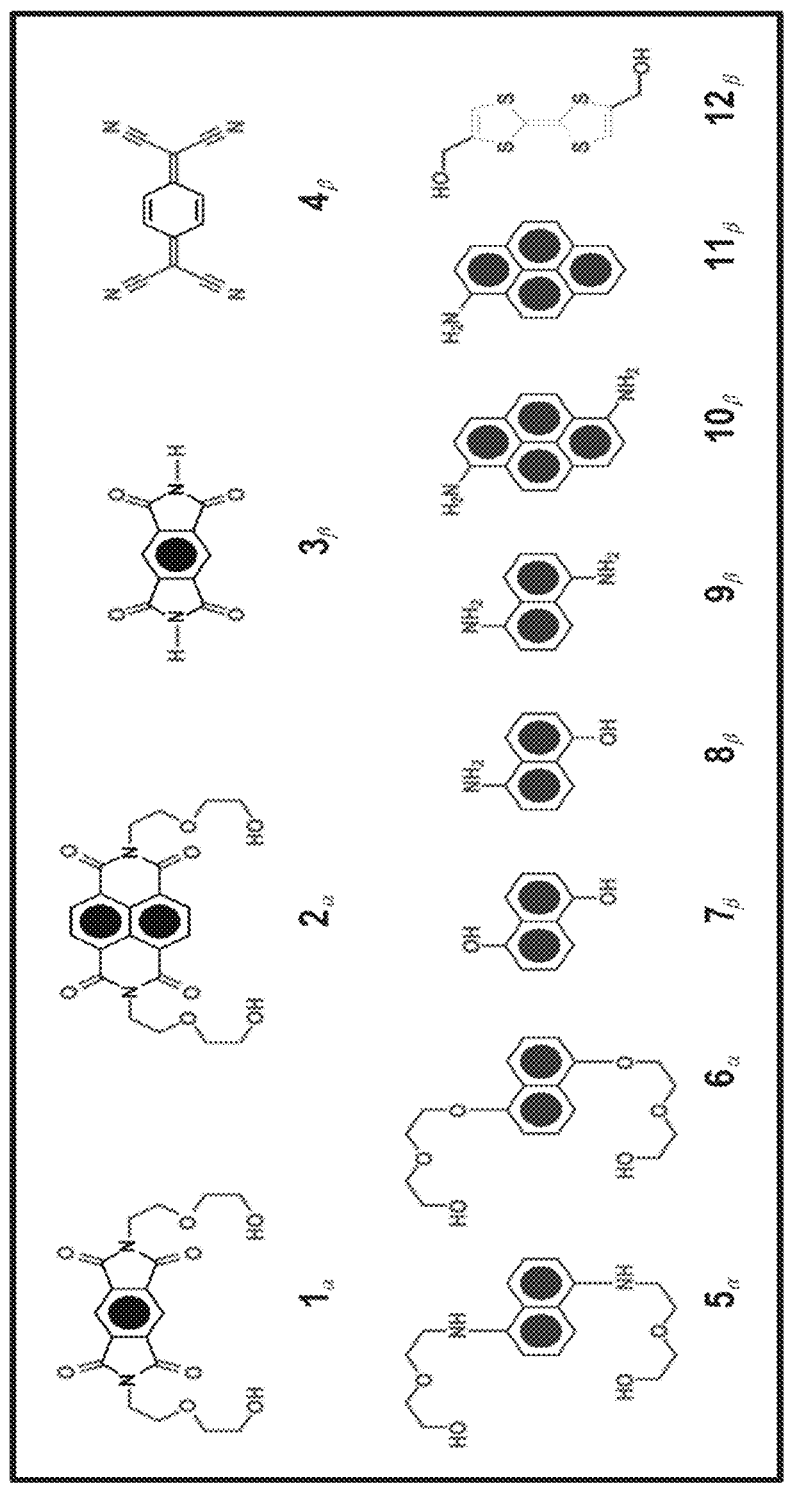
FIG. 1 provides the structural formulas of the lock-arm supramolecular (LASO) ordering electron donors and electron acceptors used in the self-assembly of ten network solids.

As described herein, 1α, 2α, 5α, and 6α, have the conformational flexibility needed for adaptive intermolecular recognition. 1α is a good illustration of how adaptive intermolecular recognition is used in the systems described herein. It has two flexible diethylene glycol appendages (FIG. 1). Each appendage (or α'-arm) has two recognition sites for hydrogen bond (H-bond) formation, i.e., an ether oxygen atom and a hydroxyl group. In co-crystals which contain 1α, the molecules that neighbor 1α also have supramolecular recognition sites (Desiraju, G. R. *Angew.*

Figure 3:
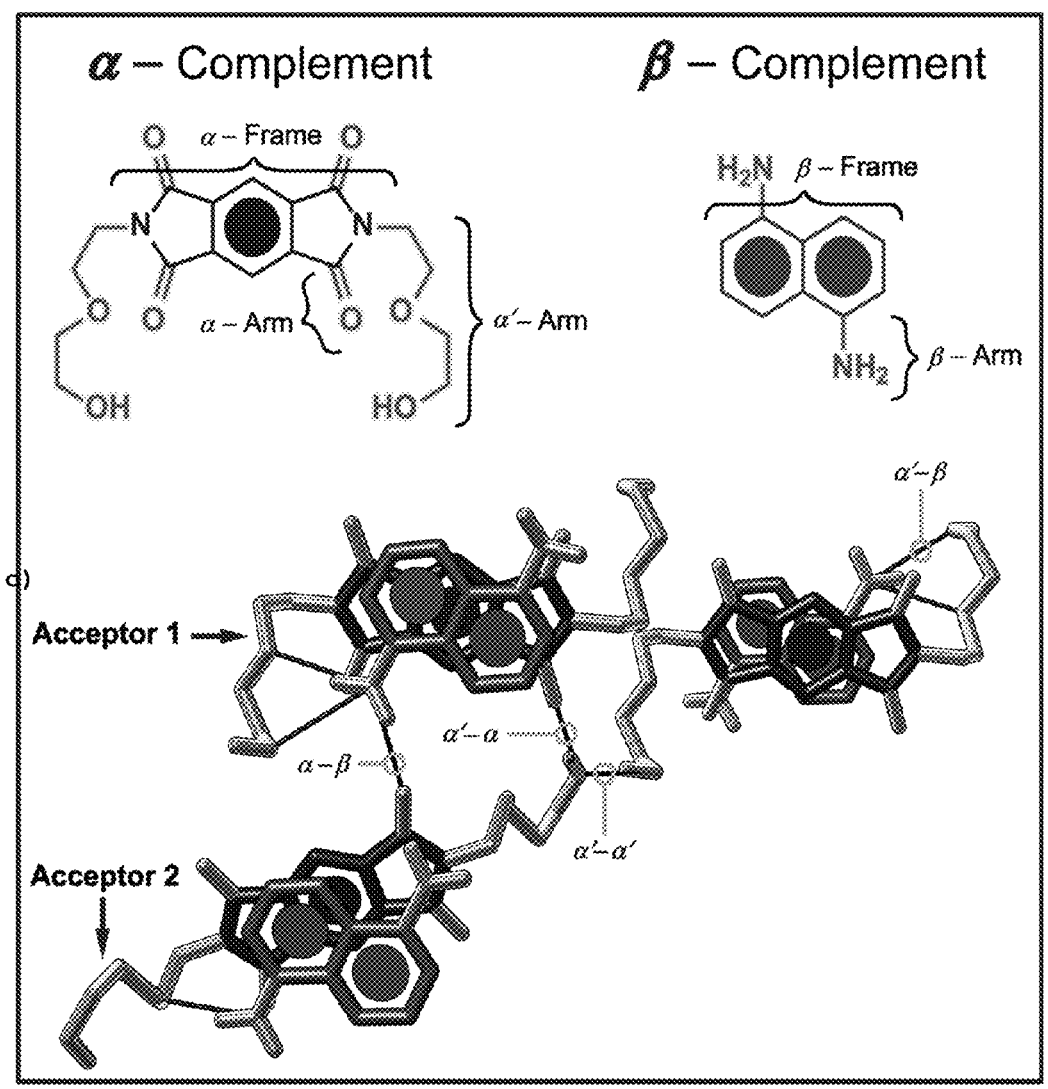
FIG. 3 is a diagram illustrating the use adaptive intermolecular recognition in the system 1α•9β.
Figure 4:
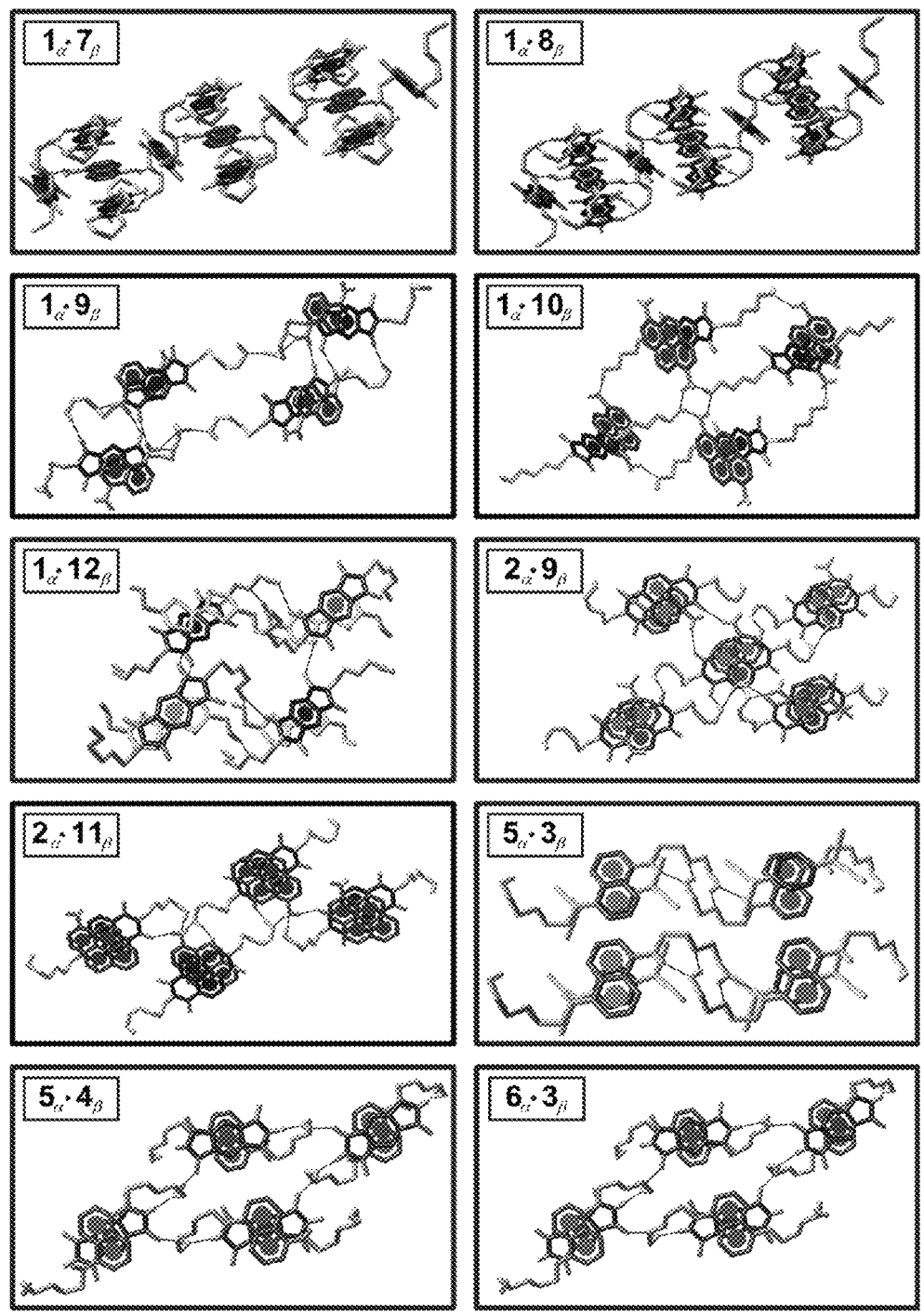
FIG. 4 provides diagrams that slice through the crystal structures of the ten LASO network solids.

Chem. Int. Ed. 1995, 34, 2311-2327, incorporated herein by reference) (C=O, —NH₂, —OH), and the glycol appendages "reach" for them to form the most thermodynamically stable H-bonds (FIG. 3 and FIG. 4). As a result, the conformations of the glycol chains adapt to the spatial positions of local recognition sites with the conformational changes, depending on the donor used in the co-crystal (FIG. 5).

To initiate the self-assembly, the α-complements (α) are paired with a smaller CT partner (donor or acceptor) with one or more rigid H-bond recognition sites such as amino, carbonyl, ether and hydroxyl moieties (FIG. 2 and FIG. 3) called the β-complement (β). The only β that is capable of adaptive intermolecular recognition is 12β. This fact makes 1α•12β unique since both constiuents engage in adaptive intermolecular recognition. In the crystallizing solution, the α and β associate through CT. It is believed, however, that the complementary H-bonding interactions between the flexible and rigid moieties on α and β drive the molecules to self-assemble into an energetically stable network solid.

In another embodiment of the invention, the methods used to produce the co-crystals of the invention should preferably exercise a strong influence on the self-assembly of α and β. When a mixture of α and β is combined in the optimal solvent system, expedient self-assembly under ambient conditions should be observed. The dependence of amplified co-crystal growth on the solvent suggests that the crystallization solution promotes the self-assembly of the constituents. The solvent system can be one solvent or a mixture of solvents. The solvent(s) is, preferably, an organic solvent. In a more preferred embodiment, Table 1 provides examples of solvent systems employed by the methods for producing the co-crystals.

TABLE 1

| Co-Crystal | Solvent System | Concentration[a] (mg/mL) | Molar Ratio (β:α) | Growth Time (d) |
|---|---|---|---|---|
| 1α·9β | Dichloroethane/Diethyl Ether (200/1) | 2 | 2 | 3 |
| 1α·10β | Dichloroethane/Diethyl Ether (200/1) | 1.5 | 2 | 3 |
| 1α·12β | Dichloroethane/Diethyl Ether (200/1) | 1 | 2 | 3 |
| 1α·7β | Dichloroethane/Diethyl Ether (200/1) | 1.5 | 2 | 3 |
| 1α·8β | Dichloroethane/Diethyl Ether (200/1) | 1.5 | 2 | 3 |
| 2α·9β | Dichloroethane/Diethyl Ether (200/1) | 2 | 15[b] | 3 |
| 2α·11β | Dichloroethane/Diethyl Ether (200/1) | 1 | 2 | 3 |
| 6α·3β | N-Methylpyrrolidone | 2 | 2 | 5 |
| 5α·3β | Dichloroethane/Diethyl Ether (200/1) | 2 | 2 | 3 |
| 5α·4β | N-Methylpyrrolidone | 2 | 2 | 5 |

[a]Concentration of the electron acceptor (α or β) in the crystallizing solution only.
[b]Concentration needed to initiate self-assembly.

As used herein, the self-assembly platform producing the co-crystals is referred to as Lock-Arm Supramolecular Ordering (LASO). A LASO network solid is defined as a crystalline supramolecular network wherein one or more of the molecular linkages use adaptive intermolecular recognition to bind to its neighboring molecules. The crystal superstructures (FIG. 4) of the LASO networks used herein constitute a combination of a mixed stack lattice and a topologically intricate H-bonded network. Preferably, the αs and βs are tightly packed and the crystals are devoid or substantially devoid of solvent. Also preferably, the use of the LASO platform is applied to diimide acceptors.

The D and A components used in co-crystal systems are shown in FIG. 1. As used herein, the ring system of a molecule is the "frame" (FIG. 3), and any appendage extending from the frame that has a supramolecular binding site is an "arm". For simplicity, aromatic hydrogen atoms on the frame will not be classified as arms. In addition to arms, the recognition sites, such as the sulfur atoms in 12β, are incorporated into the frame and are referred to as "sites". The nitrogen atoms in the diimide molecule are sterically hindered hydrogen bond acceptors and are therefore not considered sites. In a LASO co-crystal, both complementary molecules, i.e., α and β (FIG. 4) have arms (FIG. 3). The α is the molecule that contains the longest conformationally flexible arm extending from the frame (measured by the number of atoms). This appendage is called the α'-arm. The α can have one or more, and preferably two or more, arms, and even more preferably four or more, arms, of which at least one, and preferably two, is an α'-arm. All other arms are denoted without the prime symbol, e.g., the shorter β-arms on the β or the rigid C=O α-arms extending from the α frame (FIG. 1 and FIG. 3). The β is the molecule with one or more, preferably at least two, shorter arms that is incorporated into the supramolecular framework of a LASO network solid through molecular recognition with α. The structures in FIG. 1 are the αs and βs that are used to create the LASO systems (FIG. 2a and FIG. 4) described herein. In the specific non-limiting examples of FIG. 1, there are four αs, two six-arm electron acceptors (1α, 2α) and two, two-arm electron donors (5α, 6α). All the αs have a pair of similar α'-arms based on a diethylene glycol moiety, but in addition to the α'-arm, 1α and 2α also have four shorter carbonyl α-arms. For the βs, two electron acceptors (3β, 4β) and six electron donors (7β-12β) are used. Acceptors 3β and 4β are six-arm and four-arm βs, respectively. Donors 7β-10β are all two-arm βs, while 11β is a one-arm β. The donor molecule 12β is the most distinct of the βs. It has two R=CH₂OH β-arms, and four sulfur sites making it a two-arm, four-site β.

Figure 6A:
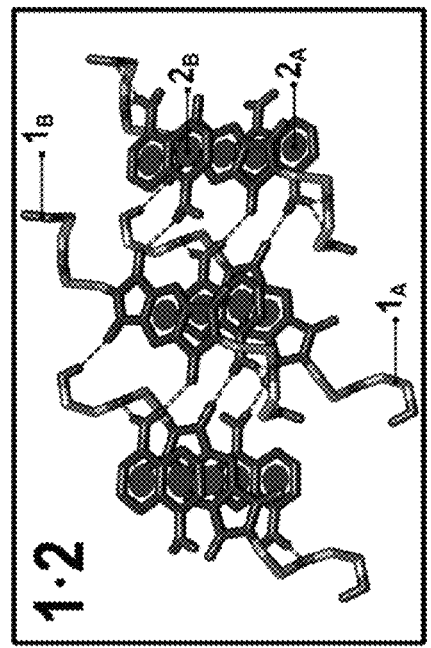
FIGS. 6a-d (a) molecular structures of electron donor (1α) and electron acceptor (9β, 10β and 12β) molecules; (b) co-crystal 1α•9β belonging to the P1 space group with unit cell spacings of 9.5063(4) Å, 12.1715(6) Å, and 12.8872(6) Å, and two unique DA pairs ($1α_A•9β_A$, $1α_B•9β_B$) with spacings of 3.25 Å and 3.26 Å between the closest C—C contact; (c) co-crystal 1α•10β belongs to the Pn space group with unit cell spacings of 6.9937(2) Å, 11.8675(2) Å, and 17.5154(3) Å; the co-crystal has a C—C distance of 3.30 Å for the closest contact; (d) co-crystal 1α•12β has a $P2_1$ space group with unit cell spacings of 11.909(6) Å, 6.959(3) Å, and 16.711(7) Å, and a C—C spacing of 3.48 Å for the closest contact in the DA dimer.
Figure 6B:
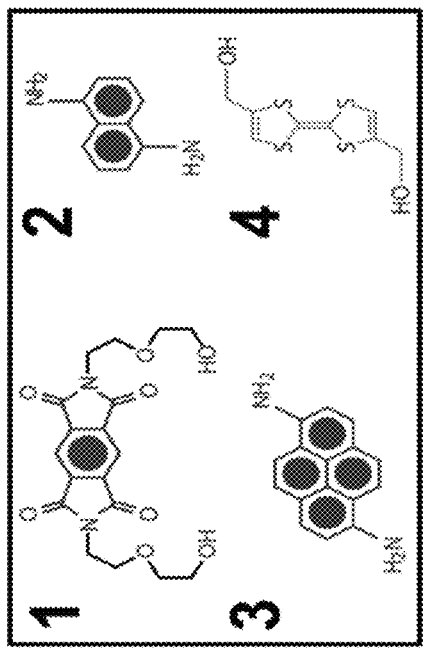
Figure 6C:
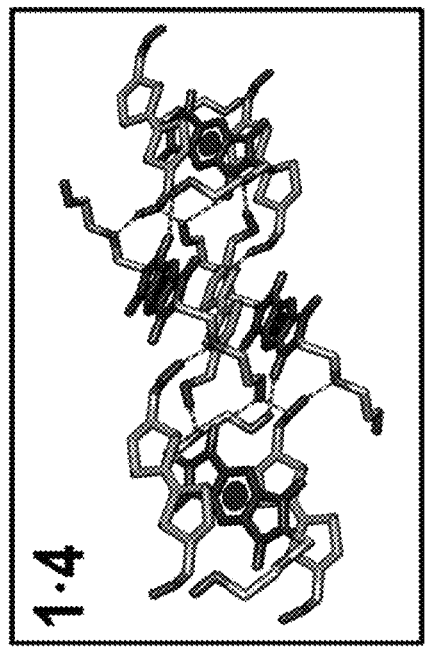
Figure 6D:
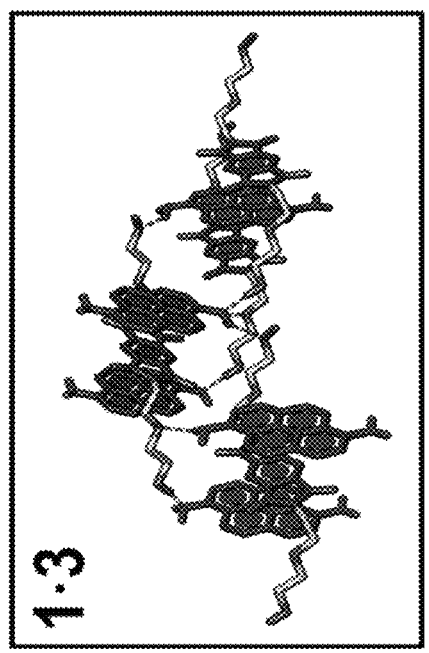
Figures 7A, 7B, 7C:
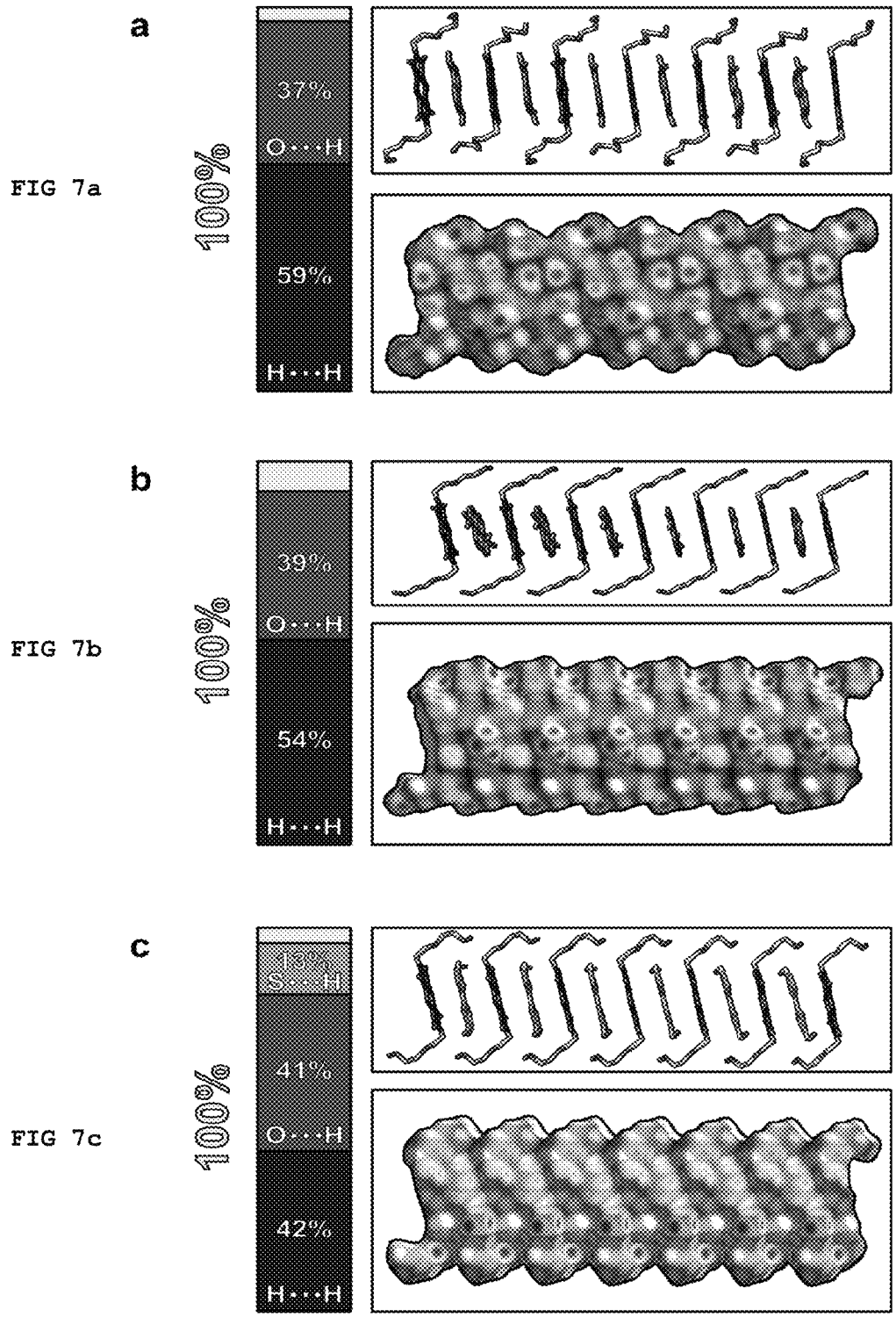
FIGS. 7a-c provide noncovalent connectivity diagrams through Hirshfeld surface analysis of (a) co-crystal 1α•9β; (b) co-crystal 1α•10β; and (c) co-crystal 1α•12β.

Turning to the ferroelectric behavior of specific embodiments, the CT crystals disclosed herein are based on complexes between donors that are, for example, derivatives of a pyromellitic diimide-based acceptor (FIG. 6a). These CT pairs are co-crystallised (FIG. 8a-8c) under ambient conditions and the resulting solid state structures characterized by X-ray crystallography (FIG. 6b-6d). The basic structural details for each lattice are summarized in Table 2. In these networks, the assembly of the acceptor 1α and donor (9β, 10β, 12β) components in the lattice are stabilized by four primary supramolecular interactions: (i) charge transfer (CT), (ii) hydrogen bonding, (iii) π-π stacking, and (iv) van der Waals forces. Diimide 1α is functionalized with diethylene glycol arms that are capable of acting as both hydrogen bond donors and acceptors. Electron-rich compounds 9β, 10β, 12β can also interact through hydrogen bonding since their shorter arms are terminated by hydroxyl or amino groups. An extensive hydrogen bonded network comprised of interstack and intrastack hydrogen bonds (FIG. 6b-6d) is formed during the self-assembly process. This LASO enables complementary molecules to crystallize rapidly into functional networks from solution under ambient conditions (FIG. 7a-7c). The overall motif for LASO structures requires a hierarchical organization based on noncovalent bonding interactions that bridge distances from Angstroms to nanometers and are considerably stronger than van der Waals forces. Locally, the CT and n-n stacking interactions are directed along a single dimension parallel to the mixed stack axis, while the hydrogen bonds extend into three dimensions. This panoply of supramolecular interactions leads to a tightly packed network of mixed stacks locked over larger length scales by hydrogen bonds, π-π stacking, and CT.

TABLE 2

|  | 1α9β | 1α10β | 1α12β |
| --- | --- | --- | --- |
| formula | $C_{28}H_{30}N_4O_8$ | $C_{34}H_{32}N_4O_8$ | $C_{26}H_{28}N_2O_{10}S_4$ |
| M | 550.56 | 624.64 | 656.77 |
| Crystal system | triclinic | monoclinic | monoclinic |
| Space Group | P1 | Pn | P2$_1$ |
| a (Å) | 9.5063 (4) | 6.9937 (2) | 11.9236 (4) |
| b (Å) | 12.1715 (6) | 11.8675 (2) | 6.9553 (3) |
| c (Å) | 12.8872 (6) | 17.5154 (3) | 16.7123 (5) |
| α (deg.) | 61.896 (3) | 90.00 | 90.00 |
| β (deg.) | 89.095 (3) | 100.896 (1) | 104.157 (2) |
| γ (deg.) | 76.689 (3) | 90.00 | 90.00 |
| V (Å$^3$) | 1272.50 (1) | 1427.53 (5) | 1343.89 (8) |
| Z | 2 | 2 | 2 |
| T (K) | 84 | 100 | 85 |

In order to illustrate the connectivity of the hydrogen bonded network in the interstitial regions between the stacks, Hirshfeld surface analysis (McKinnon, J. J., et al. *Acta Crystallogr., Sect. B: Struct. Sci* 2004, 60, 627-668, incorporated herein by reference) is used to measure the distribution of close contact interactions (FIG. 7). The Hirshfeld surface is a graphical tool that compares the atomically averaged electron density of a molecule to the electron density of the entire crystal and partitions the lattice into molecular surfaces which map the spatial contacts. In FIG. 7, white regions represent molecular contacts at the van der Waals distance, while grey and black portions represent lengths shorter and longer than the van der Waals distance, respectively. This type of analysis helps identify which interactions are the most dominant among neighbouring stacks. The bar graphs show that [O . . . H] interactions responsible for hydrogen bonding make up 37-41% of all interstack contacts while [H . . . H] interactions are 42-50% of such contacts, revealing the close packed nature of the structure (FIG. 7). The lengths shorter than van der Waals are significant because they arise from short [O . . . H] and [H . . . H] distances when interstack hydrogen bonds are formed. These interstack interactions are between neighboring arms and allow the stacks to pack tightly into a supramolecular network.

Since the electron transfer occurs along the stacking axis, ionicity (ρ), the extent of CT, is characterized to investigate how its magnitude affects ferroelectric behavior. Polarized vibrational spectroscopy (FT-IR) is used to determine ρ for each compound. The ungerade modes are used to calculate ρ because they are not influenced by electron-molecular vibration interactions. At room temperature, ρ for 1α9β, 1α10β, and 1α12β is determined by following the linear shift of the C=O stretch (1728-1716 cm$^{-1}$) polarized parallel to the DA stack. Compounds 1α9β and 1α10β are measured to be ionic with ρ=0.68 and 0.89 (see Table 3 below), respectively, while 1α12β lies close to the neutral-ionic border (ρ=0.5) with ρ=0.43. Therefore, the polar nature of the crystal enables the LASO network to be ferroelectric. Along with significant electron transfer, a violation of the mutual exclusion rule between the IR and Raman modes exists in all three systems at 300° K, indicating a non-centrosymmetric lattice. This behavior in mixed stack crystals, comprised of symmetric molecules, demonstrates that LASO networks fulfill the requirements for a ferroelectric system, namely, DA dimerization and a polar lattice.

Figure 9A:
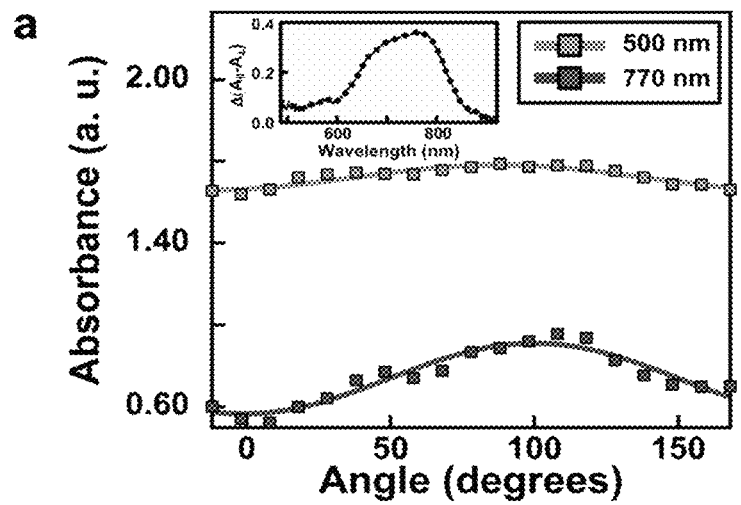
FIGS. 9a-c provide linear dichroism of the LASO networks for (a) co-crystal 1α•9β; (b) co-crystal 1α•10β; and (c) co-crystal 1α•12β.
Figure 9B:
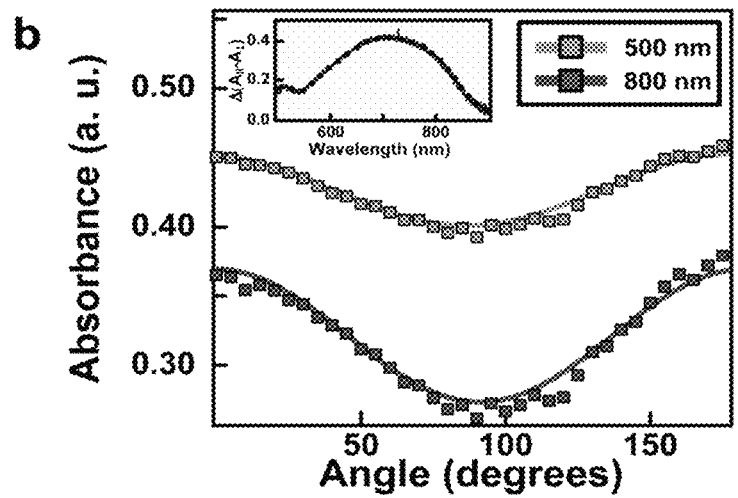
Figure 9C:
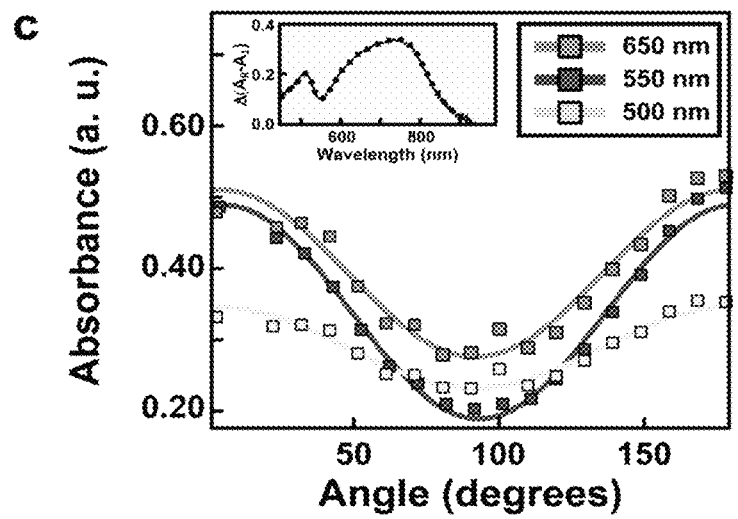

Polarized UV-Vis transmission spectroscopy (Kuwatago-nokami, M. et al. *Nature* 1994, 367, 47-48, incorporated herein by reference) (FIG. 9a-9c) and polarized optical microscopy (FIG. 8d-8f) are employed to elucidate the anisotropy of the CT in LASO networks with regard to the crystal axis. When the linear polarization of white light is oriented parallel to the polar mixed stack (long axis), the system absorbs intensely. Conversely, when the polarization is oriented perpendicular to the stack axis, there is a clear lack of color. The absorbance bands (FIG. 9a-9c) associated with this color change shows a maximum in absorbance when the polarization is aligned with the direction of the stacks for 1α9β, 1α10β, and 1α12β. These transitions (FIG. 9a-9c, inset) located between 1.38-1.50 eV (800-900 nm) are attributed to the lowest intra-dimer CT exciton state (Meneghetti, M., et al. *J. Chem. Phys.* 1996, 105, 397-407, incorporated herein by reference) ($DA^{\delta+}A^{\delta-}\square\,[D^{\delta+}A^{\delta-}]^*$). Based on this pronounced dichroism, it is possible to establish unequivocally that the polar axis of the material is aligned with the long axis of the crystal.

Figure 38:
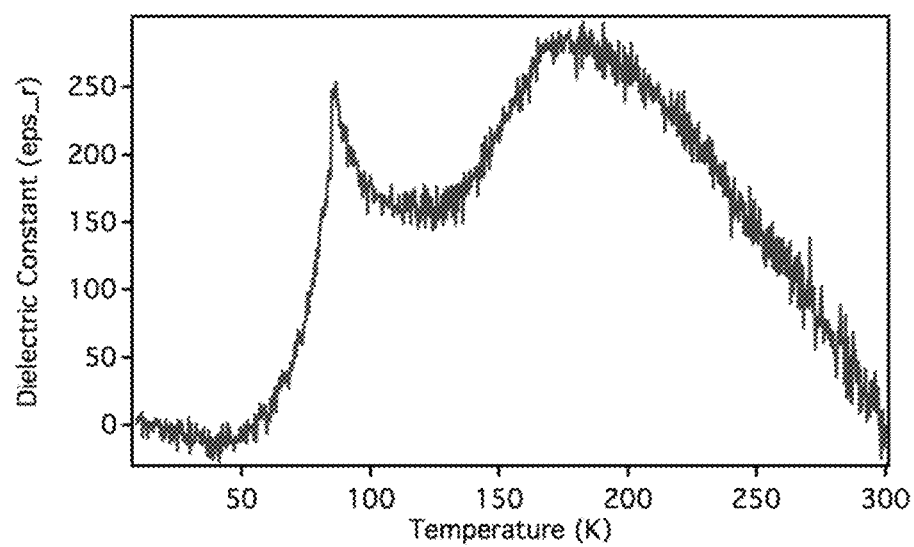
FIG. 38 is a graph of the temperature dependent dielectric constant of TTF-CA (control).

To determine the ferroelectric Curie temperature of each structure, the dielectric constant ($\in_r$) is measured as a function of temperature along the ferroelectric axis. For co-crystals 1α9β, 1α10β, and 1α12β, no characteristic discontinuity is observed between 5° K and 400° K (FIG. 10a-10c). These results suggest that the ferroelectric phase exists at room temperature, an observation which is consistent with spectroscopic and crystallographic evidence. The temperature dependent dielectric constant measurements are performed on TTF-CA as a control (FIG. 38). This measurement shows a $T_c$ of 84° K, consistent with previously reported studies of ferroelectric phase transitions. Further evidence for room temperature ferroelectricity is obtained by measuring hysteresis curves of electric displacement versus electric field (D-E) along the ferroelectric axis (FIGS. 11a, 11c, and 11f). Polarization hysteresis curves for co-crystal 1α9β are measured at 300° K (FIG. 11a) and 74° K (FIG. 11b). Polarization hysteresis curves for complex 1α10β are measured at 300° K (FIGS. 11c and 11d) and at 7° K (FIG. 11e). Polarization hysteresis curves are measured for complex 1α12β at 300° K (FIG. 11f) and 7° K (FIG. 11g). Room temperature hysteresis curves for LASO complexes are underpolarized because of leakage currents at high voltage. Ferroelectric network 1α10β shows hysteresis similar to 1α9β and 1α12β at small electric fields (FIG. 11d). At larger electric fields, 1α10β demonstrates larger hysteresis loops (FIG. 11c). The unexpectedly large remnant polarisation in 1α12β observed at low temperatures is attributed to a combination of charge transfer exchange and proton dynamics within the lattice. Hysteresis curve measurements are performed at f=0.1 Hz for FIGS. 11a-e, g, and f=1 Hz for FIG. 11f. Polarization hysteresis of co-crystals 1α9β, 1α10β, and 1α12β are observed at 300° K with remnant polarizations ($P_r$) exceeding 1 μC/cm$^2$. Attempts to observe saturation by applying higher electric fields results in dielectric breakdown and crystal melting. Larger polarization hysteresis loops are obtained at lower temperatures down to 7° K where leakage currents are minimized (FIGS. 11b, 11d, 11e and 11g). At low temperature, D-E curves for co-crystal 1α12β are unexpectedly large. Surprisingly, the $P_r$ for this network is found to be approximately 55 $\mu C/cm^2$, much larger than compound 1α9β or 1α10β. This large polarization can result from the combination of the CT process and proton dynamics within the crystal (Horiuchi, S., et al. *Nature Mater.* 2008, 7, 357-366 and Horiuchi, S., et al. *Nature* 2010, 463, 789-797, both incorporated herein by reference). The $P_r$ of 1α11β at 7° K is among the highest reported for organic ferroelectrics based on charge transfer, hydrogen bonding, liquid crystalline or polymeric materials. The resistivity of all LASO systems investigated, however, is found to be very high (>$10^9$ Ω/cm) at room temperature.

The ferroelectric curves obtained at room temperature are biased at a lower electric field compared to cryogenic temperatures. At high electric fields at room temperature, dielectric leakage and joule heating prevents the measurement of saturating polarization hysteresis loops. Curves measured at 300° K are obtained by applying a smaller electric field than required for saturation. As a result, these systems are inherently under-polarized and have smaller remnant polarizations than saturated loops.

Larger hysteresis loops are obtained in compound 1α10β (FIG. 11d) at room temperature because this network is able to withstand higher voltages. It is interesting to note that this hydrogen bonded network has a higher ionicity (ρ~0.89) than co-crystals 1α9β or 1α12β. The only CT ferroelectric that demonstrates polarization bistability is TTF-BA with a $T_c$ of 53° K. TTF-BA also has a very large ionicity with ρ~0.9, similar to 1α10β. As pointed out by Torrance, J. B. *Accounts of Chemical Research* 1979, 12, 79-86, incorporated herein by reference, high ionicities inhibit current flow in CT crystals because of Coulombic interactions. Negative and positive ions in a lattice can behave as ionic impurities that actively scatter moving electrons. Network 1α10β and TTF-BA have large ionicities and may therefore mitigate leakage current to some degree. In this context, developing networks of CT complexes with large ionicities may be a useful design rule for ferroelectricity at room temperature and above.

Ferroelectric networks 1α9β and 1α12β are characterized by SQUID magnetometry and revealed magnetic hysteresis loops. Extensive elemental analysis described in detail below shows that any magnetic impurities present have to be below the detection limit of currently available instruments for inductively coupled plasma atomic emission spectroscopy (ICP-AES). Other measurements (Magnetic Force Microscopy) described below attempt to verify ferromagnetic behavior.

Materials and Methods

All compounds are purchased from commercial vendors (Sigma Aldrich and VWR) and are used as supplied without further purification. For the synthesis of 1α, 2α, 5α, 6α, and 12β see: Bevers, S., et al. *J. Am. Chem. Soc.* 2000, 122, 5905-5915; Sue, C. H., et al. *Chem Sci* 2010, 1, 119-125; Asakawa, M., et al. *Journal of Organic Chemistry* 1996, 61, 9591-9595; and Saha, S., et al. *Chem. Eur. J.* 2005, 11, 6846-6858, all incorporated herein by reference.

Figure 2A:
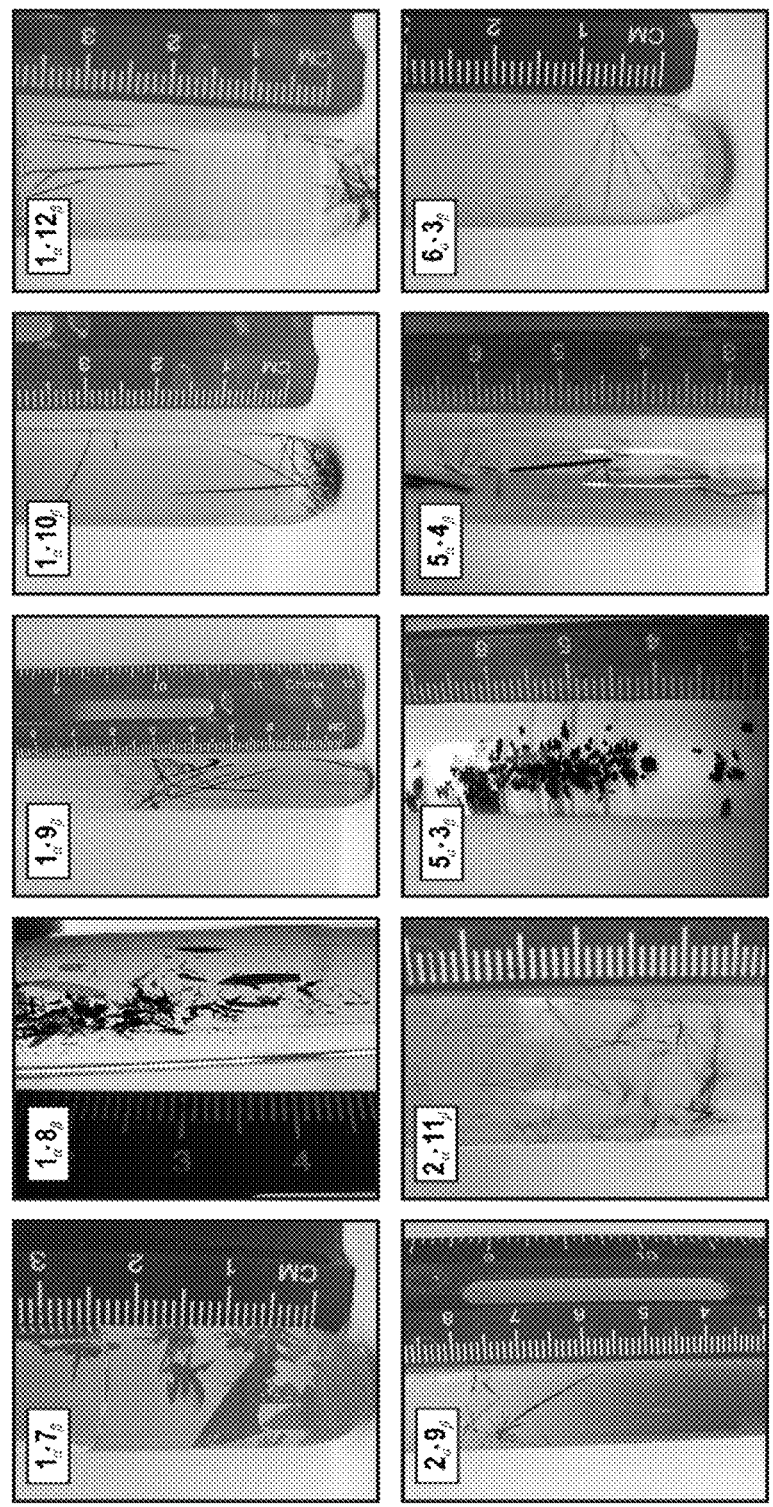
FIGS. 2a-c provide images of the crystal morphology for ten LASO crystals and the experimental controls for the crystallization; (a) ten LASO co-crystals grown from four α-complements and eight β-complements; (b) image taken after 5 days showing the co-crystals of 1α•9β grown by diffusion 1-chlorobutane into 1,2-dichloroethane/diethyl ether, contaminated with traces of $H_2O$; (c) image shows experimental controls for the co-crystallizations grown to show that α'-arm and β-arms are essential for self-assembly of LASO materials.

All the crystals are grown in the dark, under ambient conditions using liquid diffusion. Two distinct solvent systems are found to promote expedient crystal growth. The molar ratio α:β and the total concentration of α+β are optimized to achieve the best crystal size and growth rate (Table 1). The eight co-crystals which do not contain 3β (pyromellitic diimide) are grown from liquid diffusion of anhydrous non-protic solvents 1-chlorobutane into a 1,2-dichloroethane and diethyl ether mixture (FIG. 2a and FIG. 3). As $H_2O$ is found to disrupt the self-assembly of these eight co-crystals, anhydrous conditions for the materials and solvents are ensured before the crystals are grown. Owing to the insolubility of 3β in common organic solvents, a different type of solvent combination is used for the two complexes containing β. The liquid diffusion of protic $H_2O$ into polar N-methylpyrrolidone is found to produce the most pronounced crystal growth. EG/SiC samples are produced in a UHV chamber with a base pressure below $1\times10^{-10}$ Torr unless otherwise noted. The SiC is resistively heated by passing current through the SiC while temperatures are monitored using an optical pyrometer (Cyclops) at an emissivity of 0.85. The SiC is degassed overnight at 600° C. and then annealed for 2 minutes at 1000° C. The SiC is then flashed 3 times at 1100° C. for 2 minutes each. After each flash, the sample is allowed to cool for 10 minutes. Finally, the SiC is graphitized at 1300° C. for 2 flashes and then 10 flashes at 1350° C. for 1 minute apiece.

Figure 12A:
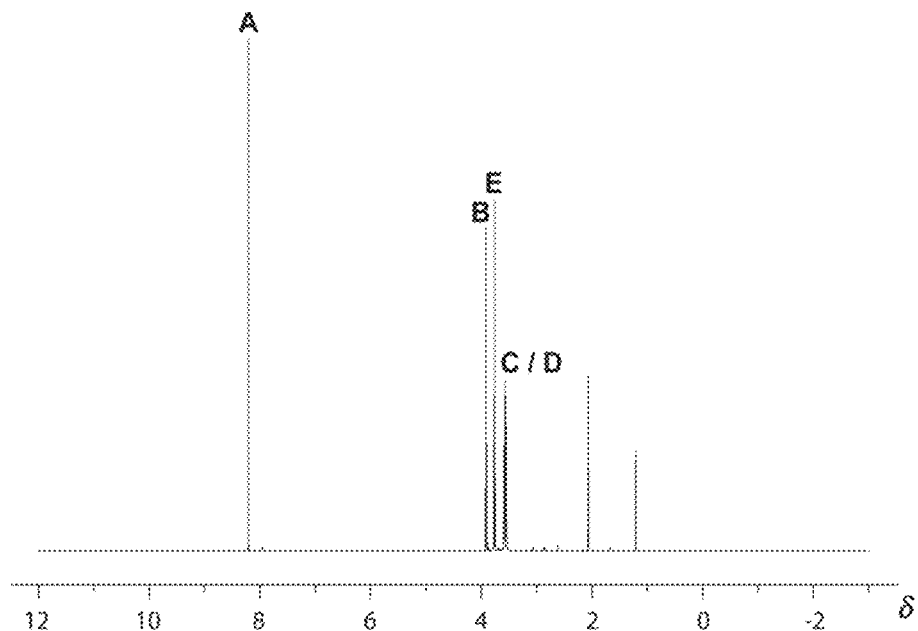
FIGS. 12a-b are (a) a $^1H$ NMR spectrum of 1α recorded at 25° C. in $CD_3COCD_3$ and (b) a $^{13}C$ NMR spectrum of 1α recorded at 25° C. in $CD_3COCD_3$.
Figure 12B:
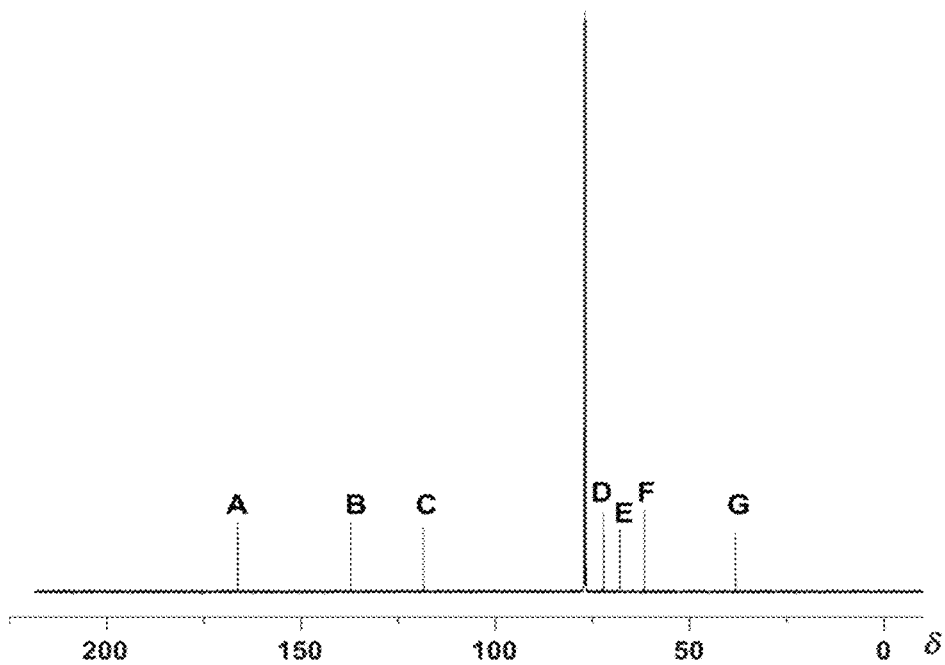
Figure 13:
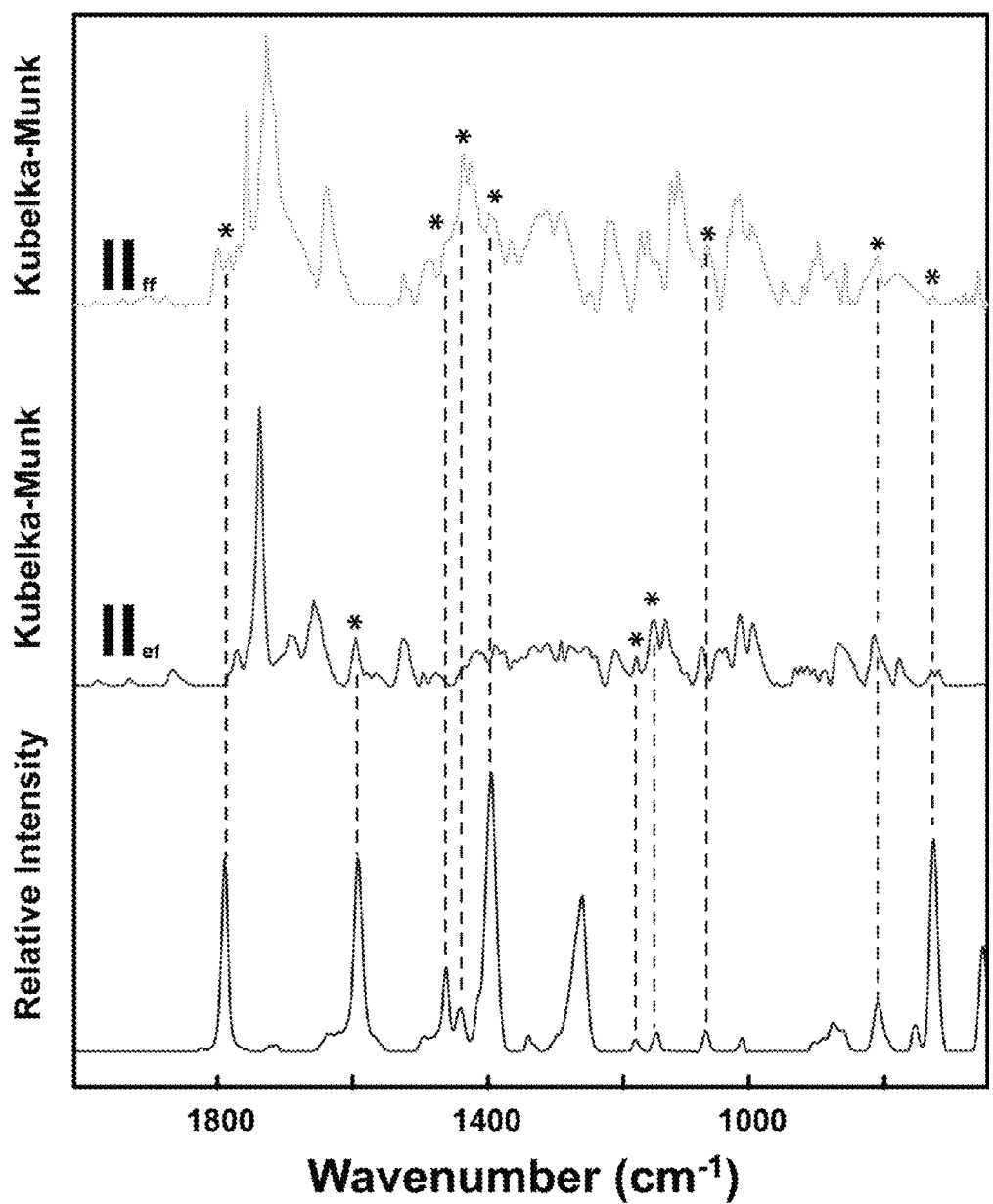
FIG. 13 is a polarized vibrational spectra (300° K) of the co-crystal 1α•7β showing coincident Raman and IR modes.
Figure 14:
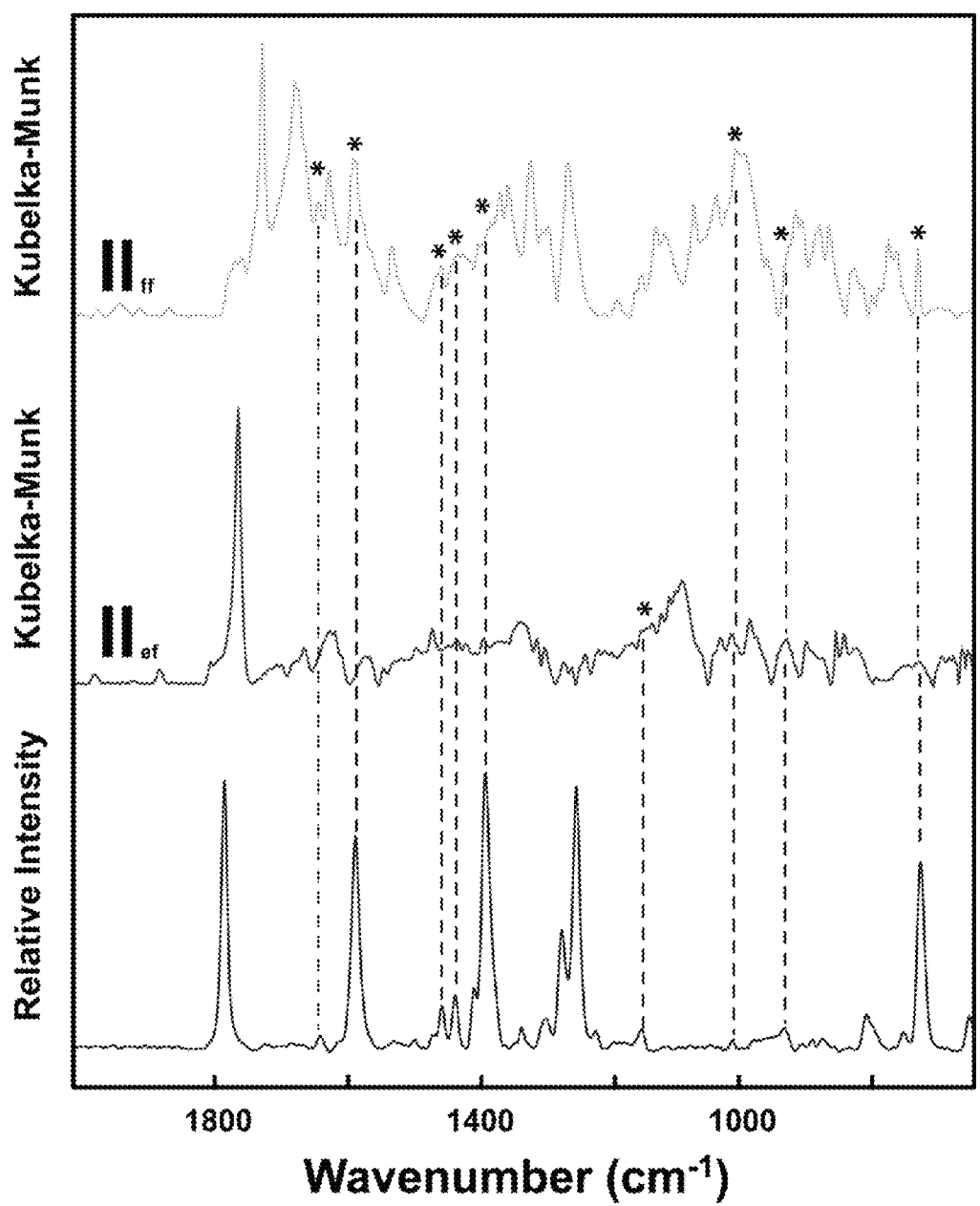
FIG. 14 is a polarized vibrational spectra (300° K) of the co-crystal 1α•8β showing coincident Raman and IR modes.
Figure 15:
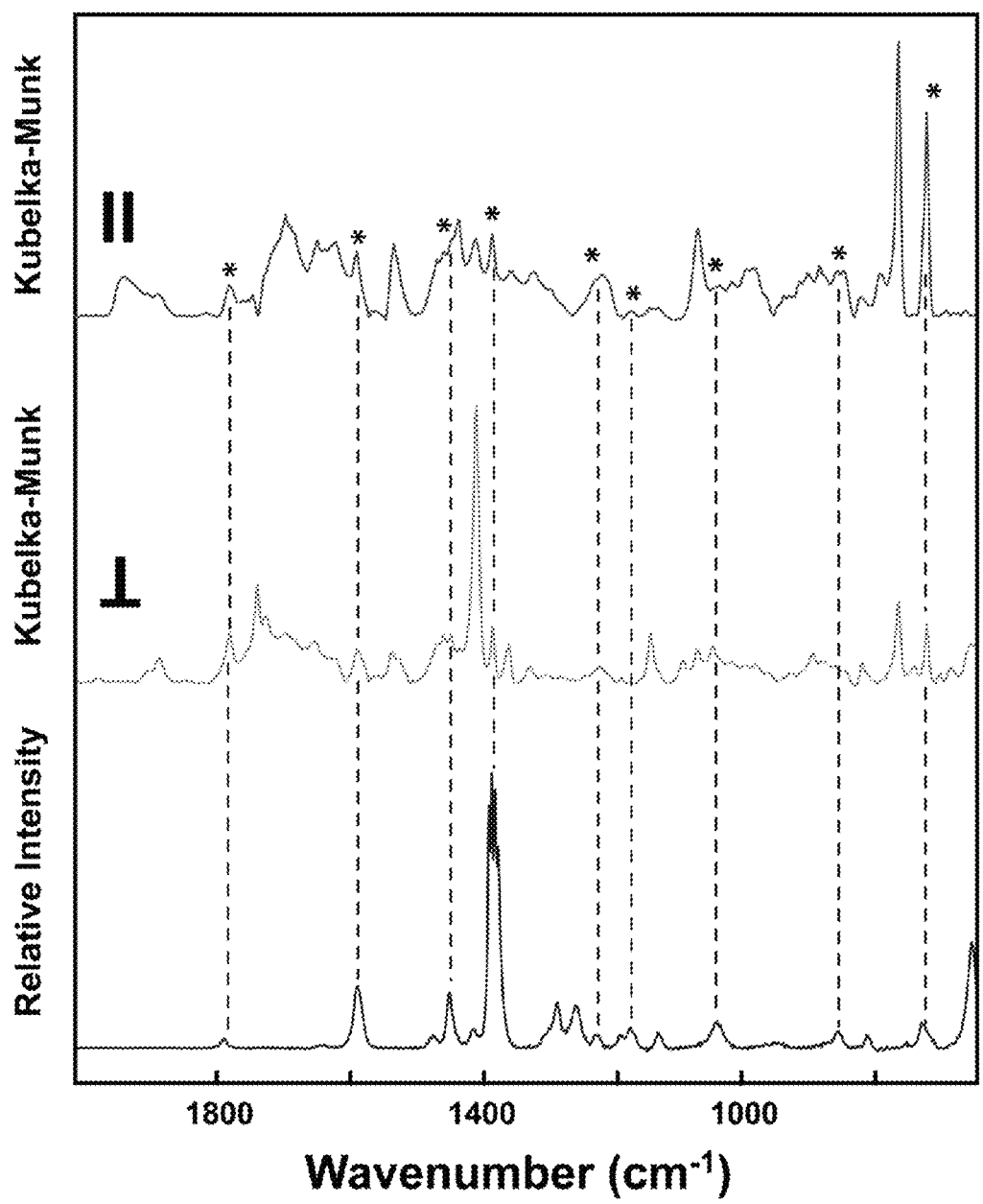
FIG. 15 is a polarized vibrational spectra (300° K) of the co-crystal 1α•9β showing coincident Raman and IR modes.
Figure 16:
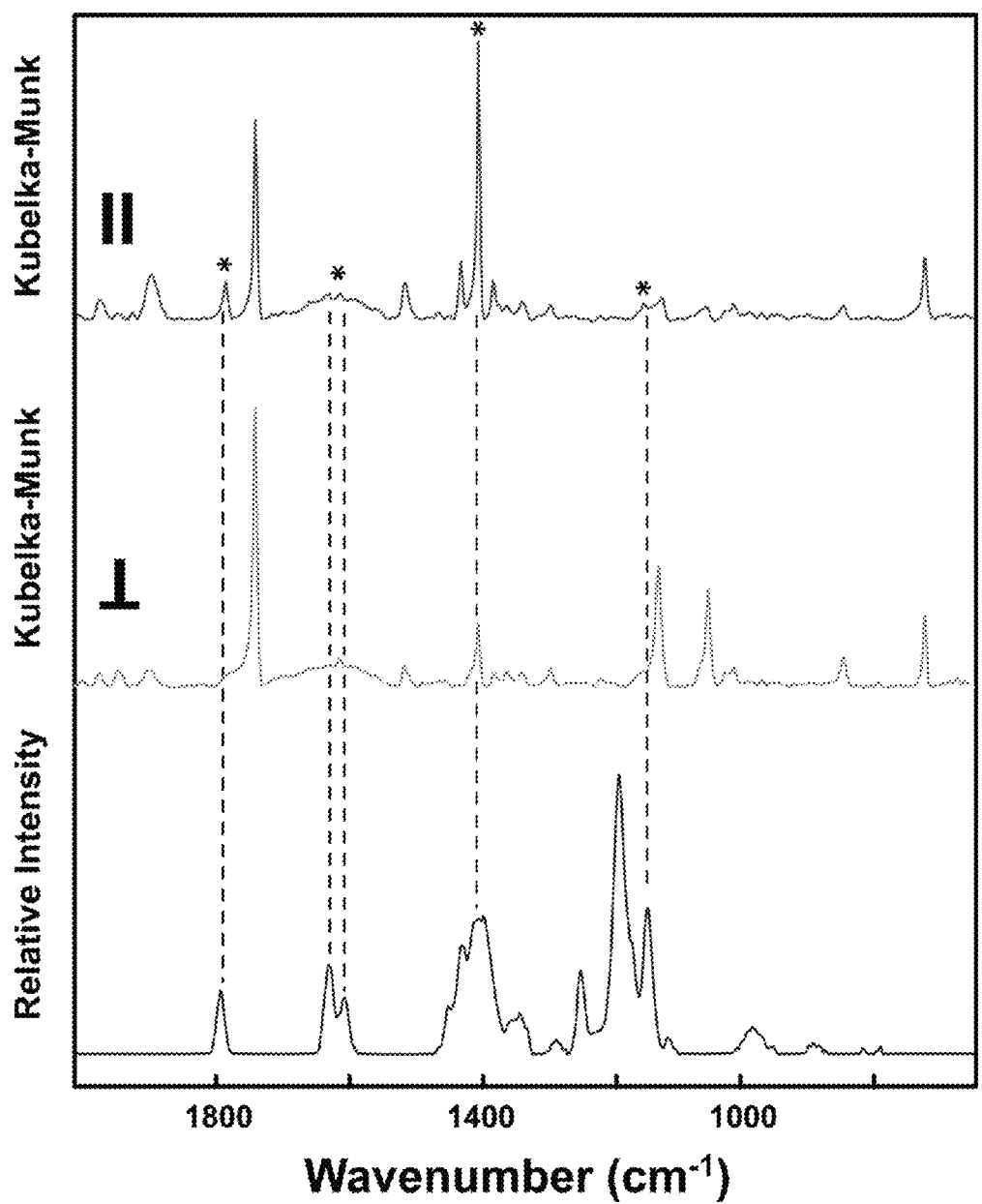
FIG. 16 is a polarized vibrational spectra (300° K) of the co-crystal 1α•10β showing coincident Raman and IR modes.
Figure 17:
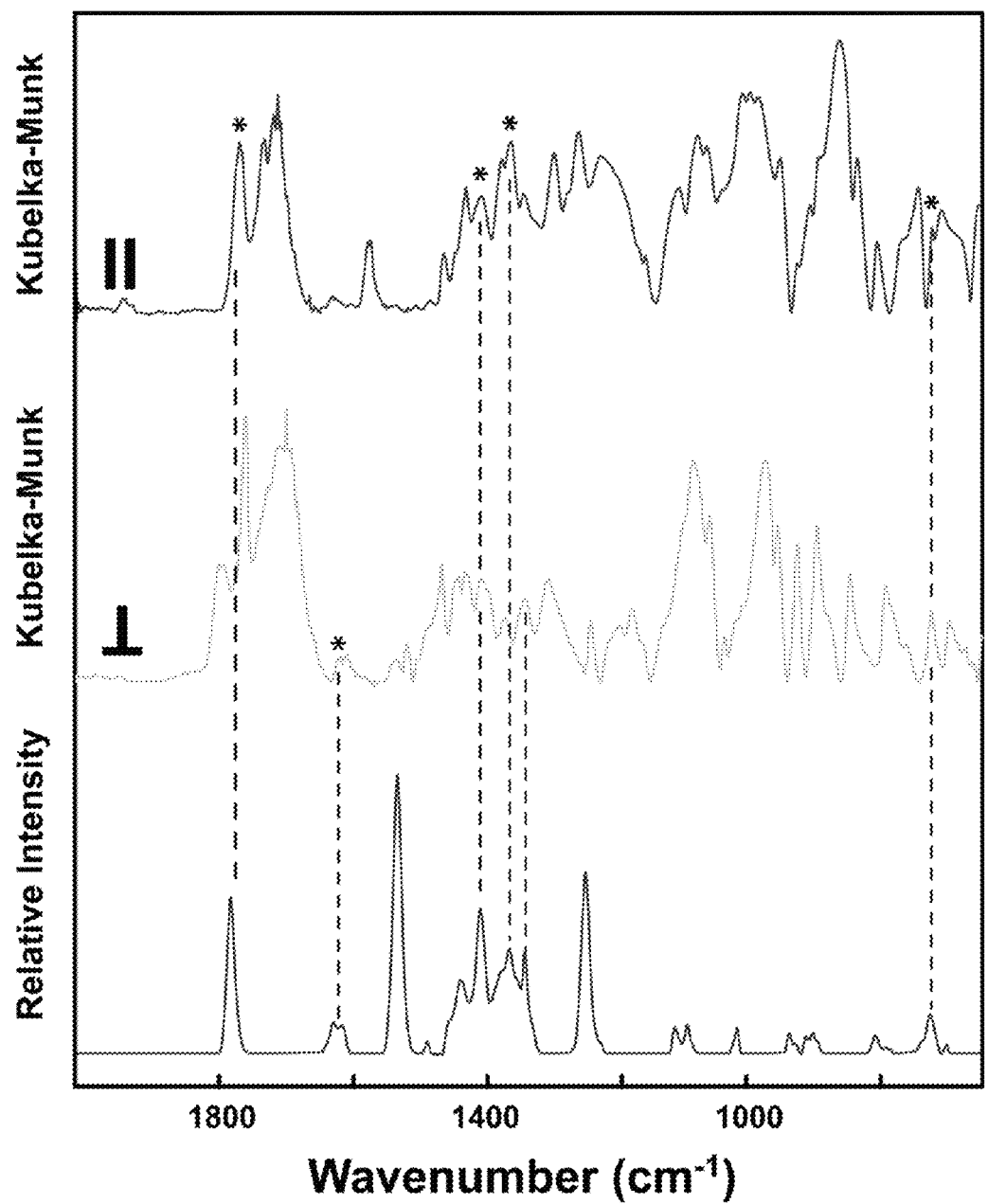
FIG. 17 is a polarized vibrational spectra (300° K) of the co-crystal 1α•12β showing coincident Raman and IR modes.
Figure 18:
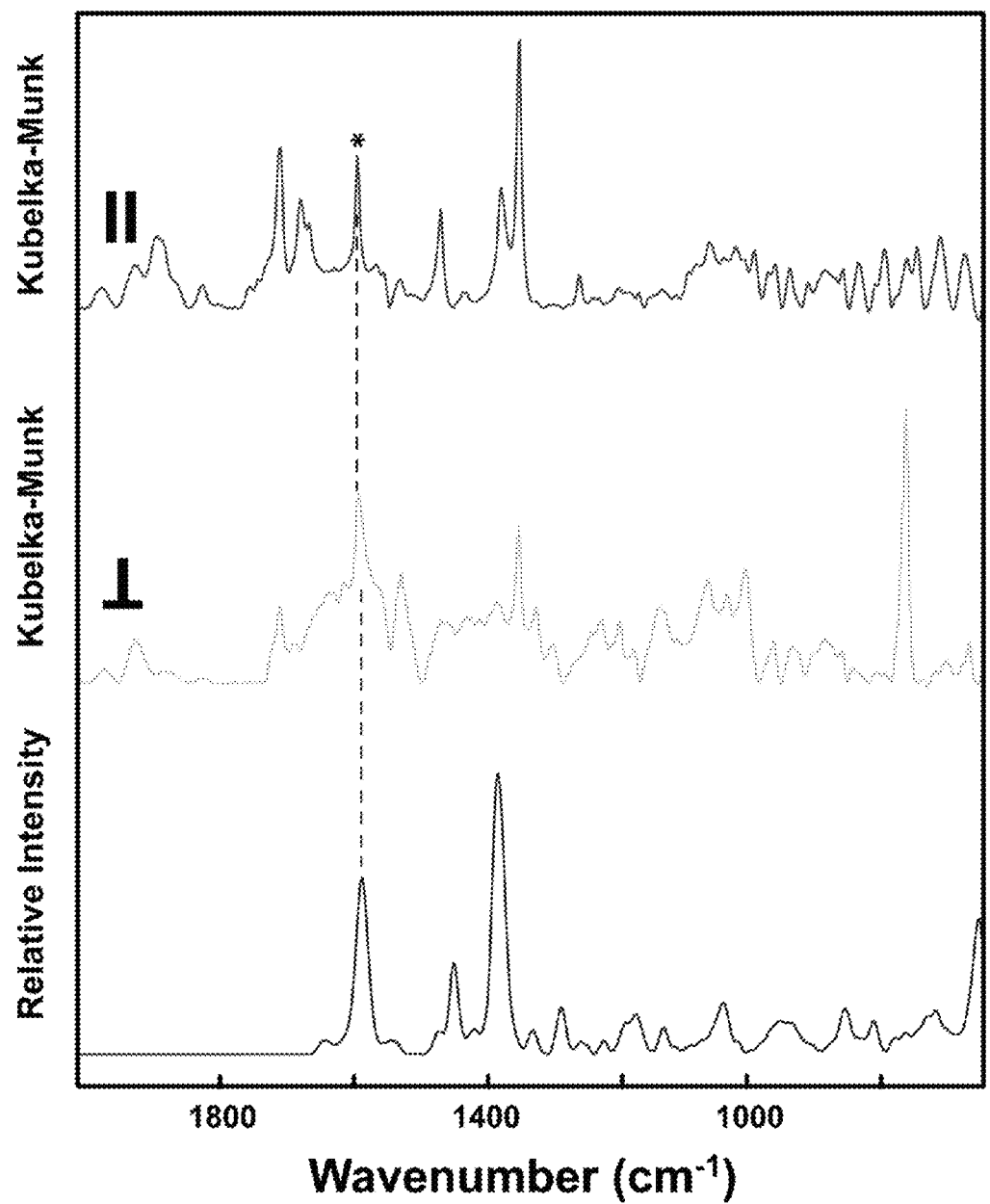
FIG. 18 is a polarized vibrational spectra (300° K) of the co-crystal 2α•9β showing coincident Raman and IR modes.
Figure 19:
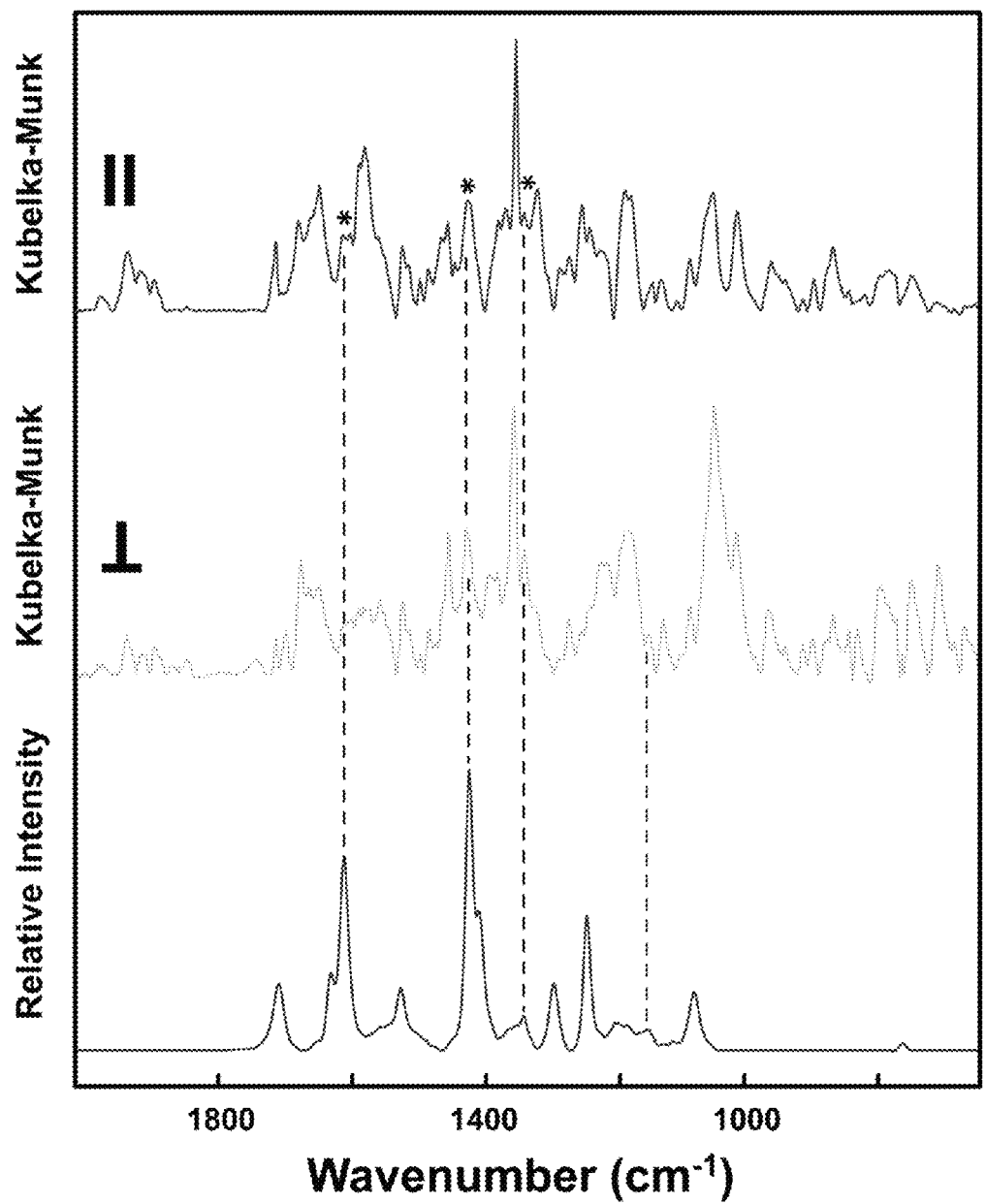
FIG. 19 is a polarized vibrational spectra (300° K) of the co-crystal 2α•11β showing coincident Raman and IR modes.
Figure 20:
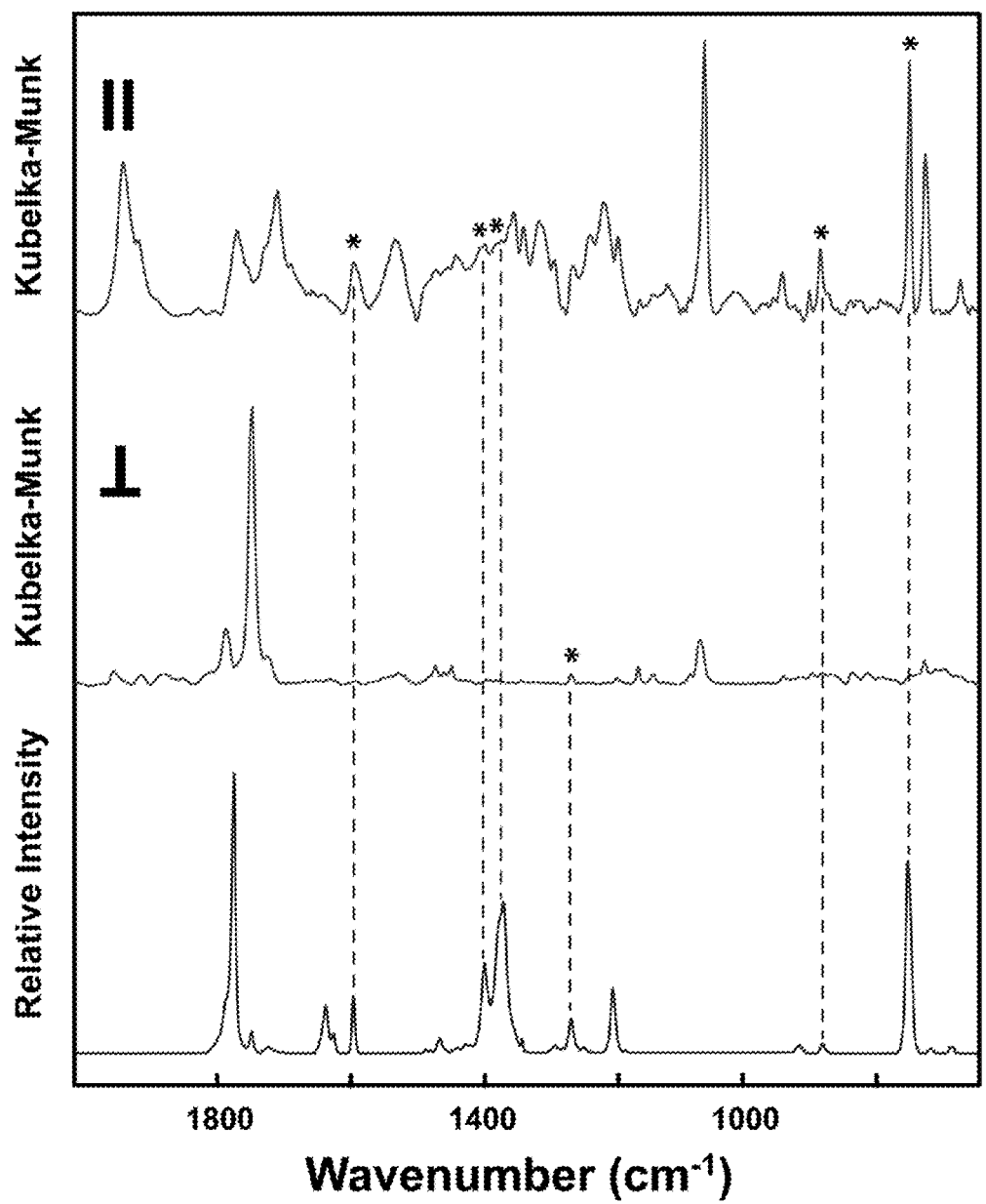
FIG. 20 is a polarized vibrational spectra (300° K) of the co-crystal 5α•3β showing coincident Raman and IR modes.
Figure 21:
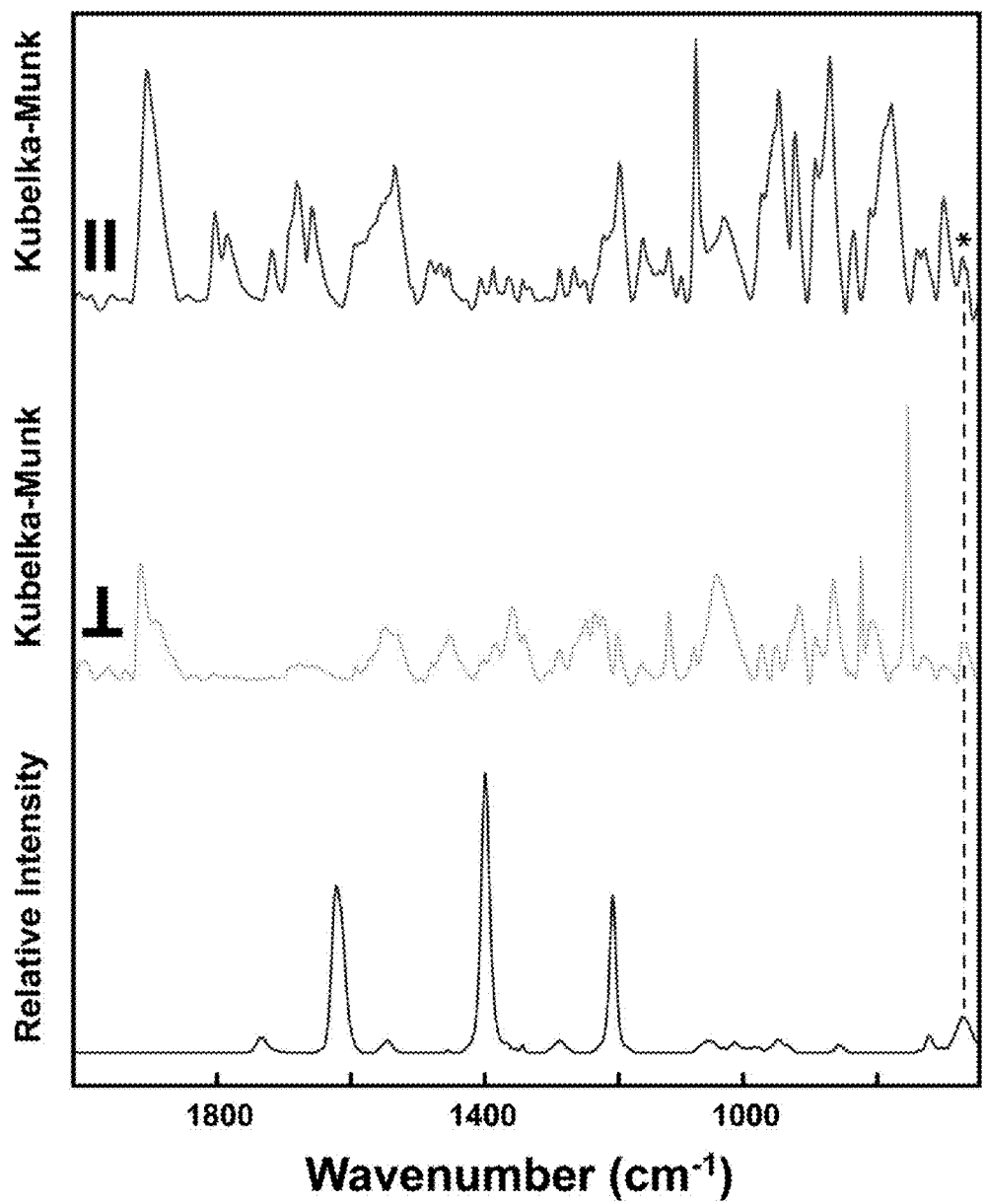
FIG. 21 is a polarized vibrational spectra (300° K) of the co-crystal 5α•4β showing coincident Raman and IR modes.

Thin layer chromatography (TLC) is performed on silica gel 60 F254 (E. Merck). Nuclear magnetic resonance (NMR) spectra are recorded at 25° C. on Varian Inova 500 spectrometers, with working frequencies of 500 MHz for $^1H$, and 125 MHz for $^{13}C$ nuclei (see FIG. 12a and FIG. 12b for $^1H$ and $^{13}C$ NMR, respectively, of 1α). The chemical shifts are listed in ppm on the δ scale and coupling constants are recorded in Hertz (Hz). The following abbreviations are used to explain the multiplicities: s, singlet; d, doublet; t, triplet; b, broad peaks; m, multiplet or overlapping peaks. High resolution electrospray ionization (HR ESI) mass spectra are measured on a Micromass Q-TOF Ultima mass spectrometer. All FT-IR spectra are collected by a Perkin Elmer Spectrum Spotlight Imaging System utilizing liquid nitrogen cooled single element mercury-cadmium-telluride detector in single-point reflectance mode with an aperture setting of 50×50 $\mu m^2$. The sample is presented as a single crystal placed on a Si plate. Raman spectra are obtained with either an Advantage 532 Raman Spectrometer using a 532 nm excitation line or a 633 nm HeNe laser (Research Electro-Optics Inc.) that collects the scattered light into a spectrograph (PI Acton SP2500i) equipped with a 600 g/mm grating blazed at 750 nm and a liquid-$N_2$ cooled CCD detector. Polarization of the HeNe laser is achieved using an adjustable air spaced achromatic half-wave waveplate (CVI Melles Griot ACWP-400-700-10-2). A baseline correction is performed to allow for interpretation of the spectra. Single crystals of the complexes are mounted in oil (InfineumV8512) on a glass fiber under a nitrogen cold stream at 83(2)° K. X-Ray diffraction data are collected on a Bruker Kappa diffractometer, equipped with a CuKα or MoKα sealed-tubesource and an APEX II CCD detector. Data are collected, integrated and corrected for decay and Lp effects using BrukerAPEX II software. Final unit cell parameters are obtained through a refinement of all observed reflections during data integration. A multi-scan absorption correction is performed using SADABS. The structures are solved and refined using the SHELXTL suite of software. The absorption spectra are taken using a polarization microscopy setup. A Nikon TE2000 inverted microscope and Prior ProScan II stage are used to manipulate the sample position. The microscope halogen lamp is used as the source for the absorption spectra. Spectra are recorded using an Ocean Optics USB 2000 miniature spectrometer. The polarization dependence is varied using a thin film polariser. Cyclic voltammetry (CV) and square-wave differential pulse voltammetry (SWDPV) experiments are performed at room temperature in argon-purged solutions of N,N'-dimethylformamide (DMF) with a Gamry Multipurpose instrument (Reference 600) interfaced to a PC. The CV and SWDPV experiments in each case are performed using a glassy carbon working electrode (0.071 cm$^2$). The surface of this electrode is polished routinely with 0.05 µm alumina-water slurry on a felt surface immediately before each run. The counter electrode is a Pt coil and the reference electrode is a saturated calomel electrode (SCE) for both CV and SWDPV experiments. The concentration of the sample and supporting electrolyte tetrabutylammonium hexafluorophosphate (TBA•PF$_6$) are $1.0 \times 10^{-3}$ mol·L$^{-1}$ and 0.1 mol·L$^{-1}$, respectively. The scan rate for CV experiments is set to 200 mV·s$^{-1}$. Experimental errors: potential values, ±10 mV for CV and ±1 for SWDPV.

Ferroelectric structures are mechanically robust and can be handled with vacuum tweezers. Gold wire electrodes (12.5 µm) are attached on either end using gold paint (Ted Pella Gold Paste). The resulting devices are tested in a QuantumDesign PPMS 6000 under an inert atmosphere. The dielectric constant of LASO complexes is determined by capacitance-voltage measurements at 10 V with a 1, 5, or 10 kHz frequency. These measurements are performed using an Agilent E4980A LCR meter. Polarization hysteresis is measured using a ferroelectric tester at 0.1 Hz or 1 Hz frequency (Radiant Technologies Precision LC with Trek amplifier).

Vibrational spectroscopy data helps elucidate the lattice symmetry of the co-crystals at ambient conditions. Six of the LASO crystals are refined in centrosymmetric space groups. The remaining four co-crystals (1α•9β, 1α•10β, 1α•12β, 5α•3β), however, are found to adopt a non-centrosymmetric lattice. These network solids have the spectroscopic signature of a mixed stack crystal that has undergone a polar phase transition where the donors and acceptors have dimerized (D$^0$ A$^0$ D$^0$ A$^0$ □ D$^{+\rho}$A$^{-\rho}$ D$^{+\rho}$A$^{-\rho}$) along the charge transfer (CT) axis.

Employing IR and Raman spectroscopic techniques, the details of the ground state for a CT crystal are experimentally accessible (See FIGS. 13-23). In segregated stacks, totally symmetric (ts) modes can be used to measure the value of the ionicity (ρ) for the material (Girlando, A., et al. *Synth. Met.* 2004, 141, 129-138, incorporated herein by reference), but in mixed stack systems the ts modes are perturbed by the electron-molecular vibration interaction (Girlando, A., et al. *J. Chem. Phys.* 1983, 79, 1075-1085, incorporated herein by reference) and are not useful for this purpose. However, because the ts Raman modes of molecules in crystals are subject to the selection rules governed by site symmetry, these bands are good probes for the loss of centrosymmetry. When molecules do not occupy a center of inversion, the ts vibrations can violate the principle of mutual exclusion (Nakamoto, K. *Infrared and Raman Spectra of Inorganic and Coordination Compounds*, 6th ed., Wiley [Oxford Wiley-Blackwell, distributor]: Hoboken, N.J., 2009, incorporated herein by reference) and appear in the IR spectrum. Away from the center of inversion the molecular dipole moment can change with ts vibrations about its equilibrium. In a polar mixed stack system with symmetric molecules, the dimerization of the donor and acceptor breaks the inversion symmetry in the lattice, and the donor and acceptor no longer reside on inversion centers. The ts modes are now capable of producing an asymmetric charge distribution (dipole moment) and strongly coupling to the CT along the stack. As a result, the ts modes are become coincident in their IR and Raman spectra and are strongly polarized in the direction of the CT axis. Most of the co-crystals have some coincident bands (ν(CH$_2$)) in the Raman and IR spectra, but only four (FIG. 5, FIG. 6, FIG. 7 and FIG. 10) of the LASO co-crystals display this spectroscopic signature in regions (ν(C═O), ν(C═C)) that are sensitive to the CT interaction.

Figure 22:
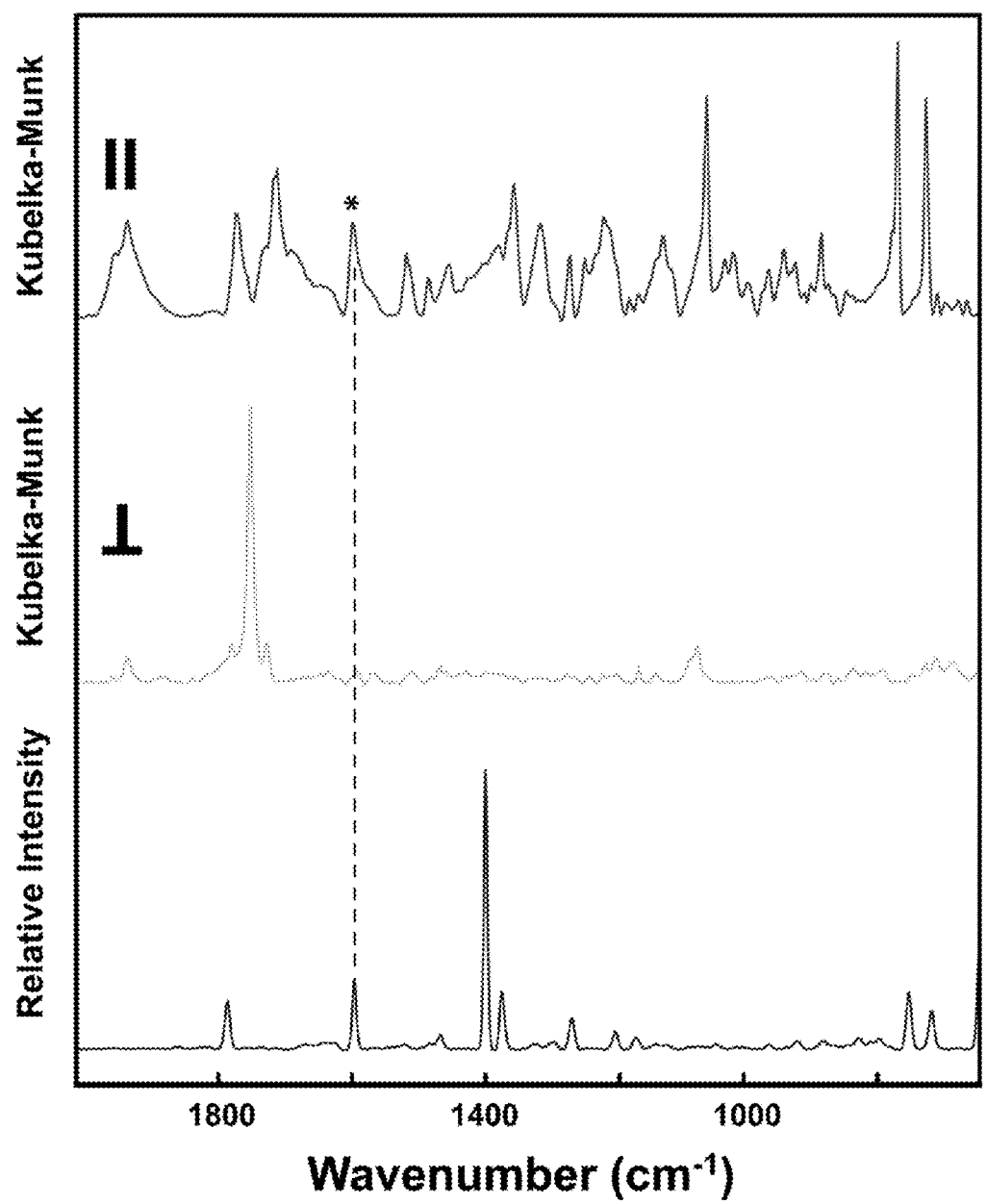
FIG. 22 is a polarized vibrational spectra (300° K) of the co-crystal 6α•3β showing coincident Raman and IR modes.

Referring to FIGS. 13-23, provided are the polarized vibrational spectra (300 K) of co-crystals showing coincident Raman and IR modes. The lowest plot is the unpolarized Raman spectrum. The symbols ∥ and ⊥ indicate linear polarization of the IR radiation with the electric field oriented parallel and perpendicular to the CT stack, respectively. The 1α•7β co-crystal is a crossed stack system (FIG. 13); the 1α•8β co-crystal is a crossed stack system, and the lattice also contains and asymmetric β (FIG. 14); the violation of the rule of mutual exclusion, a spectroscopic signature of dimerization in co-crystal 1α•9β (FIG. 15); the violation of the rule of mutual exclusion, a spectroscopic signature of dimerization in co-crystal 1α•10β (FIG. 16); the violation of the rule of mutual exclusion, a spectroscopic signature of dimerization in co-crystal 1α•12β (FIG. 17); co-crystal 2α•9β shows very few coincident peaks, indicating a lack of dimerization between the donor and acceptor, possibly caused by the positional disorder found in the lattice (FIG. 18); co-crystal 2α•11β contains an asymmetric β that could result in the overlap of modes between the IR and Raman spectra (FIG. 19); the violation of the rule of mutual exclusion, a spectroscopic signature of dimerization in co-crystal 5α•3β (FIG. 20); co-crystal 5α•4β shows very few coincident peaks, indicating a lack of dimerization between the donor and acceptor, possibly caused by the positional disorder found in the lattice (FIG. 21); co-crystal 6α•3β shows very few coincident peaks, indicating a lack of dimerization between the donor and acceptor, possibly caused by the positional disorder found in the lattice (FIG. 22).

Since Girlando, A., et al. *J. Chem. Phys.* 1983, 79, 1075-1085 establishes that the degree of CT (ρ) can be probed through the shifts of ungerade fundamental modes in the vibrational spectra, IR spectroscopy is used extensively for this purpose. Ungerade modes are the best choice for determining ρ, because the shift is not affected by electron-phonon coupling. As long as the crystal is not close to the Curie temperature of a phase transition, the relationship between the shifts in these modes and changes in p are nearly linear. Linear interpolation between the peak positions of the neutral and fully charged molecular species—donor or acceptor—yields a reliable estimate of ρ.

Figure 23A:
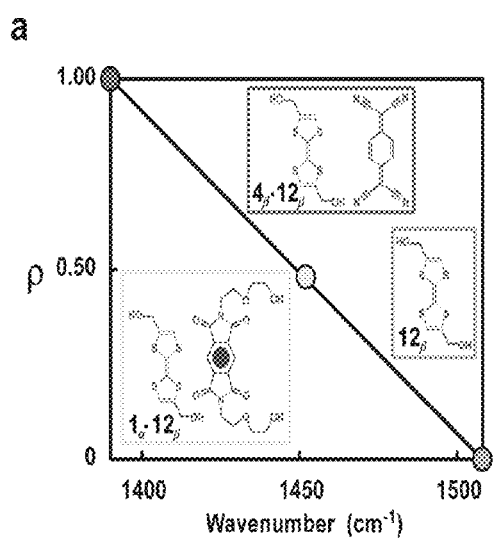
FIGS. 23a-b provide linear graphs used to determine the ionicity based on the shifting of the ungerade modes in the IR spectra; (a) follows the shift of ν (C=C) for $12_\beta$; (b) follows the shift of ν (C≡N) for $4_\beta$.
Figure 23B:
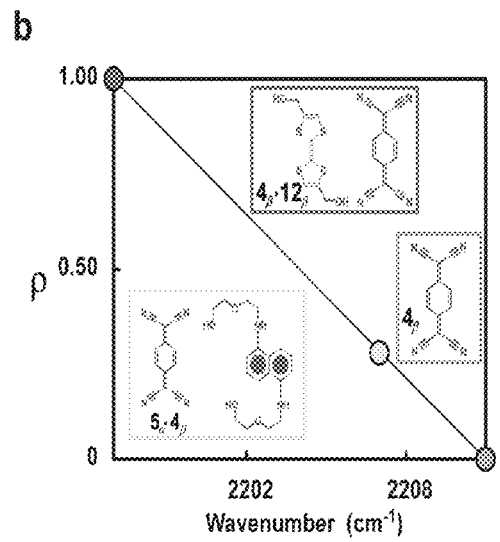
Figure 24:
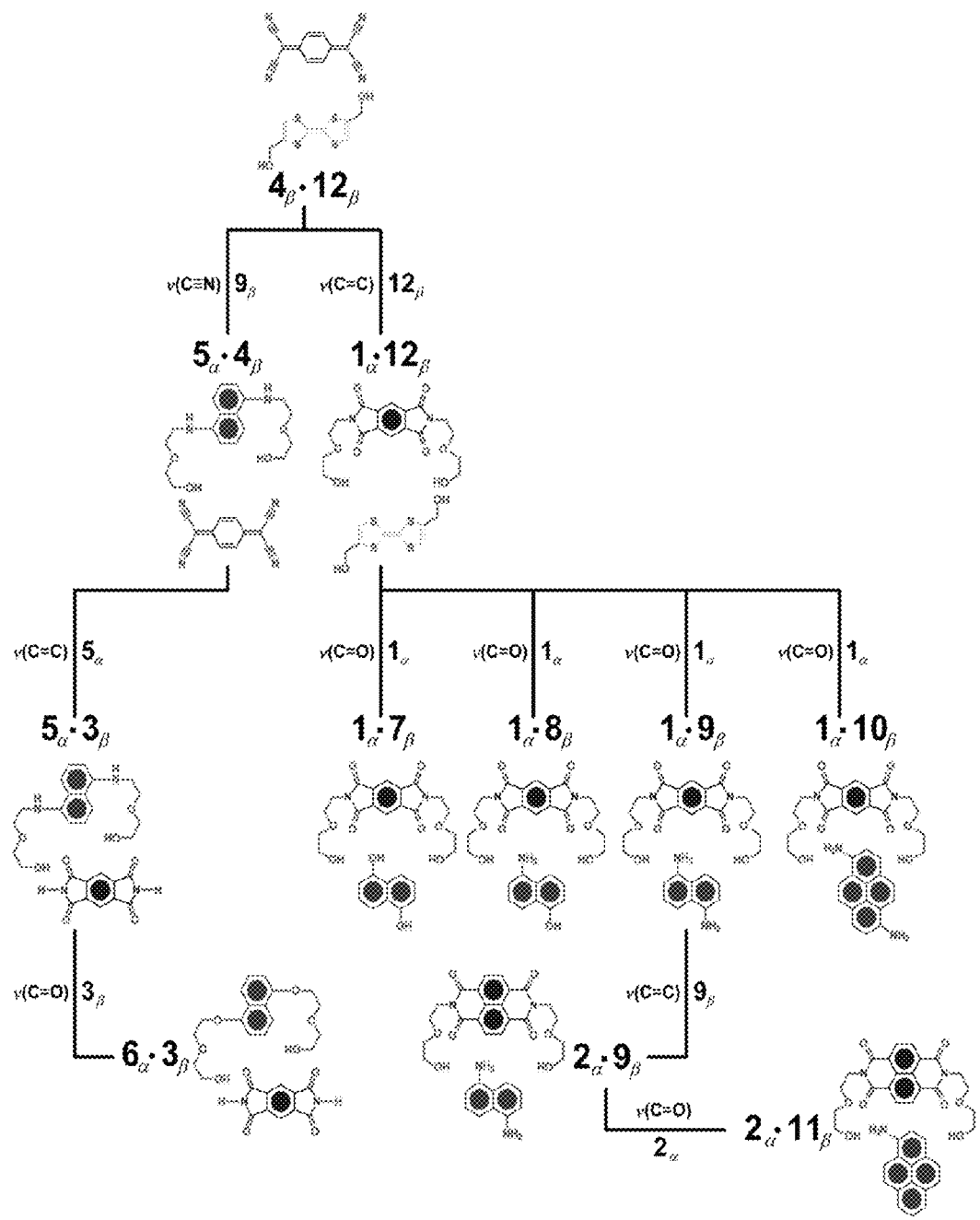
FIG. 24 is a flow chart illustrating IR modes used to determine ρ for the LASO co-crystals.
Figure 36A:
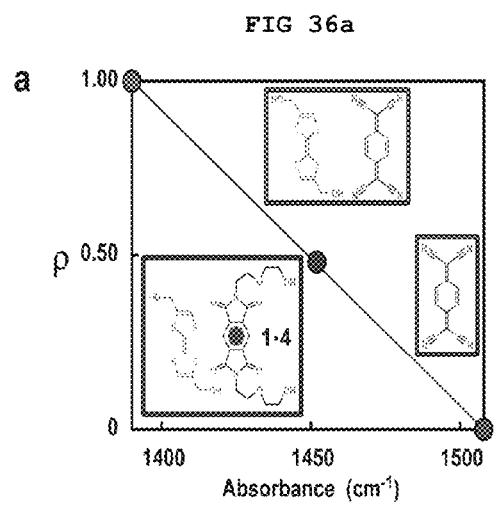
FIGS. 36a-b provide linear graphs used to determine the ionicity based on the shifting of the ungerade modes in the IR spectra; (a) small crystals of complex TCNQ•10β grown and ρ for this complex used as a reference to estimate the ionicity of the remaining co-crystals; (b) ionicity for 1α•9β, 1α•10β and 1α•12β determined to be 0.67, 89, and 0.43, respectively.
Figure 36B:
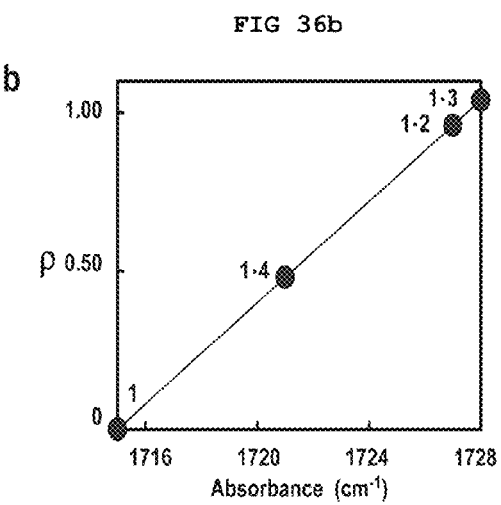

To determine ρ in the LASO co-crystals, a method based on the linear shifting of the ungerade modes is also used (FIG. 23 and FIG. 36). However, a complex between 4β (tetracyanoquinodimethane, TCNQ) and the tetrathiafulvalene (TTF) derivative 12β is grown and used as a reference to estimate ρ for the rest of the LASO crystals. The affect of CT interactions on the vibrational spectra of TCNQ are well understood (Bozio, R., et al. *J. Chem. Soc., Faraday Trans. II* 1978, 74, 235-248; and Meneghetti, M., et al. *J. Chem. Phys.* 1985, 83, 3134-3145, incorporated herein by reference) and the ionicity of a co-crystal can be determined by using the shift of the ν(C≡N) mode (FIG. 23b). This procedure is used to estimate ρ for TCNQ•4 (FIG. 23a and FIG. 36a), ρ=1.0. In the IR spectra of the LASO co-crystals, it is found that the ν (C═O) mode in 1α is sensitive to changes in ρ (Horiuchi, S., et al. *Nat. Mater.* 2005, 4, 163-166, incorporated herein by reference). Using extrapolation in the plot of ρ vs. ν (C═O) of 1α and 1α12β (FIG. 36b), the ionicity of 1α9β and 1α10β is determined to be ρ=0.68 and ρ=0.89, respectively. FIG. 24 is a flow chart illustrating which IR modes are used to determine ρ for the LASO co-crystals described herein. FIG. 25 contains linear graphs used to determine the ionicity based on shifting the ungerade modes in the IR spectra. FIG. 25a is a graph that follows the shift of ν (C=O) for 1α; FIG. 25b follows the shift of ν (C=C) for 9β; FIG. 25c follows the shift of ν (C=O) for 2α; and FIG. 25d follows the shift of
ν (C=O) for 3β.

X-ray crystallographic data is obtained for co-crystals and are as follows.

A) 1α•7β: $C_{46}H_{48}N_4O_{18}$, M=472.44, triclinic, a=6.7868 (1), b=10.8904(2), c=15.7778(2) Å, α=70.880(1), β=81.554 (1), γ=83.156(1)°, V=1086.72(3) Å$^3$, T=100(2) K, space group P1, Z=1, ρ=1.44 g·cm$^{-3}$, μ(Mo$_{Kα}$)=0.11 mm$^{-1}$, 10415 independent observed reflections, 6720 reflections with I>2σ(I), $R_{int}$=0.040, R[$F^2$>2σ($F^2$)]=0.052, wR($F^2$)=0.132.

Figure 26:
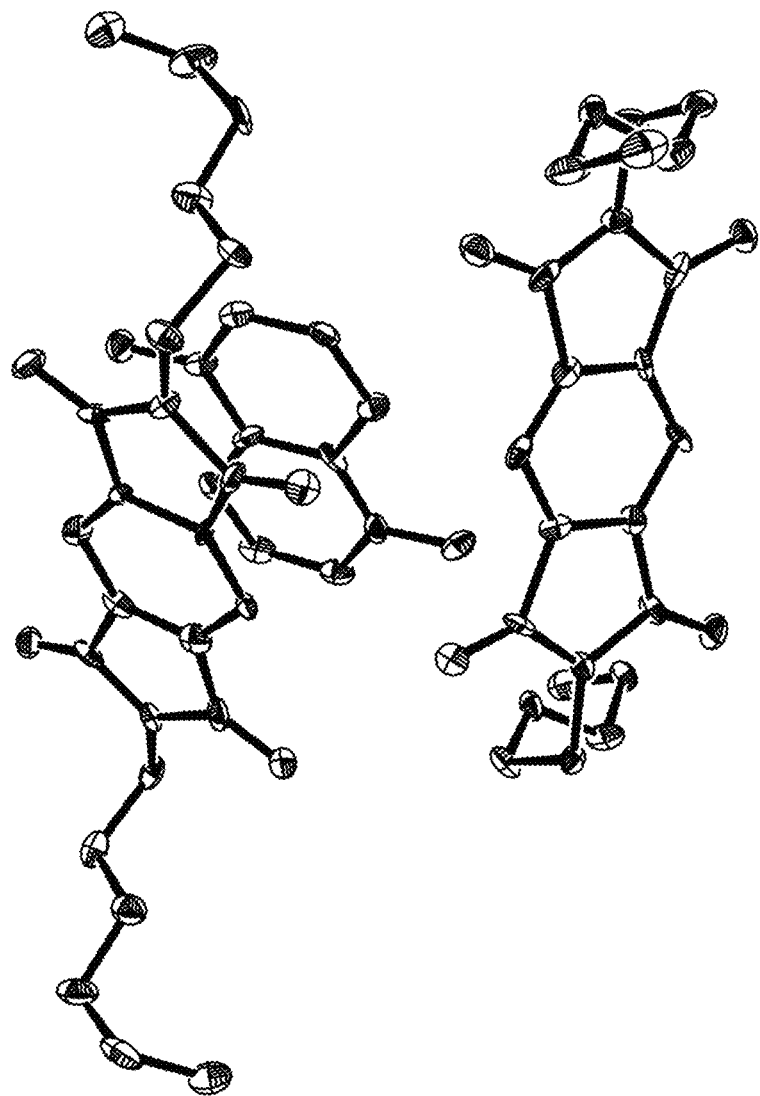
FIG. 26 is an Oak Ridge Thermal Ellipsoid Plot (ORTEP) drawing of 1α•7β.

FIG. 26 is the Oak Ridge Thermal Ellipsoid Plot Program (ORTEP) for co-crystal 1α•7β. The hydrogen atoms are omitted for clarity. This co-crystal is crossed stack. The ratio of the PMDI-based α to the naphthalene-based β is 2:1 acceptor in the unit cell. There is π-face-to-π-face packing and edge-to-π-face packing between the α and β. All ellipsoids are displayed at the 50% probability level.

B) 1α•8β: $C_{46}H_{49}N_5O_{17}$, M=471.95, triclinic, a=6.7603 (7), b=10.8522(11), c=15.785(2) Å, α=71.882(9), β=81.810 (9), γ=84.105(8)°, V=1087.3(2) Å$^3$, T=84(2) K, space group P1, Z=1, ρ=1.44 g·cm$^{-3}$, μ(Mo$_{Kα}$)=0.94 mm$^{-1}$, 4368 independent observed reflections, 3222 reflections with I>2σ(I), $R_{int}$=0.047, R[$F^2$>2σ($F^2$)]=0.051, wR($F^2$)=0.147.

Figure 27:
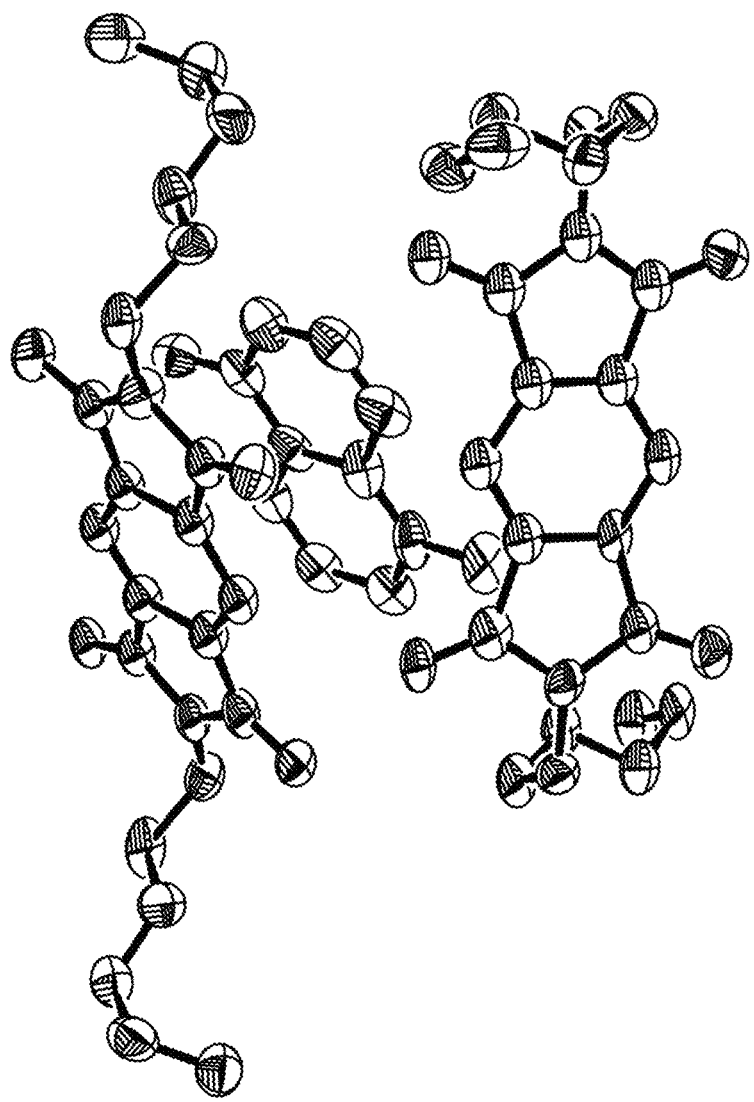
FIG. 27 is an ORTEP drawing of 1α•8β.

FIG. 27 is the ORTEP for co-crystal 1α•8β. The hydrogen atoms are omitted for clarity. Co-crystal 1α•8β is crossed stack. The ratio of the PMDI-based α to the naphthalene-based β is 2:1 acceptor in the unit cell. There is π-face-to-π-face packing and edge-to-π-face packing between the α and β. All ellipsoids are displayed at the 50% probability level.

C) 1α•9β: $C_{28}H_{30}N_4O_8$, M=550.56, triclinic, a=9.5063 (4), b=12.1715(6), c=12.8872(6) Å, α=61.896(3), β=89.095 (3), γ=76.689(3)°, V=1272.50(10) Å$^3$, T=84(2) K, space group P1, Z=2, ρ=1.44 g·cm$^{-3}$, μ(Mo$_{Kα}$)=0.11 mm$^{-1}$, 10748 independent observed reflections, 7435 reflections with I>2σ(I), $R_{int}$=0.038, R[$F^2$>2σ($F^2$)]=0.052, wR($F^2$)=0.146.

Figure 28:
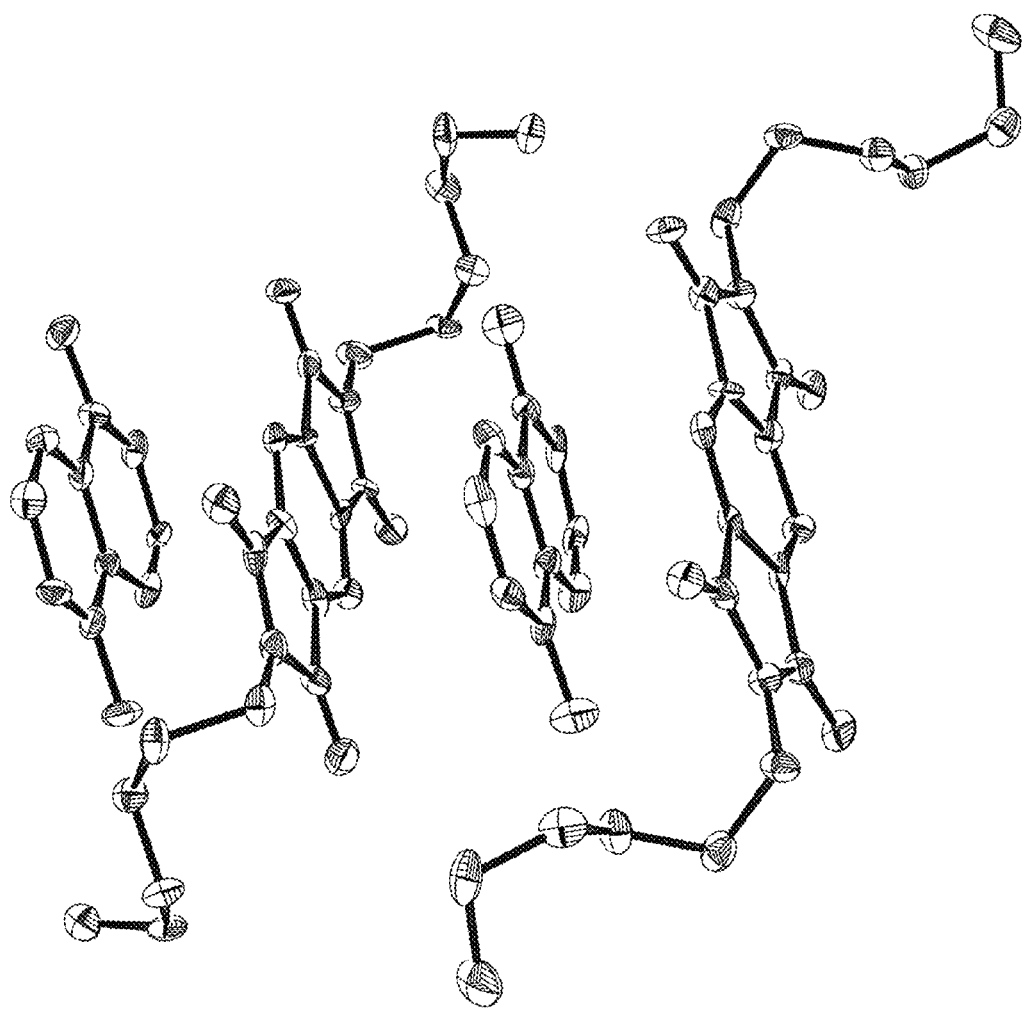
FIG. 28 is an ORTEP drawing of 1α•9β.

FIG. 28 is an ORTEP drawing of co-crystal 1α•9β. The hydrogen atoms are omitted for clarity, co-crystal 1α•9β is crossed stack. The ratio of the PMDI-based α to the naphthalene-based β is 2:1 acceptor in the unit cell. There is π-face-to-π-face packing and edge-to-π-face packing between the α and β. The β is asymmetric with amino and hydroxy arms occupying the 1,5-positions. This asymmetry results in substitutional disorder at the 1,5-positions in the lattice. All ellipsoids are displayed at the 50% probability level.

D) 1$_α$•10$_β$: $C_{34}H_{32}N_4O_8$, M=624.64, monoclinic, a=6.9937(2), b=11.8675(2), c=17.5154(3) Å, β=100.896 (1)°, V=1427.53(5) Å$^3$, T=100(2) K, space group Pn, Z=2, ρ=1.46 g·cm$^{-3}$, μ(CU$_{Kα}$)=0.87 mm$^{-1}$, 3273 independent observed reflections, 2998 reflections with I>2σ(I), $R_{int}$=0.024, R[$F^2$>2σ($F^2$)]=0.048, wR($F^2$)=0.142.

Figure 29:
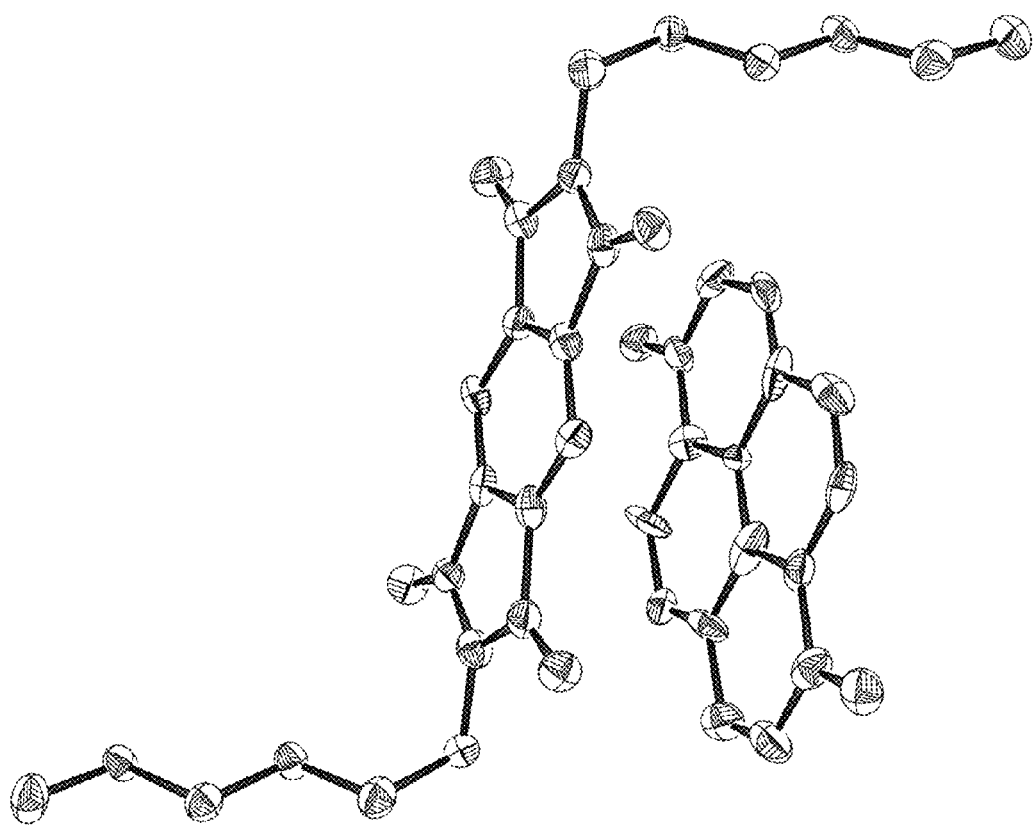
FIG. 29 is an ORTEP drawing of 1α•10β.

FIG. 29 is an ORTEP drawing of co-crystal 1α•10β. The hydrogen atoms are omitted for clarity. Co-crystal 1α•10β is crossed stack. The ratio of the PMDI-based α to the naphthalene-based β is 2:1 acceptor in the unit cell. There is π-face-to-π-face packing and edge-to-π-face packing between the α and β. All ellipsoids are displayed at the 50% probability level.

E) 1α•12β: $C_{26}H_{28}N_2O_{10}S_4$, M=656.74, monoclinic, a=11.9236(4), b=6.9553(3), c=16.7123(5) Å, β=104.227 (4)°, V=1348.26(1) Å$^3$, T=85(2) K, space group P2$_1$, Z=2, ρ=1.62 g·cm$^{-3}$, μ(CU$_{Kα}$)=3.81 mm$^{-1}$, 3213 independent observed reflections, 2680 reflections with I>2σ(I), $R_{int}$=0.040, R[$F^2$>2σ($F^2$)]=0.045, wR($F^2$)=0.130.

Figure 30:
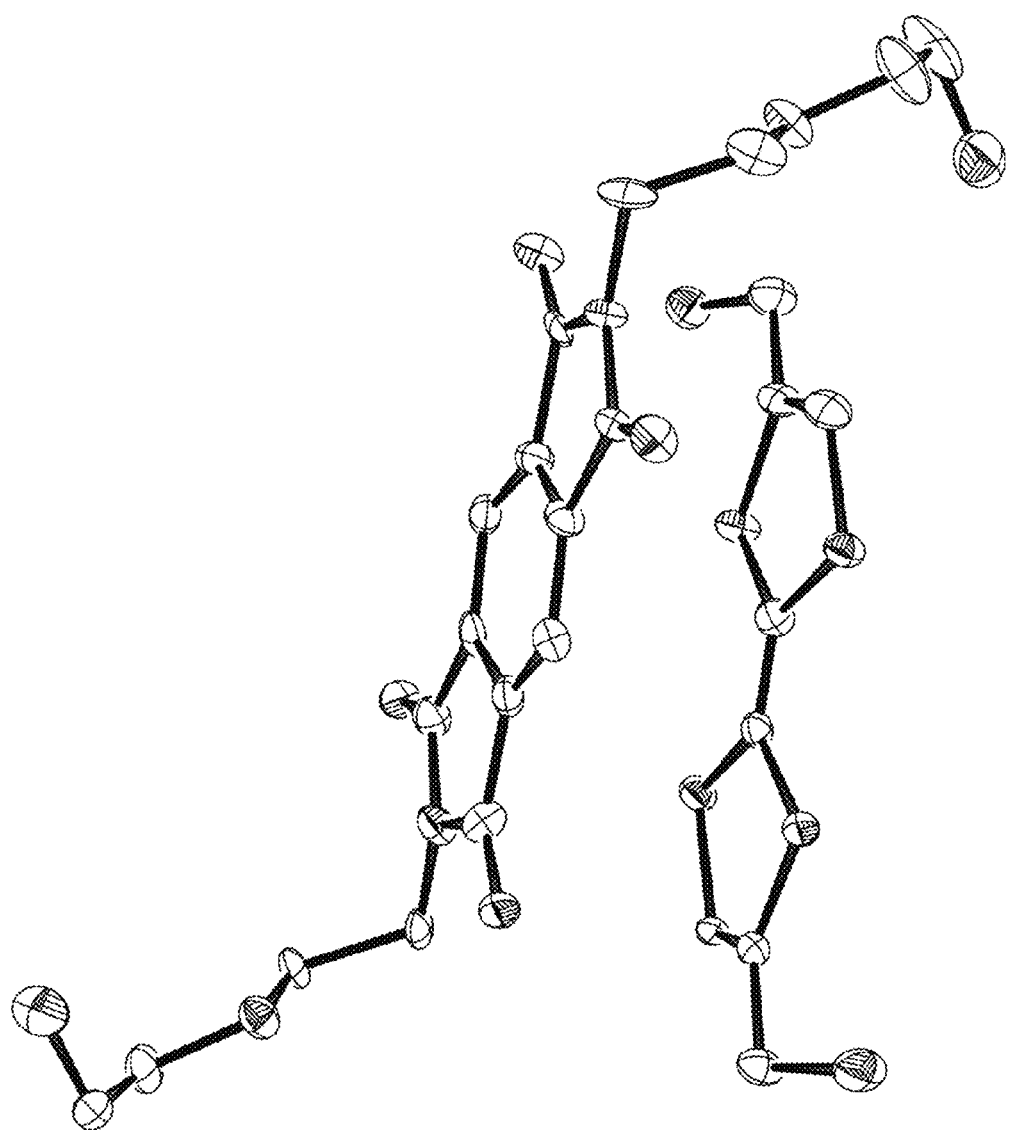
FIG. 30 is an ORTEP drawing of 1α•12β.

FIG. 30 is an ORTEP drawing of co-crystal 1α•12β. The hydrogen atoms are omitted for clarity. There is one TTF-based β and one PMDI-based α in the unit cell. All ellipsoids are displayed at the 50% probability level.

F) 2α•9β: $C_{32}H_{28}N_4O_8$ M=596.58, triclinic, a=6.9510(2), b 8.6966(2), c=12.1281(3) Å, α=72.093(2), β=76.054(2), γ=80.941(2)°, V=674.30(3) Å$^3$, T=100(2) K, space group PI, Z=2, ρ=1.47 g·cm$^{-3}$, μ(Mo$_{Kα}$)=0.11 mm$^{-1}$, 3880 independent observed reflections, 2075 reflections with I>2σ(I), $R_{int}$=0.057, R[$F^2$>2σ($F^2$)]=0.076, wR($F^2$)=0.255.

Figure 31:
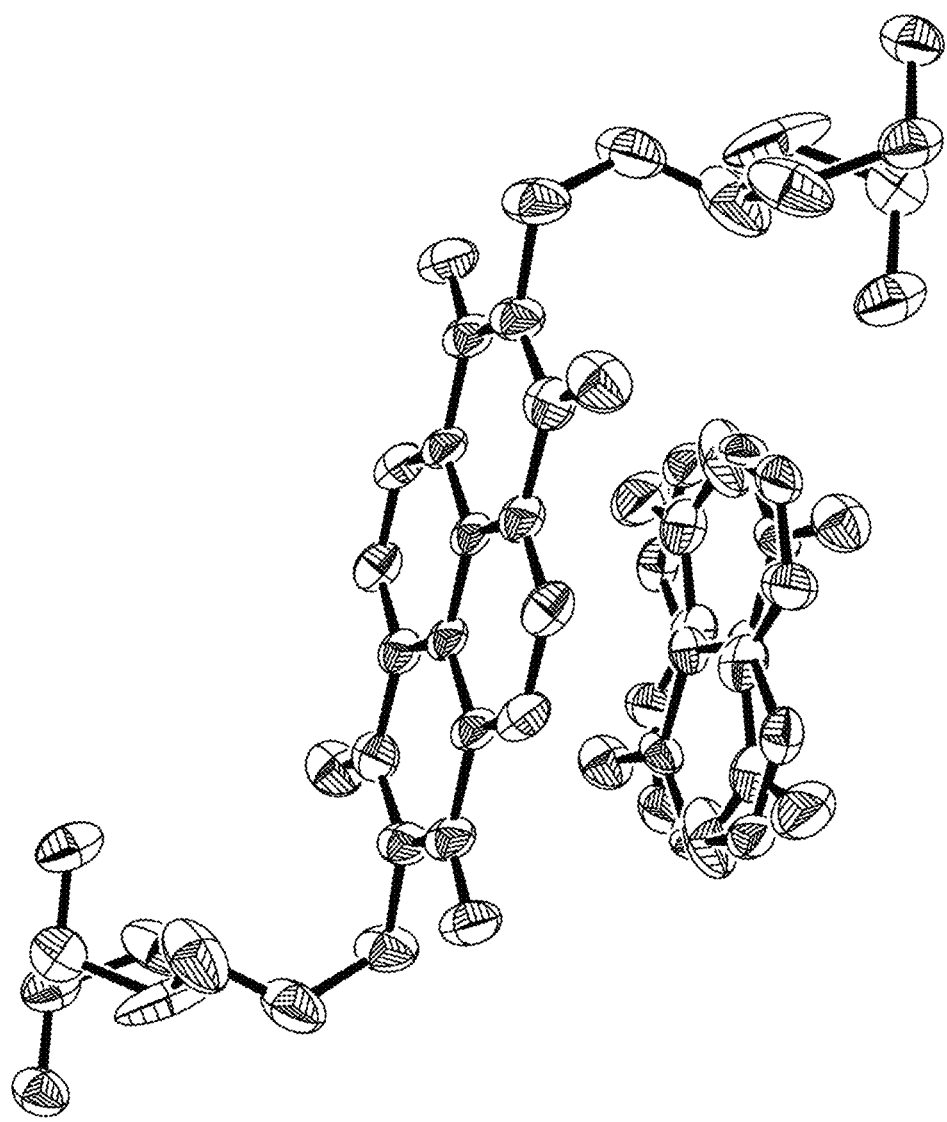
FIG. 31 is an ORTEP drawing of 2α•9β.

FIG. 31 is an ORTEP drawing of co-crystal 2α•9β. The hydrogen atoms are omitted for clarity. There is one naphthalene-based β and one naphthalene diimide-based (NPDI) α in the unit cell. There is positional disorder in the glycol α'-arm and the ring system of β. All ellipsoids are displayed at the 50% probability level.

G) 2α•11β: $C_{38}H_{33}N_3O_8$, M=659.67, triclinic, a=10.9811 (8), b=12.4287(8), c=12.9441(9) Å, α=94.620(5), β=112.518(5), γ=109.840(5)°, V=1489.33(18) Å$^3$, T=85(2) K, space group PI, Z=2, ρ=1.47 g·cm$^{-3}$, μ(Cu$_{Kα}$)=0.86 mm$^{-1}$, 4883 independent observed reflections, 3441 reflections with I>2σ(I), $R_{int}$=0.042, R[$F^2$>2σ($F^2$)]=0.058 wR($F^2$)=0.176.

Figure 32:
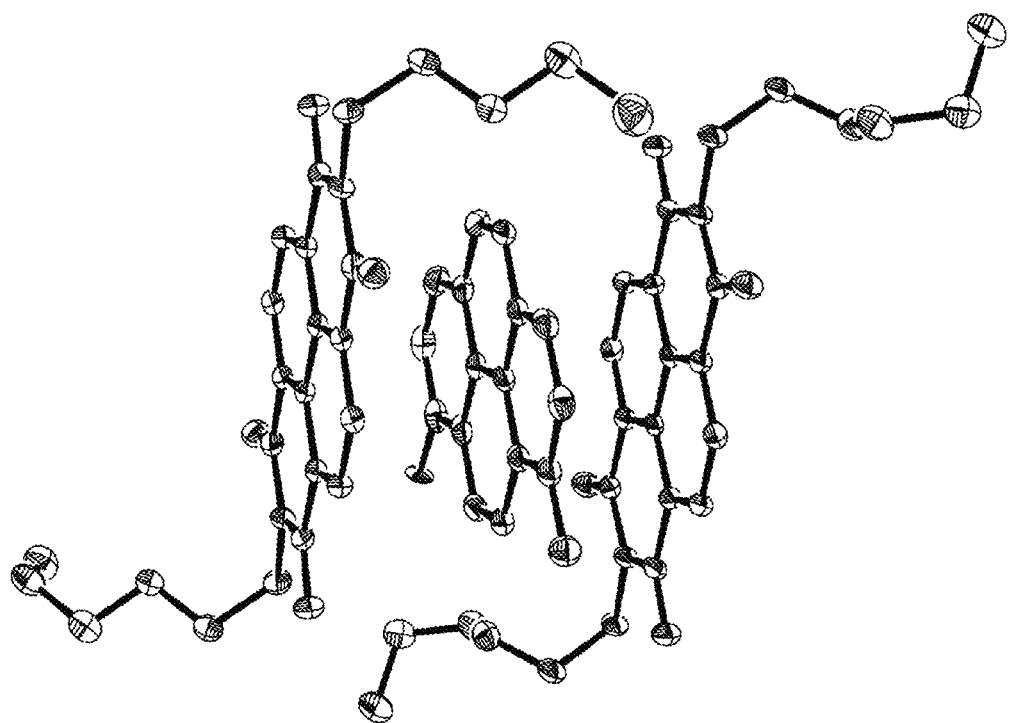
FIG. 32 is an ORTEP drawing of 2α•11β.

FIG. 32 is an ORTEP drawing of co-crystal 2α•11β. The hydrogen atoms are omitted for clarity. There is one asymmetric pyrene-based β and two crystallographically unique NPDI αs in the unit cell. The β has one amino arm at the 1-position. The asymmetry of the β results in substitutional disorder at the 1,8-positions within the lattice. All ellipsoids are displayed at the 50% probability level.

H) 5α•3β: $C_{28}H_{30}N_4O_8$, M=550.56, monoclinic, a=6.6667(3), b=23.3906(10), c=8.3455(3) Å, ρ=104.657 (3)°, V=1259.03(9) Å$^3$, T=84(2) K, space group Pc, Z=2, ρ=1.45 g·cm$^{-3}$, μ(CU$_{Kα}$)=0.11 mm$^{-1}$, 6787 independent observed reflections, 3829 reflections with I>2σ(I), $R_{int}$=0.080, R[$F^2$>2σ($F^2$)]=0.059, wR($F^2$)=0.141.

Figure 33:
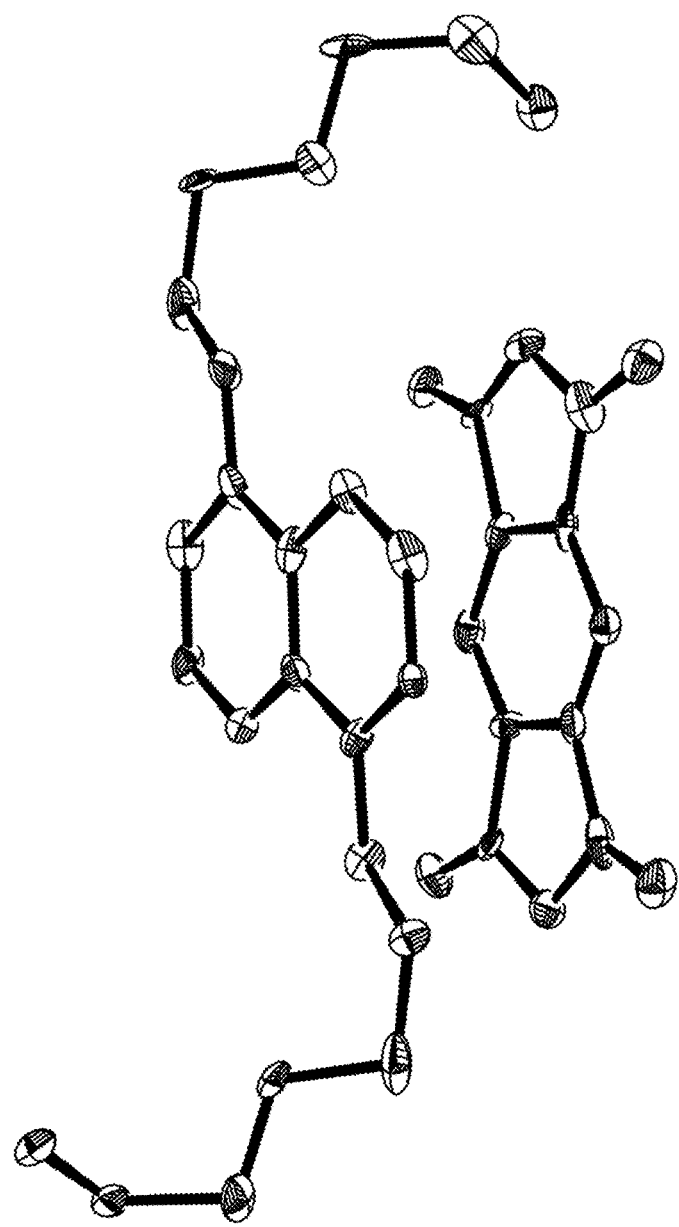
FIG. 33 is an ORTEP drawing of 5α•3β.

FIG. 33 is an ORTEP drawing of co-crystal 5α•3. The hydrogen atoms are omitted for clarity. There is one PMDI β and one napthalene-based α in the unit cell. All ellipsoids are displayed at the 50% probability level.

I) 5$_α$•4$_β$: $C_{30}H_{30}N_6O_4$, M=538.60, triclinic, a=6.8961(2), b=8.0293(3), c=12.3435(4) Å, α=89.213(1), β=83.730(2), γ=73.487(2)°, V=651.25(4) Å$^3$, T=100(2) K, space group PI, Z=1, ρ=1.37 g·cm$^{-3}$, μ(Cu$_{Kα}$)=0.76 mm$^{-1}$, 2233 independent observed reflections, 2176 reflections with I>2σ(I), $R_{int}$=0.018, R[$F^2$>2σ($F^2$)]=0.031, wR($F^2$)=0.084.

Figure 34:
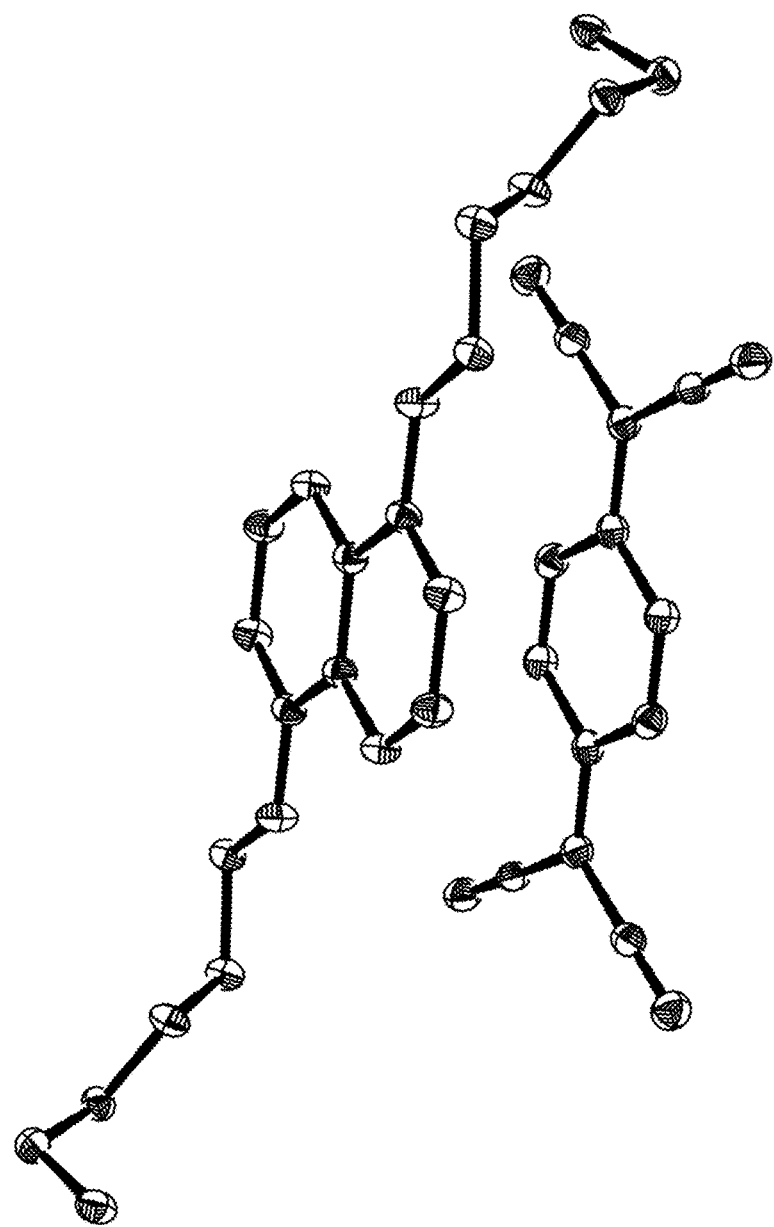
FIG. 34 is an ORTEP drawing of 5α•4β.

FIG. 34 is and ORTEP drawing of co-crystal 5α•4β. The hydrogen atoms are omitted for clarity. There is one TCNQ β and one naphthalene-based α in the unit cell. All ellipsoids are displayed at the 50% probability level.

J) 6α•3β: $C_{28}H_{28}N_2O_{10}$, M=552.52, monoclinic, a=6.6836(2), b=23.4173(6), c=8.3689(2) Å, β=106.174(2)°, V=1257.99(6) Å$^3$, T=100(2) K, space group P2$_1$/c, Z=2, ρ=1.46 g·cm$^{-3}$, μ(CU$_{Kα}$)=0.11 mm$^{-1}$, 3828 independent observed reflections, 2322 reflections with I>2σ(I), $R_{int}$=0.097, R[$F^2$>2σ($F^2$)]=0.051, wR($F^2$)=0.123.

Figure 35:
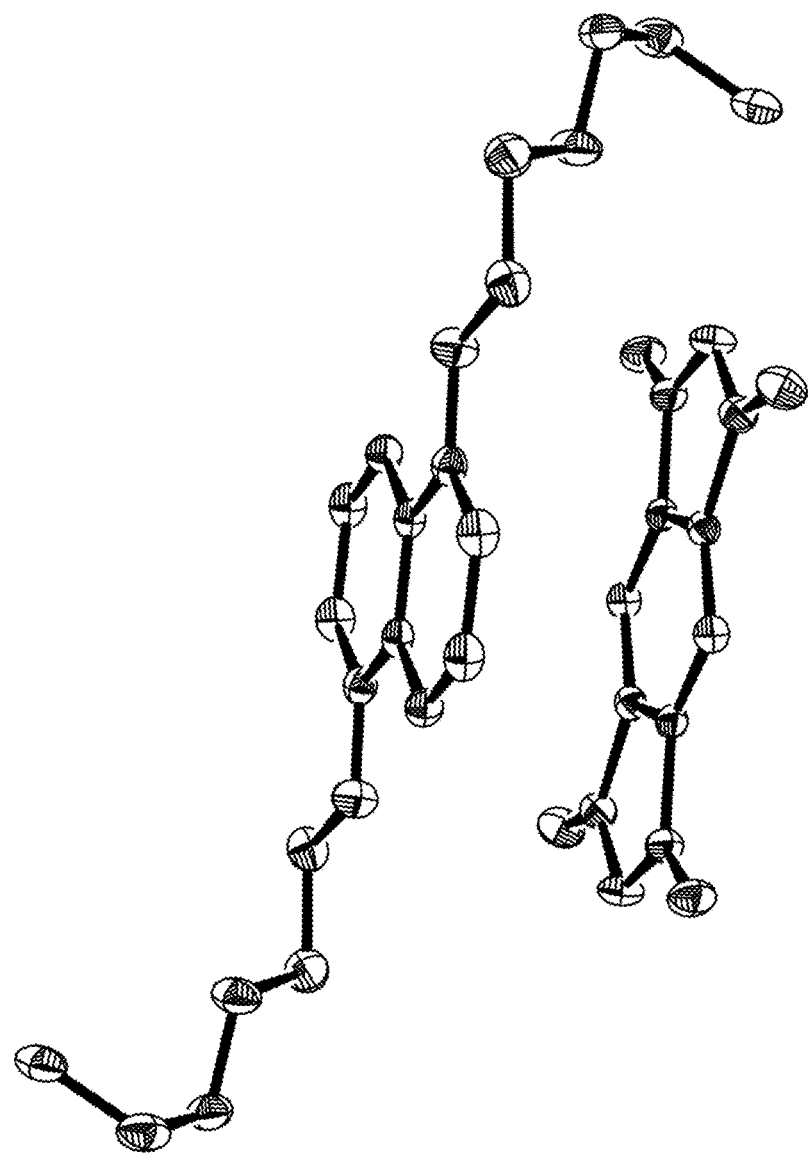
FIG. 35 is an ORTEP drawing of 6α•3β.

FIG. 35 is an ORTEP drawing of co-crystal 6α•3β. The hydrogen atoms are omitted for clarity. There is one PMDI β and one napthalene-based α in the unit cell. All ellipsoids are displayed at the 50% probability level.

The magnetic properties of LASO co-crystals are characterised by SQUID magnetometry (FIG. 39). Magnetic hysteresis is observed at low temperature for compounds 1α•9β and 1α•12β. Samples for SQUID magnetometry are prepared by packing LASO crystals into a non-magnetic gel capsule. Masses for the sample range from 10 mg to 30 mg. The magnetism as a function of temperature is also measured for both co-crystals (FIG. 40). Great care is taken during the preparation of LASO samples to prevent the introduction of magnetic impurities. Compounds 1α, 9β, 10β, and 12β are recrystallised multiple times and stored in a drybox prior to use. No metal instruments or containers are used during the process. Samples for SQUID magnetometry are prepared in a laminar flow hood. ICP-AES is performed by Galbraith Laboratories to directly address concerns over the possible presence of iron impurities. FIG. 41 are analysis reports of iron content in solvents used for the co-crystallisation of 1α•9β, 1α•10β, and 1α•12β: 1-chlorobutane, 1,2 dichloroethane, and diethyl ether. FIG. 44 are analysis reports of iron content on co-crystals 1α•9β and 1α•12β. The overall iron content is very low. The less than symbol (<) indicates that the iron content is below the sensitivity limit of the instrument. Iron analysis of both independent compounds, simple mixes of D-A molecules, and charge transfer crystals are also performed. As an example, to illustrate the overall low iron content in LASO starting materials, compounds 1α and 9β are analyzed (FIG. 42). Compounds 1α and 9β are coarsely mixed together to form a charge transfer powder and measured by both SQUID magnetometry and iron analysis (FIG. 43). In FIG. 43, the black is indicative of charge transfer and complexation. M(H) curves at 7° K for mixed powder of compound 1α and 9β. No hysteresis is observed, solely diamagnetic contribution from the powder and capsule container. Both graphs are of the same sample, with different x-axis scale to illustrate the lack of ferromagnetic hysteresis. Iron analysis report for the above mixed compound powder is provided (bottom image).

The low magnetic saturation signal observed indicates the possibility of extrinsic magnetisation. To further quantify whether magnetism is derived from LASO networks or a tertiary impurity, low-temperature magnetic force microscopy (MFM) is performed.

These MFM measurements are performed at 45° K in two modes: lift-off and z-spectroscopy. In the case of the former, the topography of compound 1α•12β is first measured (FIG. 45). A second scan of the same region with a magnetised cantilever is performed while approximately 10, 20, 30, 50, and 80 nm above the surface. At all heights, topography is still visible in the measurement while in phase-locked loop mode (FIG. 45).

The influence of topography is evident in the scan 80 nm above the crystal surface. Therefore, Z-spectroscopy is performed to ascertain whether LASO materials are inherently magnetic (FIG. 46). The presence of both attractive and repulsive interactions with a magnetized cantilever proves that magnetic domains exist within the material. Though a prominent magnetic hysteresis loop is observed by SQUID magnetometry, the lack of a characteristic repulsive force in Z-spectroscopy suggests that LASO networks are not inherently magnetic.

Samples studied by low temperature MFM are also charge compensated at 800 mV. Kelvin-probe measurements on the surface of compound 1α•12β show some differences in charge distribution, possibly due to ferroelectric domains.

Ferroelectric hysteresis loops are obtained at low temperatures for compounds 1α•9β, 1α•10β and 1α•12β. Large voltages are needed to achieve polarization saturation (>1 kV). This large voltage results in crystal melting and dielectric breakdown at higher temperatures. Thus, to obtain hysteresis at room temperature, LASO materials are underpolarized to obtain hysteresis.

Figure 48A:
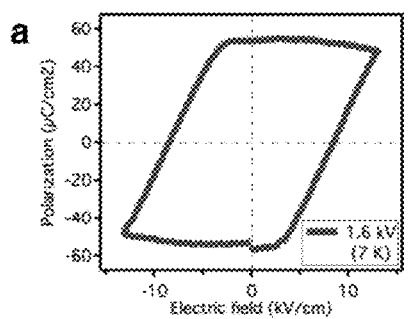
FIGS. 48a-b are polarization hysteresis of compound 1α•12β at (a) 7 K and up to (b) 35 K.
Figure 48B:
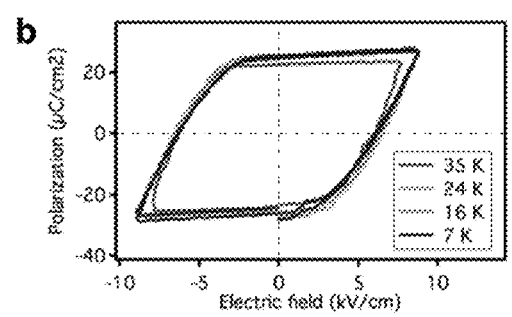

LASO materials based on Pyrene demonstrated hysteresis from low temperature (7 K, 150 K) upto room temperature (FIG. 47). Compounds based on tetrathiafulvalene showed large hysteresis at low temperatures with nice saturation upto 1.6 kV (FIG. 48). This unexpectedly large polarization is likely the result of CT processes and proton dynamics.

Challenges with higher temperature and higher voltage measurements prevent the recording of saturated hysteresis curves. The main issue is likely avalance breakdown and crystal melting at high voltages (>1 kV). Devices that begin with long needles (FIG. 49a) are destroyed and emerge as re-crystallized solids on the electrode (FIG. 49b). Crystal networks can be formed into ferroelectric devices with gold paste and wire. At high voltages (>900V) and higher temperatures, crystals frequently melt likely due to high leakage currents and avalanche breakdown.

Example 1

1α (Scheme 1): Pyromellitic dianhydride (5.00 g, 22.9 mmol) is added to a 40 mL pressure tube containing 2-(2-aminoethoxy)ethanol (4.7 mL, 46.8 mmol). The reaction mixture is heated to 160° C. and stirred for 24 hours. After cooling to ambient temperatures, the solid is dissolved in trifluoroacetic acid (100 mL), and the resulting solution is stirred for 24 hours. The mixture is then neutralized with a saturated $NaHCO_2$ aqueous solution, and the precipitate is filtered and washed with $H_2O$ (3×100 mL).

The crude product is recrystallized twice from THF and $Et_2O$ to yield a sticky white solid (5.49 g, 61%) of 1α. $^1H$ NMR (500 MHz, $CD_3COCD_3$, 298 K): δ=8.21 (s, 2H), 3.90 (t, J=5.9 Hz, 4H), 3.75 (t, J=5.9 Hz, 4H), 3.55 (m, 8H). $^{13}C$ NMR (125 MHz, $CD_3COCD_3$, 298 K): δ=38.6, 61.9, 67.7, 71.6, 119.3, 137.4, 166.9. HR ESI: calcd for $[M+H]^+$ m/z=393.1298; found m/z=393.1299.

Scheme 1

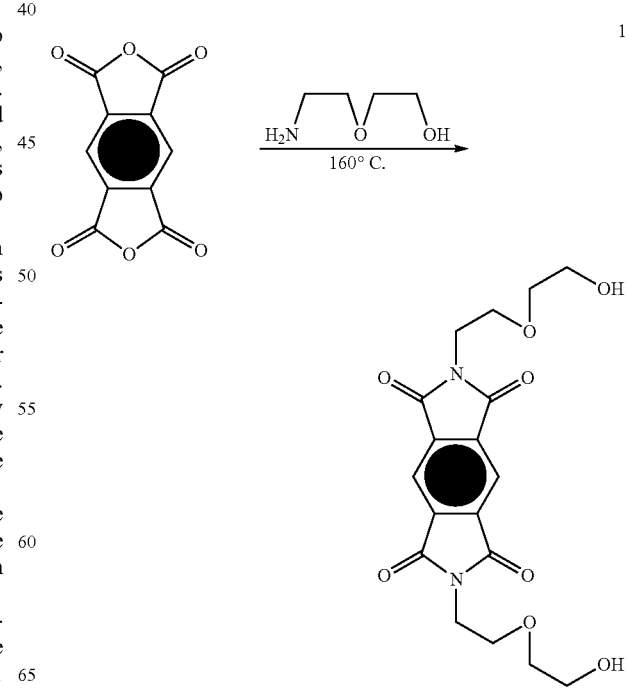

Discussion

Using the LASO platform, ten co-crystals are grown (FIG. 2a) from 12 αs and βs. As the co-crystals grew, three distinguishing features emerged: (i) growth rate, (ii) size, and (iii) morphology. The growth rate is controlled by adjusting the total concentration of α and β in the crystallizing solution, and crystal size can be changed with growth time. The morphology of the materials (FIG. 2a) does not change with subsequent crystallizations. Only one system (1α•7β) is found to contain a small amount of polymorphic material. Seven of the co-crystals grew as long prisms (1α•9β, 1α•10β, 1α•12β, 2α•9β, 2α•11β, 6α•3β, 5α•3β). The system 5α•4β also grew as a prism but assumed a shorter cuboidal shape. Complexes 1α•7β and 1α•8β have the most unusual morphology. These materials grew rapidly in two dimensions, giving them the appearance of thin sheets.

Figure 2B:
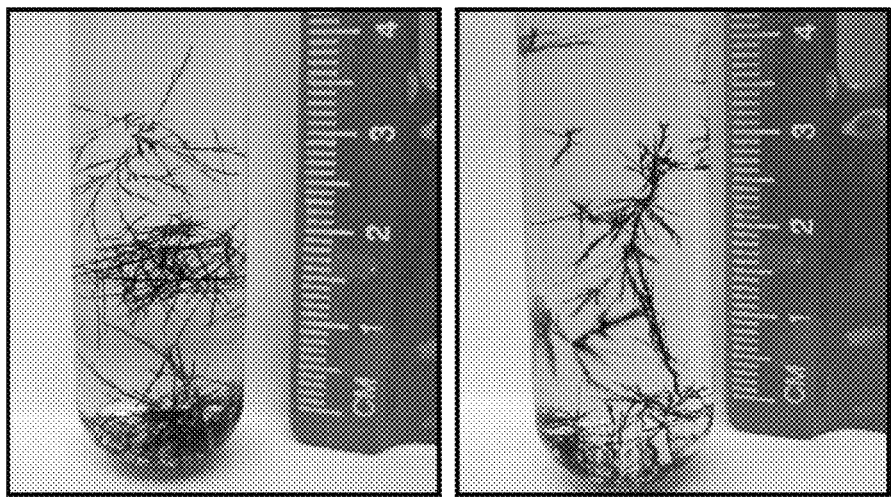

Using the concentration of α and β (Table 1), the growth time of high-quality single crystals (cm length-scale) is optimized to a period of several days (FIG. 2a). The LASO systems 6α•3β and 5α•3β are crystallized from $H_2O$/N-methylpyrrolidone and takes 5 days to reach the maximum size. The eight remaining co-crystals finish growing slightly faster (3 days) from anhydrous 1-chlorobutane/1,2-dichloroethane/diethyl ether. Notably, many of the αβ pairs show visible co-crystals ~2 hours after being mixed in the crystallizing solution, indicating the strong drive for self-assembly. Although LASO materials are capable of expedient growth, strict adherence to the optimized solvent conditions is crucial for successful co-crystallization. FIG. 2b shows the prevalent out-growth of 1α•9β when the crystallizing solution is contaminated with trace amounts of $H_2O$, indicating the strong influence solvent conditions have on the crystal morphology.

Figure 37:
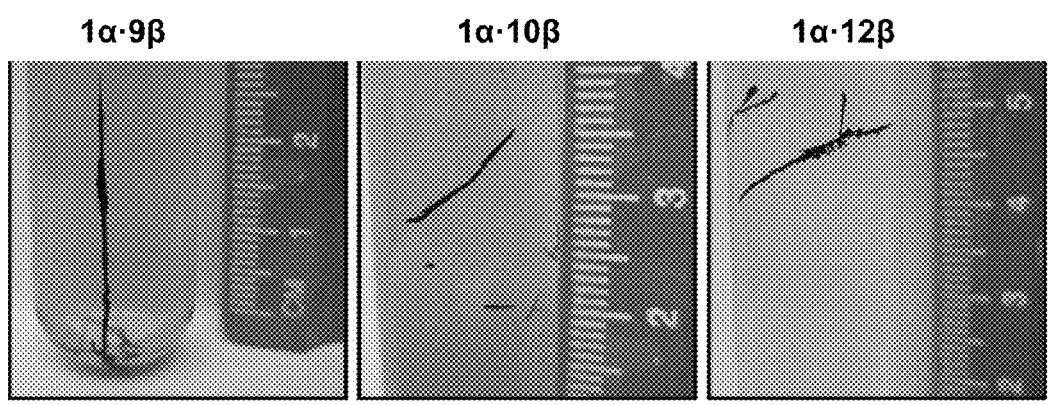
FIG. 37 are images of complex 1α•9β and 1α•10β growing along the glass of a crystallizing container.

FIG. 37 provides images of complex 1α•9β and 1α•10β growing along the glass of the crystallising container. This type of growth indicates the possibility of controlled growth of LASO on surfaces.

Figure 2C:
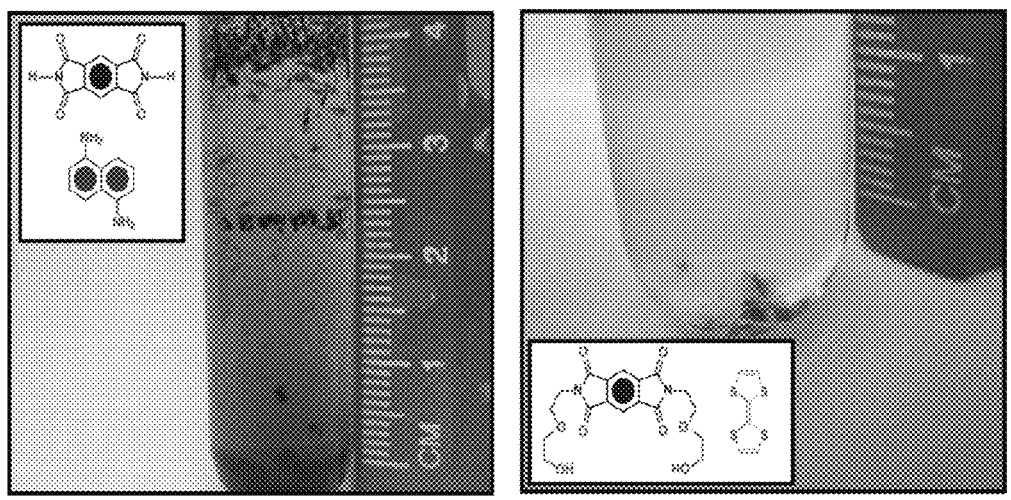

Two co-crystallizations of DA pairs are used as controls in order to demonstrate that arms are crucial to the self-assembly of LASO materials (FIG. 2c). The first experimental control is the growth of 3β•9β, a co-crystal with two βs. This co-crystal is equivalent to LASO systems 1α•9β and 6α•3β, except it lacks a α'-arm. Without an α'-arm, neither component in 3β•9β can engage in adaptive intermolecular recognition, the phenomenon which is the key attribute in the LASO platform. Co-crystal 3β•9β is grown from diffusion of 1-chlorobutane into 1,2-dichloroethane/diethyl ether/N-methylpyrrolidone under anhydrous conditions. For the crystallization, 3β and 9β are used in 1:2 ratio at a concentration of 2 mg/mL of 3β. 3β•9β co-crystals grew as black in color, similar to the color of both 1α•9β and 6α•3β, yet the crystal size is significantly smaller and the quality is not adequate for structure determination by X-ray crystallography (FIG. 2c). This result suggests that the α'-arm, used for adaptive intermolecular recognition by the αs, is crucial for self-assembly in LASO systems.

The second control experiment is to co-crystallize tetrathiafulvalene (TTF) with 1α. A crystal of TTF•12β is the co-crystal equivalent of 1α•12β but lacking the β-arms. This control demonstrates that the β-arms are important for crystal growth. Diffusion of 1-chlorobutane into 1,2-dichloroethane/diethyl ether is used as the solvent system and, after 14 days at −22° C., only discolored crystals of 1α are found to grow. For the crystallization, 1β and TTF are used in 1:2 ratio at a concentration of 2 mg/mL of 1β. This result shows that the β-arm is not a passive observer since these appendages also promote the co-crystallization of α and β. From these control experiments, it appears that both the conformationally flexible α'-arm and the rigid β-arm must be present for self-assembly to occur. These arms appear to enhance the supramolecular affinity between αβ CT pairs and provide stability (ΔG of the lattice ground state) to the LASO network solid through interstack H-bonding.

FIG. 3 illustrates the use of adaptive intermolecular recognition by an α inside a LASO network solid. In 1α•9β, the flexible α'-arms of 1α adopt two distinct conformations in the lattice (acceptor 1 and acceptor 2) to drive the system to an energetically favorable network topology. The arm conformation of the two as mold to adjoining intermolecular recognition sites. The conformational isomer of α can vary significantly (FIG. 4 and FIG. 5) depending upon the β that is used to generate a LASO network solid. In the local network structure 1α•9β, α'-α and α'-α' H-bonds (FIG. 3) bind neighboring as together, and the α'-β and α-β arm interactions form intermolecular H-bonds between adjacent αs and βs. The resulting topology is a highly interconnected three-dimensional (3-D) supramolecular network (FIG. 5a).

The crystal superstructures for all ten LASO materials are elucidated from single-crystal X-ray diffraction data (FIG. 4). Each of the systems has stacks of alternating donors and acceptors (DADA) and a multidimensional H-bonded network (1D-3D). The space groups of the LASO co-crystals are listed in Table 3. While eight of the systems exhibit the typical 1-D packing of a mixed stack, two co-crystals are distinct from the rest. Systems 1α•7β and 1α•8β (FIG. 2a), display a previously unknown packing motif for CT crystals (FIG. 5). In these systems, the ratio of α (acceptor) to β (donor) is 2:1 where the αs engage in CT with the β through π-face-to-π-face (ff) and edge-to-π-face stacking (ef), respectively. As a result of the ff and ef packing, there are two CT axes (bidirectional CT) in these systems (1α•7β and 1α•8β) that intersect at an angle of ~90°. As referred to herein, this packing motif is a "crossed stack". The resulting arrangement is a checker board-pattern of αs and βs which lie parallel to the plane [001].

TABLE 3

| Co-Crystal | Space Group | $\rho^b$ |
| --- | --- | --- |
| 1α · 9β | P1 | 0.68 |
| 1α · 10β | Pn | 0.89 |
| 1α · 12β | P2$_1$ | 0.43 |
| 1α · 7β | P1 | 0.53$_{ff}$, 0.47$_{ef}$ |
| 1α · 8β | P1 | 0.57$_{ff}$, 0.42$_{ef}$ |
| 2α · 9β | P$\bar{1}$ | 0.58 |
| 2α · 11β | P$\bar{1}$ | 0.44 |
| 6α · 3β | P2$_1$/c | 0.27 |
| 5α · 3β | P$\bar{1}$ | 0.45 |
| 5α · 4β | Pc | 0.12 |

Importantly for self-assembly, the intermolecular H-bonds between the arms establish the pattern of local connectivity for neighboring molecules. It is the global topology, however, of the H-bonded network that is a primary distinguishing feature of a LASO co-crystal. In FIG. 5, a noncovalent connectivity diagram (Etter, M. C. *Acc. Chem. Res.* 1990, 23, 120-126; Etter, M. C., et al. *Acta Crystallogr., Sect. B: Struct. Sci* 1990, 46, 256-262; Bernstein, J., et al. *Angew. Chem. Int. Ed.* 1995, 34, 1555-1573; Motherwell, W. D. S., et al. *Acta Crystallogr., Sect. B: Struct. Sci* 1999, 55, 1044-1056; Grell, J., et al. *Acta Crystallogr., Sect. B: Struct. Sci* 1999, 55, 1030-1043; Grell, J., et al. *Acta Crystallogr., Sect. B: Struct. Sci* 2000, 56, 166-166, all incorporated herein by reference) for three systems (1α•9β, 1α•10β, 1α•12β) is used to illustrate the diverse global topology of the H-bonded network in a LASO platform. This structural feature is partially ascribed to the ability of 1α to engage in adaptive intermolecular recognition. By varying the identity of β in these three co-crystals, the binding conformation of 1α (inset of FIG. 5) along with the network topology changes. FIG. 5 shows that topologically, the H-bonding in 1α•9β can be represented by a single 3-D network (FIG. 5a). By contrast, co-crystals 1α•10β and 1α•12β each consist of interpenetrating network topologies. The former is found to be fashioned from a pair of distinct 3-D networks (FIG. 5b), and the latter can be represented as a 3-D network entwined with a series of repeating 2-D networks, respectively.

In addition to the structural characteristics, the choice of the corresponding DA pairs (αβ) has a significant effect on the value of ρ (ionicity) for each system (Eddaoudi, M., et al. *Acc. Chem. Res.* 2001, 34, 319-330, incorporated herein by reference). In Table 3, ρ for the ten LASO co-crystals is shown to vary ρ=0.12-0.89, another result that highlights the modularity of LASO network solids. Three of the systems can be classified as ionic (1α•9β, 1α•10β, 2α•9β), five co-crystals are mixed valent (1α•7β, 1α•8β, 1α•12β, 2α•11β, 5α•3β), and the remaining two materials are neutral (5α•4β, 6α•3β). For convenience, the crossed stack systems 1α•7β and 1α•8β are grouped into the mixed valence category. The two crossing stacks (ff and ef) are found, however, to have different values for ρ (Table 3). This dichotomy makes the crossed stack systems a mixed valent/neutral hybrid co-crystal. Four of the eight mixed stack systems ($1_\alpha$•$9_\beta$, $1_\alpha$•$10_\beta$, $1_\alpha$•$12_\beta$, $5_\alpha$•$3_\beta$) display the spectroscopic signature of an asymmetric lattice caused by the dimerization of donors and acceptors. In one-dimensional CT systems, this phenomenon is the result of quantum instabilities, e.g., the Peierls (Torrance, J. B., et al. *Phys. Rev. Lett.* 1981, 46, 253-257; Torrance, J. B., et al. *Phys. Rev. Lett.* 1981, 47, 1747-1750; Iwasa, Y., et al. *Phys. Rev. B: Condens. Matter* 1990, 42, 2374-2377; Bruinsma, R., et al. *Phys. Rev. B: Condens. Matter* 1983, 27, 456-466; Girlando, A., et al. *J. Chem. Phys.* 1983, 79, 1075-1085; Masino, M., et al. *Phys. Chem. Chem. Phys.* 2001, 3, 1904-1910; Horiuchi, S., et al. *Science* 2003, 299, 229-232; Tokura, Y., et al. *Solid State Commun.* 1986, 57, 607-610; Girlando, A., et al. *Solid State Commun.* 1986, 57, 891-896; Collet, E., et al. *Science* 2003, 300, 612-615; Koshihara, S., et al. *Phys. Rev. B: Condens. Matter* 1990, 42, 6853-6856; Mitani, T., et al. *Phys. Rev. Lett.* 1984, 53, 842-845; Tokura, Y., et al. *Phys. Rev. B: Condens. Matter* 1988, 38, 2215-2218; and Iwasa, Y., et al. *Phys. Rev. B: Condens. Matter* 1989, 39, 10441-10444, all incorporated herein by reference) and Spin-Peierls transitions (Girlando, A., et al. *Solid State Commun.* 1985, 54, 753-759; Hughes, R. C., et al. *J. Chem. Phys.* 1968, 48, 1066-1076; Huizinga, S., et al. *Phys. Rev. B: Condens. Matter* 1979, 19, 4723-4732; Hasegawa, T., et al. *Solid State Commun.* 1997, 103, 489-493; Kagawa, F., et al. *Nature Phys.* 2010, 6, 169-172, all incorporated herein by reference).

Several LASO materials are found to contain structural disorder in the lattice. Systems 1α•8β and 2α•11β both contain asymmetric βs that exhibit substitutional disorder. In 2α•9β, the α'-arm of 2α and the aromatic ring system of 9β are found to have positional disorder. The lack of long-range periodicity has a noticeable effect on the self-assembly since 15 equivalents of 9β (Table 1) are needed in the crystallizing solution before co-crystals begin to grow.

The redox potentials of the first electron transfer processes of the individual species 1α,9β,10β and 12β are recorded in DMF at 298° K using both CV and SWDPV (Table 4). In the case of an irreversible oxidation process for compounds 9β and 10β, the redox potential determined by CV is estimated, assuming a one-electron process based on the expected separation between anodic and cathodic peaks for a Nernstian process.

TABLE 4

| Compound | $CV^a$/V | C $SWDPV^a$/V |
|---|---|---|
| $1\alpha^b$ | −0.73 | −0.73 |
| $9\beta^c$ | +0.80$^d$ | +0.82 |
| $10\beta^c$ | +0.83$^d$ | +0.81 |
| $12\beta^c$ | +0.40 | +0.40 |

$^a$Collected at 298° K in argon-purged DMF
$^b$First reduction process
$^c$First oxidation process
$^d$Irreversible process, estimated assuming a one-eletron process The LASO platform presented herein is a type of molecular recognition that can amplify the growth of donor and acceptor co-crystals (cm length-scale) under ambient conditions in 3-5 days. The LASO strategy has three components which work cooperatively to promote growth of the network solid. The main constituent is a donor/acceptor (α-complement) that uses flexible appendages (diethylene glycol, α'-arm) to form intermolecular H-bonds in the crystal. The second constituent is a smaller CT partner (β-complement) with short and relatively rigid H-bonding functionalities (C=O, —NH$_2$, —OH, β-arm) that is incorporated into the LASO network through molecular recognition with the α-complement. The final element is the solvent system that promotes the co-crystallization of the α-complement and β-complement. With this platform, supramolecular architectures combine the H-bonded network and stacks of alternating donors and acceptors. Not only does the LASO strategy produce network solids that are capable of amplified co-crystal growth, but it creates an entirely new 2-D donor and acceptor packing motif made of two perpendicular CT axes, i.e., the crossed stack.

As further described herein, a molecular design that allows donor and acceptor molecules to self-assemble into CT ferroelectric networks at ambient temperatures is afforded. The co-crystals solve the long-standing challenge that DA mixed stack materials can exhibit a ferroelectric $T_c$ above room temperature. The demonstration of ferroelectric properties in an organic network enables new opportunities to produce these systems into new forms with exciting function such as electrically addressable hydrogels, ferroelectric catalysts, and CT-based sensitizers for photovoltaics, among others. The combination of donor-acceptor interactions with hydrogen bonded networks offers a promising supramolecular platform to design novel organic electronic structures.

The disclosures of all articles and references, including patents, are incorporated herein by reference. The invention and the manner and process of making and using it are now described in such full, clear, concise and exact terms as to enable any person skilled in the art to which it pertains, to make and use the same. All references cited in this specification are incorporated herein by reference. It is to be understood that the foregoing describes preferred embodiments of the present invention and that modifications may be made therein without departing from the spirit or scope of the present invention.

What is claimed is:

1. An organic charge-transfer (CT) co-crystal consisting essentially of an electron acceptor molecule (A) and an electron donor molecule (D), such that one of (A) and (D) is incorporated into the other of (A) and (D) through molecular linkages in a solvent system to form a co-crystalline supramolecular network, the co-crystal characterized by having a crystal superstructure comprising a mixed stack lattice (DADADA) and a topological hydrogen-bonded network, said organic CT co-crystal wherein A is selected from the group consisting of

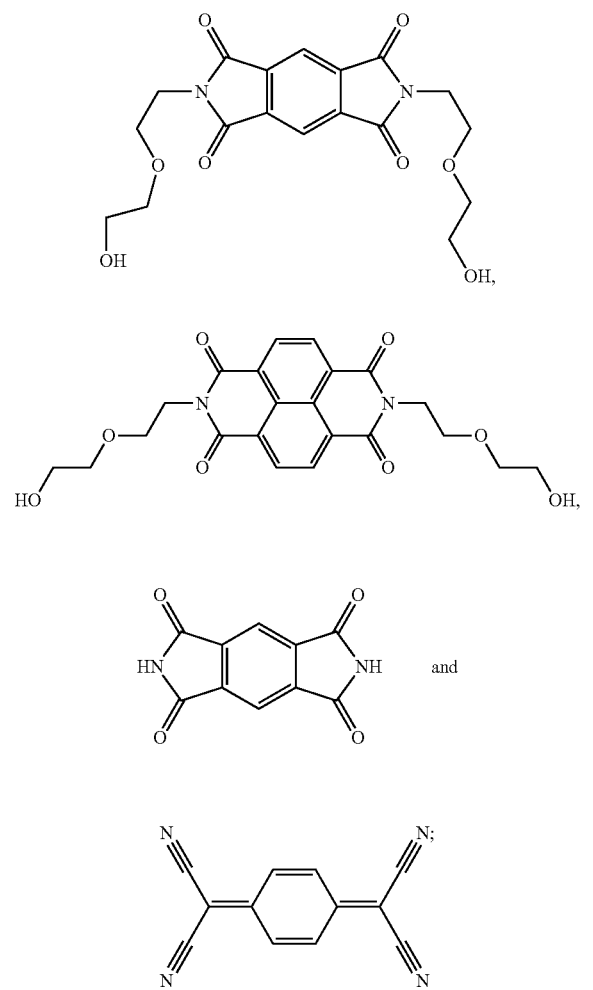

and D is selected from the group consisting of

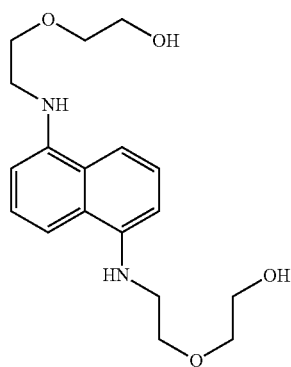

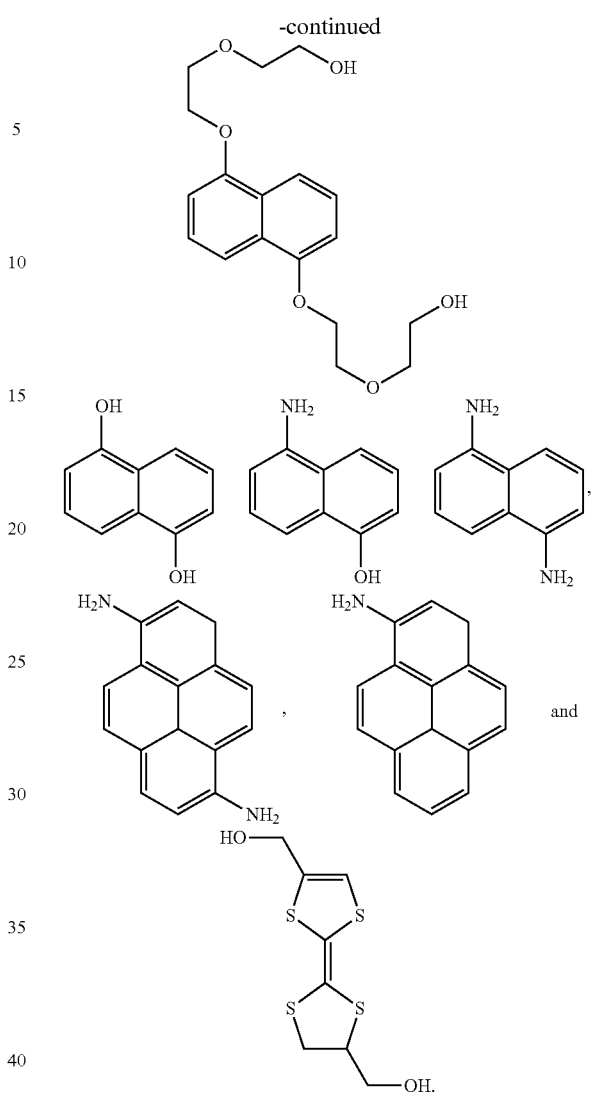

2. The organic CT co-crystal according to claim 1, wherein A is a diimide.

3. The organic CT co-crystal according to claim 1, wherein the solvent system is one or more organic solvents.

4. The organic CT co-crystal according to claim 3, wherein the solvent system is selected from the group consisting of dichloroethane/diethyl ether and N-methylpyrrolidone.

5. The organic CT co-crystal according to claim 1, wherein one of the (A) and (D) has a substituent that is a diethylene glycol moiety.

6. The organic CT co-crystal according to claim 1, wherein the hydrogen-bonded network comprises interstack and intrastack hydrogen bonds.

7. The organic CT co-crystal according to claim 1, wherein the co-crystal is devoid or substantially devoid of solvent.

8. The organic CT co-crystal according to claim 1, wherein one of the (A) and the (D) has a substituent that has one or more hydrogen-bonding recognition sites.

9. The organic CT co-crystal according to claim 8, wherein the one or more hydrogen-bonding recognition sites is independently selected from the group consisting of amino, carbonyl, ether and hydroxyl moieties.

10. The organic CT co-crystal according to claim 1, wherein the (A) has at least four substituents.

11. The organic CT co-crystal according to claim 10, wherein the (D) has at least one substituent.

12. The organic CT co-crystal according to claim 1, wherein the co-crystal is grown in the dark, under ambient conditions.

13. The organic CT co-crystal according to claim 12, wherein the co-crystal is grown using liquid diffusion.

14. The organic CT co-crystal according to claim 1 selected from the group consisting of

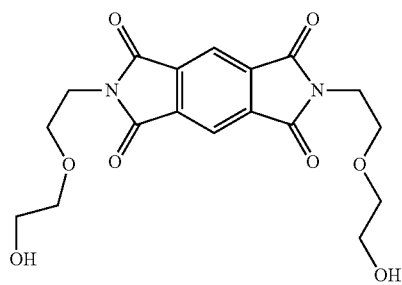,

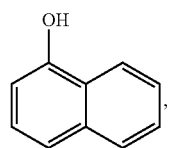,

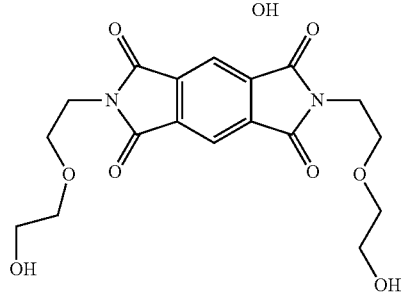,

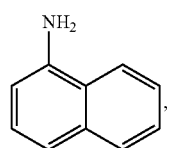,

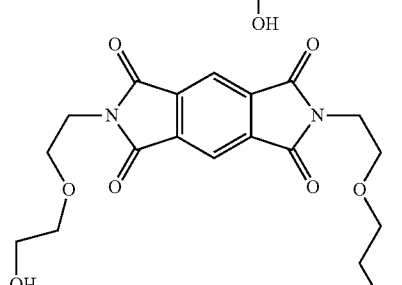,

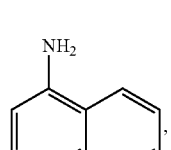,

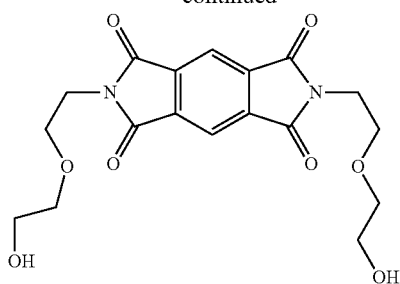

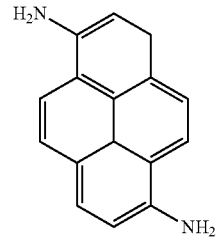,

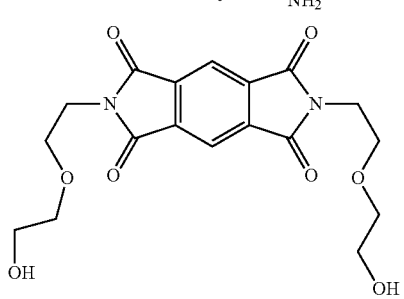,

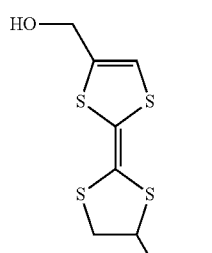,

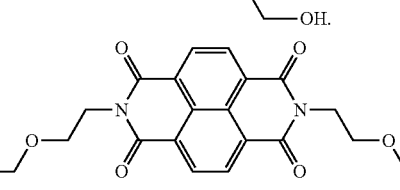,

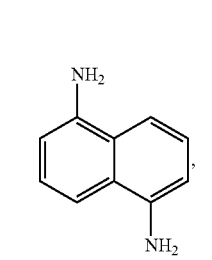,

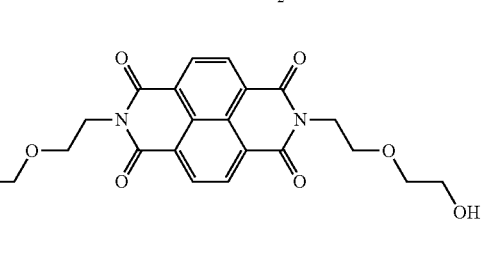,

27
-continued
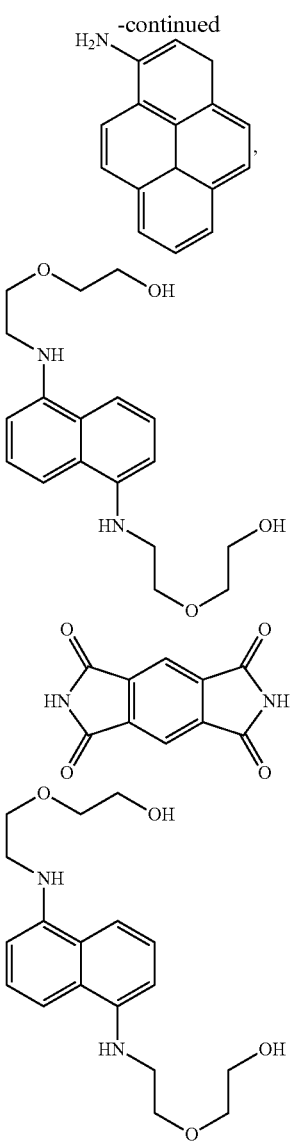
28
-continued
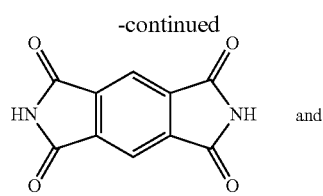
and
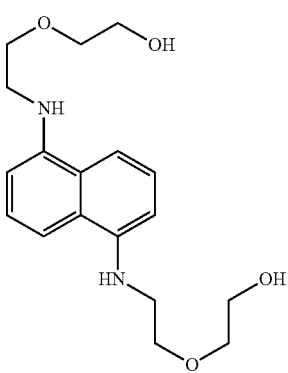
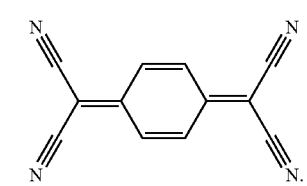
15. The organic CT co-crystal according to claim 1, wherein the co-crystal has a packing motif that is a crossed stack.
* * * * *